(12) United States Patent
Sun et al.

(10) Patent No.: US 9,890,162 B2
(45) Date of Patent: Feb. 13, 2018

(54) BICYCLIC AROMATIC CARBOXAMIDE COMPOUNDS USEFUL AS PIM KINASE INHIBITORS

(71) Applicant: Incyte Corporation, Wilmington, DE (US)

(72) Inventors: Yaping Sun, Lansdale, PA (US); Hao Feng, Glen Mills, PA (US); Yun-Long Li, Chadds Ford, PA (US); Song Mei, Wilmington, DE (US); Jun Pan, Media, PA (US); Anlai Wang, Wilmington, DE (US); Hai-Fen Ye, Newark, DE (US); Ke Zhang, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/405,742

(22) Filed: Jan. 13, 2017

(65) Prior Publication Data

US 2017/0253587 A1    Sep. 7, 2017

Related U.S. Application Data

(63) Continuation of application No. 14/797,765, filed on Jul. 13, 2015, now Pat. No. 9,580,418.

(60) Provisional application No. 62/024,333, filed on Jul. 14, 2014.

(51) Int. Cl.
| | |
|---|---|
| *C07D 471/04* | (2006.01) |
| *C07D 491/107* | (2006.01) |
| *C07D 405/14* | (2006.01) |
| *C07D 401/14* | (2006.01) |

(52) U.S. Cl.
CPC ......... *C07D 471/04* (2013.01); *C07D 401/14* (2013.01); *C07D 405/14* (2013.01); *C07D 491/107* (2013.01)

(58) Field of Classification Search
CPC .............. C07D 471/04; C07D 491/107; C07D 405/14; C07D 401/14
See application file for complete search history.

(56) References Cited

U.S. PATENT DOCUMENTS

| | | |
|---|---|---|
| 8,168,794 B2 | 5/2012 | Burger et al. |
| 8,329,732 B2 | 12/2012 | Burger et al. |
| 9,200,004 B2 | 12/2015 | Xue |
| 9,278,950 B2 | 3/2016 | Li et al. |
| 9,340,546 B2 | 5/2016 | Ahmad |
| 9,540,347 B2 | 1/2017 | Vechorkin et al. |
| 9,550,765 B2 | 1/2017 | Xue et al. |
| 9,556,197 B2 | 1/2017 | Li et al. |
| 9,580,418 B2 | 2/2017 | Sun et al. |
| 9,676,750 B2 | 6/2017 | Li et al. |
| 2011/0059961 A1 | 3/2011 | Wang et al. |
| 2012/0114663 A1 | 5/2012 | Gelfand et al. |
| 2012/0225062 A1 | 9/2012 | Burger et al. |
| 2013/0057956 A1 | 3/2013 | Iwasa |
| 2014/0086941 A1 | 3/2014 | Reddy et al. |
| 2014/0088117 A1 | 3/2014 | Burch et al. |
| 2014/0163000 A1 | 6/2014 | Ahmad |
| 2014/0200216 A1 | 7/2014 | Li et al. |
| 2014/0200227 A1 | 7/2014 | Xue et al. |
| 2015/0057265 A1 | 2/2015 | Li et al. |
| 2015/0329534 A1 | 11/2015 | Xue et al. |
| 2016/0009714 A1 | 1/2016 | Sun et al. |
| 2016/0009726 A1 | 1/2016 | Vechorkin et al. |
| 2016/0137626 A1 | 5/2016 | Li et al. |
| 2016/0347735 A1 | 12/2016 | Vechorkin et al. |
| 2017/0096411 A1 | 4/2017 | Vechorkin et al. |
| 2017/0121310 A1 | 5/2017 | Jia et al. |
| 2017/0158670 A1 | 6/2017 | Vechorkin et al. |
| 2017/0182017 A1 | 6/2017 | Xue et al. |
| 2017/0190716 A1 | 7/2017 | Li et al. |

FOREIGN PATENT DOCUMENTS

| | | |
|---|---|---|
| CN | 101568527 | 10/2009 |
| CN | 102985426 | 3/2013 |
| CN | 103664878 | 3/2014 |
| EP | 2637650 | 9/2013 |
| EP | 2743269 | 6/2014 |
| WO | WO 2002/000196 | 1/2002 |
| WO | WO 2002/055489 | 7/2002 |
| WO | WO 2002/093173 | 11/2002 |
| WO | WO 2003/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |
| WO | WO 2008/002676 | 1/2008 |
| WO | WO 2008/022164 | 2/2008 |
| WO | WO 2008/045252 | 4/2008 |
| WO | WO 2008/054749 | 5/2008 |
| WO | WO 2008/058126 | 5/2008 |

(Continued)

OTHER PUBLICATIONS

Magnuson, Future Oncol, vol. 6(9), 1461-1478, 2010.*
Kirschner, JNCI J Natl Cancer Inst, 107(2), 2015, 1-11.*
Amson et al., "The human protooncogene product p33pim is expressed during fetal hematopoiesis and in diverse leukemias," Proc. Nat. Acad. Sci., USA, 1989, 86:8857-61.

(Continued)

*Primary Examiner* — D M Seaman
(74) *Attorney, Agent, or Firm* — Fish & Richardson P.C.

(57) ABSTRACT

The present disclosure describes bicyclic aromatic carboxamide derivatives, as well as their compositions and methods of use. The compounds inhibit the activity of the Pim kinases, and are useful in the treatment of diseases related to the activity of Pim kinases including, e.g., cancer and other diseases.

70 Claims, No Drawings

(56) References Cited

FOREIGN PATENT DOCUMENTS

| | | |
|---|---|---|
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/135650 | 11/2010 |
| WO | WO 2010/148351 | 12/2010 |
| WO | WO 2011/008487 | 1/2011 |
| WO | WO 2011/025859 | 3/2011 |
| WO | WO 2011/028685 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130342 | 10/2011 |
| WO | WO 2011/163195 | 12/2011 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/20370 | 2/2013 |
| WO | WO 2013/020371 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/089379 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014/106706 | 7/2014 |
| WO | WO 2014/110574 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |
| WO | WO 2014/150276 | 9/2014 |
| WO | WO 2014/151008 | 9/2014 |
| WO | WO 2014/151634 | 9/2014 |
| WO | WO 2015/021153 | 2/2015 |

(56) References Cited

FOREIGN PATENT DOCUMENTS

| WO | WO 2015/027124 | 2/2015 |
|---|---|---|
| WO | WO 2015/131031 | 9/2015 |
| WO | WO 2015/157257 | 10/2015 |
| WO | WO 2015/168246 | 11/2015 |
| WO | WO 2015/184305 | 12/2015 |
| WO | WO 2015/191677 | 12/2015 |

OTHER PUBLICATIONS

Arunesh et al., "Small molecule inhibitors of PIM1 kinase: Jul. 2009 to Feb. 2013 patent update," Expert Opin Ther Pat, Jan. 2014, 24(1): 5-17.
Asano et al., "The serine/threonine kinase Pim-2 is a novel anti-apoptotic mediator in myeloma cells," Leukemia, 2011, 25: 1182-1188.
Bamborough, "Assessment of Chemical Coverage of Kinome Space and Its Implications for Kinase Drug Discovery," J. Med. Chem., 2008, 51: 7898-7914.
Baron et al., "PIM1 gene cooperates with human BCL6 gene to promote the development of lymphomas," PNAS, Apr. 2012, 109(15): 5735-5739.
Berge et al., "Pharmaceutical Salts," J. Pharm. Sci., 1977, 66(1):1-19.
Blanco-Aparicio, Biochemical Pharmacology, vol. 85, pp. 629-643, 2013.
Blom et al., "Optimizing Preparative LC-MS Configurations and Methods for Parallel Synthesis Purification," J. Comb. Chem., 2003, 5:670-83.
Blom et al., "Preparative LC-MS Purification: Improved Compound Specific Method Optimization," J. Comb. Chem., 2004, 6:874-883.
Blom, "Two-Pump At Column Dilution Configuration for Preparative Liquid Chromatography—Mass Spectrometry," J. Comb. Chem., 2002, 4:295-301.
Brault et al., "PIM kinases are progression markers and emerging therapeutic targets in diffuse large B-cell lymphoma," British Journal of Cancer, 2012, 107: 491-500.
Burger et al. "Structure Guided Optimization, in Vitro Activity, and in Vivo Activity of Pan-PIM Kinase Inhibitors," ACS Med Chem Lett., 2013, 4:1193-1197.
Caira, "Crystalline Polymorphism of Organic Compounds," Topics in Current Chemistry, Jan. 1998, 198: 163-208.
Cancer [online], [retrieved on Jul. 6, 2007] Retrieved from the Internet URL: http://www.nlm.nih.gov/medlineplus/cancer.html.
Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.
Chaichian "Targeted Therapies in Systemic Lupus Erythematosus: A State-of-the-Art-Review" J Clin Cell Immunol 2013, S6, 1-8.
Chan et al., "New N- and O-arylations with phenylboronic acids and cupric acetate," Tetrahedron Letters, May 1998, 39(19): 2933-2936.
Chen et al., "Mechanisms of cytotoxicity to Pim kinase inhibitor, SGI-1776, in acute myeloid leukemia," Blood, Jul. 2011, 118(3): 693-702.
Chen et al., "Pim kinase inhibitor, SGI-1776, induces apoptosis in chronic lymphocytic leukemia cells," Blood, 2009, 114:4150-57.
Chilean Office Action, Patent Application No. 1985-2015, dated Jul. 7, 2016, 22 pages (English Translation).
Chinese Office Action in Chinese Application No. 201480012783.3. dated Sep. 6, 2016, 16 pages (English Translation).
Claudio et al., "A molecular compendium of genes expressed in multiple myeloma," Blood, 2002, 100:2175-86.
Colombian Office Action in Colombian Application No. 15-168. 544, dated Aug. 10, 2016, 10 pages.
Coperet, "A simple and efficient method for the preparation of pyridine N-Oxides," The Journal of Organic Chemistry, Jan. 1998, 63: 1740-1741.
Damia "Contemporary pre-clinical development of anticancer agents—What are the optimal preclinical models?" European Journal of Cancer, 2009, 45, 2768-2781.
Database accession No. RN 1795440-67-3, Chemical Abstracts Service, Jul. 6, 2015, 1 page.
Davis et al., "Small Molecule Dual Antagonist of Pim 1 and 3 Kinases Ameliorate Experimental Autoimmune Encephalomyelitis," 26th Congress of the European Committee for Treatment and Research in Multiple Sclerosis, Oct. 13-16, 2010, Gothenburg, Sweden, Poster P436.
Dorwald F. A. Side Reactions in Organic Synthesis, 2005, Wiley: VCH, Weinheim p. IX of Preface p. 1-15.
Eurasian Office Action in Eurasian Application No. 201690458/28, dated Jan. 25, 2017, 11 pages (with English translation).
Freshney, Culture of Animal Cells, A Manual of Basic Technique, Alan R. Liss, Inc., 1983, New York, p. 4.
Fujii et al., "Aberrant expression of serine-threonine kinase Pim-3 in hepatocellular carcinoma development and its role in the proliferation of human hepatoma cell lines," Int. J. Canc., 2005, 114:209-18.
Georg Pilz, "Modern multiple sclerosis treatment—what is approved, what is on the horizon" Drug Discovery Today Dec. 2008, vol. 13, Nos. 23/24 1013-1025.
Golub et al., "Molecular Classification of Cancer: Class Discovery and Class Prediction by Gene Expression Monitoring," Science, 1999, 286: 531-537.
Gomez-Abad et al., "PIM2 inhibition as a rational therapeutic approach in B-cell lymphoma," Blood, 2011, 118:5517-27.
Gozgit et al., "Effects of the JAK2 Inhibitor, AZ960, on Pim/BAD/BCL-xL Survival Signaling in the Human JAK2 V617F Cell Line SET-2," Journal of Biological Chemistry, Nov. 2008, 283(47): 32334-32343.
Gu and Li, "A concise synthesis of (2S,4R)- and (2S,4S)-4-methylglutamic acid," Tetrahedron Lett., 2003, 44:3203-3205.
Hammerman et al., "Lymphocyte Transformation by Pim-2 Is Dependent on Nuclear Factor-kB Activation," Cancer Research, Nov. 2004, 64: 8341-8348.
Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-90.
Hsu et al., "Pim-1 knockdown potentiates paclitaxel-induced apoptosis in human hormone-refractory prostate cancers through inhibition of NHEJ DNA repair," Cancer Lett., 2012, 319:214-222.
Huang et al., "Structure-based design and optimization of 2-aminothiazole-4-carboxamide as a new class of CHK1 inhibitors," Bioorganic Med Chem Lett., Mar. 2013, 23(9):2590-2594.
International Preliminary Report on Patentability in International Application No. PCT/US2014/011486, dated Jul. 21, 2015, 7 pages.
International Preliminary Report on Patentability in International Application No. PCT/US2014/011487, dated Jul. 23, 2015, 6 pages.
International Preliminary Report on Patentability in International Application No. PCT/US2014/052214, dated Feb. 23, 2016, 7 pages.
International Preliminary Report on Patentability in International Application No. PCT/US2015/040146, dated Jan. 17, 2017, 8 pages.
International Search Report and Written Opinion in International Application No. PCT/US2014/011486, dated Mar. 17, 2014, 12 pages.
International Search Report and Written Opinion in International Application No. PCT/US2014/011487, dated Apr. 4, 2014, 11 pages.
International Search Report and Written Opinion in International Application No. PCT/US2014/052214, dated Oct. 28, 2014, 13 pages.
International Search Report and Written Opinion in International Application No. PCT/US2015/040146, dated Oct. 5, 2015, 12 pages.
International Search Report and Written Opinion in International Application No. PCT/US2016/034520, dated Jul. 12, 2016, 11 pages.
International Search Report and Written Opinion in International Application No. PCT/US2016/050925, dated Oct. 21, 2016, 13 pages.

(56) References Cited

OTHER PUBLICATIONS

International Search Report and Written Opinion in International Application No. PCT/US2016/054779, dated Dec. 9, 2016, 12 pages.
Isaac et al., "The oncogenic PIM kinase family regulates drug resistance through multiple mechanisms," Drug Resis. Updates, 2011, 14:203-11.
Ishchenko et al., "Structure-based design of low-nanomolar PIM kinase inhibitors," Bioorg Med Chem Lett., 2015, 25:474-480.
Jiang et al., "3,5-Disubstituted quinolines as novel c-Jun N-terminal kinase inhibitors," Bioorganic & Medicinal Chemistry Letters, 2007, 17: 6378-6382.
Johnson et al., "Relationship between drug activity in NCI preclinical in vitro and in vivo models and early clinical trials" British Journal of Cancer, 2001, 84, 1424-1437.
Katano et al., "Synthesis and biological activity of (cyclopentenopyridinium)thiomethylcephalosporins," The Journal of Antibiotics, Jan. 1990, 43(9): 1150-1159.
Kelly et al., "Targeting PIM kinase activity significantly augments the efficacy of cytarabine," British Journal of Haematology, 2011, 156, 129-152.
Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.
Lala et al., "Role of nitric oxide in tumor progression: Lessons from experimental tumors," Cancer and Metastasis Reviews, 1998, 17: 91-106.
Lam et al., "New aryl/heteroaryl C N bond cross-coupling reactions via arylboronic acid/cupric acetate arylation," Tetrahedron Letters, May 1998, 39(19): 2941-2944.
Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.
Liu et al., "Overexpression of Pim-1 is associated with poor prognosis in patients with esophageal squamous cell carcinoma," J. Surg. Oncol., 2010,102:683-88.
Liu et al., "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16: 2590-2594.
Lu et al., "Pim2 is required for maintaining multiple myeloma cell growth through modulating TSC2 phosphorylation," Blood, Aug. 2013, 122(9): 1610-1620.
Merkel et al., "PIM1 kinase as a target for cancer therapy," Exp. Opin. Investig. Drugs, 2012, 21:425-38.
Michelotti et al., "Two classes of p38a MAP kinase inhibitors having a common diphenylether core but exhbiting divergent binding modes," 2005, 15: 5274-5279.
Mikkers et al., "High-throughput retroviral tagging to identify components of specific signaling pathways in cancer," Nature Genet., 2002, 32:153-159.
Mikkers et al., "Mice deficient for all PIM kinases display reduced body size and impaired responses to hematopoietic growth factors," Mol. Cell. Biol., 2004, 24:6104-15.
Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorganic & Medicinal Chemistry Letters, 2007, 17: 250-254.
Mizuki et al., "Suppression of myeloid transcription factors and induction of STAT response genes by AML-specific Flt3 mutations," Blood, 2003, 101:3164-73.
Morwick, "Pim kinase inhibitors: a survey of the patent literature," Exp. Opin. Ther. Patents, 2010, 20(2):193-212.
Mulvihill et al., "Novel 2-phenylquinolin-7-yl-derived imidazo [1,5-a]pyrazines as potent insulin-like growth factor-I receptor (IFG-IR) inhibitors," Bioorganic & Medicinal Chemistry, 2008, 16: 1359-1375.

Ocana, A. "Preclinical development of molecular targeted agents for cancer" Nat. Rev. Clin. Oncol. 2011, 8, 200-209.
Ogawa et al., "Insights from Pim1 structure for anti-cancer drug design," Expert Opin Drug Discov, Dec. 2012, 7(12): 1177-92.
Peltola et al., "Pim-1 kinase expression predicts radiation response in squamocellular carcinoma of head and neck and is under the control of epidermal growth factor receptor," Neoplasia, 2009, 11:629-36.
Peturssion, "Protecting Groups in Carbohydrate Chemistry," J. Chem. Educ., 1997, 74(11):1297-1303.
Ravin, "Preformulation," Remington's Pharmaceutical Sciences, 17$^{th}$ Ed., (Mack Publishing Company, Easton, 1985), p. 1409-1423.
Robinson et al., "A Dual PIM 1/3 Kinase Inhibitor Demonstrates Efficacy in Murine Models of Lupus and Multiple Sclerosis," J. Immunol., 2012, 188:119.9.
Schatz, et al., "Targeting cap-dependent translation blocks converging survival signals by AKT and PIM kinases in lymphoma," J. Exp. Med., 2011, 208:1799-1807.
Schwemmers et al., "JAK2$^{V617F}$-negative ET Patients do not display constitutively active JAK/STAT signaling," Exp. Hematol., Nov. 2007, 35(11): 1695-1703.
Search Report, dated Jul. 2, 2014, 6 pages.
Search Report, dated Jul. 3, 2014, 4 pages.
Search Report, dated Jul. 8, 2014, 4 pages.
Sharma "Cell line-based platforms to evaluate the therapeutic efficacy of candidate anticancer agents" Nature Reviews Cancer Apr. 2010, vol. 10, 241-253.
Shen et al., "Inhibition of Pim-1 kinase ameliorates dextran sodium sulfate-induced colitis in mice," Dig. Dis. Sci., 2012, 57:1822-31.
Shinto et al., "Moloney murine leukemia virus infection accelerates lymphomagenesis in Eμ-bc1-2 transfenic mice," Oncogene, 1995, 11:1729-36.
Simone, Oncology: Introduction, Cecil Textbook of Medicine, 20th Edition, 1996 vol. 1, pp. 1004-1010.
Swords et al., "The Pim kinases: new targets for drug development," Curr. Drug Targets, 2011, 12(14):2059-66.
United States Office Action in U.S. Appl. No. 14/155,134, dated Jul. 27, 2015, 12 pages.
Venkatesh et al., "Role of the Development Scientist in Compound Lead Selection and Optimization," J. Pharm. Sci., 2000, 89:145-54.
Wang et al., "Inhibition of Pim1 kinase prevents peanut allergy by enhancing Runx3 expression and suppressing T(H)2 and T(H)17 T-cell differentiation," J. All. Clin. Immunol., 2012, 130:932-44.
www.leukaemia.org' [online]. "Myeloproliferative neoplasms (MPN)," 2016, [retrieved on Dec. 5, 2016]. Retrieved from the Internet: URL<http://www.leukaemia.org.au/blood-cancers/myeloproliferative-neoplasms-mpn>, 3 pages.
Yang et al., "Proviral integration site 2 is required for interleukin-6 expression induced by interleukin-1, tumour necrosis factor-α and lipopolysaccharide," Immunol., 2010, 131:174-182.
Zippo, et al., "PIM1-dependent phosphorylation of histone H3 at serine 10 is required for MYC-dependent transcriptional activation and oncogenic transformation," Nature Cell Biol., 2007, 9:932-44.
Chinese Office Action in Chinese Application No. 201480057613.7, dated Apr. 5, 2017, 15 pages (English Translation).
Guo et al., "Overexpression of Pim-1 in bladder cancer," J. Experimental & Clinical Cancer Research, 2010, 29: 161-167.
Hu et al., "PIM-1—specific mAb suppresses human and mouse tumor growth by decreasing PIM-1 levels, reducing Akt phosphorylation and activating apoptosis," J. Clinical Investigation, Feb. 2009, 119(2):362-375.
Jin et al., "Expressions of Osteopontin (OPN), anb3 an Pim-1 Associated with Poor Prognosis in Non-small Cell Lung Cancer (NSCLC)," Chin J. Cancer Res, 2012, 24(2): 103-108.
Lin et al., "A small molecule inhibitor of Pim protein kinases blocks the growth of precursor T-cell lymphoblastic leukemia/lymphoma," Blood, Jan. 2010, 115(4): 824-833.
Mahalingam et al., "Targeting PIM kinase enhances the activity of sunitinib in renal cell carcinoma," British J. Cancer, Oct. 2011, 105: 1563-1573.

(56) References Cited

OTHER PUBLICATIONS

Martin-Sanchez et al., "HDAC inhibitors induce cell cycle arrest, activate the apoptotic extrinsic pathway and synergize with a novel PIM inhibitor in Hodgkin lymphoma-derived cell lines," British J. Haematology, 2010, 152:347-362.

Mukaida et al., "Roles of Pim-3, a novel survival kinase, in tumorgenesis," Cancer Science, Aug. 2011, 102(8): 1437-1442.

Yan et al., "Clinical and therapeutic relevance of PIM1 kinase in gastric cancer," Gastric Cancer, 2012, 15:188-197.

Chilean Office Action in Chilean Application No. 1985-2015, dated Mar. 23, 2017, 13 pages (English Translation).

\* cited by examiner

BICYCLIC AROMATIC CARBOXAMIDE COMPOUNDS USEFUL AS PIM KINASE INHIBITORS

CROSS-REFERENCE TO RELATED APPLICATIONS

This application is a continuation application of and claims priority to U.S. patent application Ser. No. 14/797,765, filed on Jul. 13, 2015, which claims priority to U.S. Provisional Patent Application Ser. No. 62/024,333, filed on Jul. 14, 2014. Each application is incorporated herein by reference in its entirety.

TECHNICAL FIELD

The present application is concerned with pharmaceutically useful compounds. The disclosure provides new compounds as well as their compositions and methods of use. The compounds inhibit the activity of Pim kinases and are therefore useful in the treatment of diseases related to the activity of Pim kinases including, e.g., cancers and other diseases.

BACKGROUND

Protein kinases regulate diverse biological processes including cell growth, survival, differentiation, organ formation, morphogenesis, neovascularization, tissue repair, and regeneration, among others. Protein kinases also play specialized roles in a host of human diseases including cancer. The three members of the Pim kinase family, one example of a protein kinase family, were initially identified as preferential integration sites of Moloney leukemia virus in mouse models of cancer. Although possessing modest but measurable oncogenic activity alone, they potentiate pro-proliferative and pro-survival oncogenes, e.g., causing a dramatic acceleration of lymphomagenesis in Myc-transgenic or Bcl2-transgenic mice. Mikkers et al., *Nature Genet.*, 2002, 32, 153-159; Shinto et al., *Oncogene*, 1995, 11, 1729-35.

The three non-receptor serine/threonine kinases Pim1, Pim2 and Pim3 regulate cell proliferation and survival by impacting gene transcription and protein translation. Zippo, et al., *Nature Cell Biol.*, 2007, 9, 932-44; Schatz, et al., *J Exp. Med.*, 2011, 208, 1799-1807. As opposed to numerous other protein kinases which require activation by phosphorylation, the Pim kinases are constitutively activated and family members have overlapping substrate targets and biological functions, with differences between family members dictated, in part, by their varied tissue distribution. Expression of the Pim kinases is induced by cytokines and growth factors. Among the cytokines activating Pim kinase expression are cytokines which signal through the JAK/STAT pathway. Pim kinases act in parallel to the PI3K/AKT pathway, and they share several phosphorylation targets (e.g., pBAD, p4EBP1). Inhibitors of Pim kinases may therefore potentiate regimens including inhibitors of either the JAK pathway or the PI3K/AKT pathway.

Overexpression of Pim kinases is detected in a wide variety of hematologic and solid cancers. Overexpression of various family members have been noted in multiple myeloma, A ML, pancreatic and hepatocellular cancers. Claudio et al., *Blood*, 2002, 100, 2175-86; Amson et al., *Proc. Nat. Acad. Sci., USA*, 1989, 86, 8857-61; Mizuki et al., *Blood*, 2003, 101, 3164-73; Li et al., *Canc. Res.*, 2006, 66, 6741-7; Fujii et al., *Int. J. Canc.*, 2005, 114, 209-18. Pim1 overexpression is associated with poor prognosis in mantle cell lymphoma, esophageal and head and neck cancers. Hsi et al., *Leuk. Lymph.*, 2008, 49, 2081-90; Liu et al., *J. Surg. Oncol.*, 2010, 102, 683-88; Peltola et al., *Neoplasia*, 2009, 11, 629-36. Pim2 overexpression is associated with an aggressive clinical course in a subset of DLBCL patients. Gomez-Abad et al., *Blood*, 2011, 118, 5517-27. Overexpression is often seen where Myc is overexpressed and Pim kinases can convey resistance to traditional chemotherapeutic agents and radiation. Chen et al., *Blood*, 2009, 114, 4150-57; Isaac et al., *Drug Resis. Updates*, 2011, 14, 203-11; Hsu et al., *Cancer Lett.*, 2012, 319, 214; Peltola et al., *Neoplasia*, 2009, 11, 629-36.

As such, these data indicate that inhibition of Pim kinases will be useful to provide therapeutic benefit in cancer patients.

Data from mice deficient for one or multiple Pim kinase family members suggests that pan-Pim inhibitor would have a favorable toxicity profile. Triple knockout mice are viable, but are slightly smaller than their wild type littermates. Mikkers et al., *Mol. Cell. Biol.*, 2004, 24. 6104-15. Since Pim kinases are also involved in a variety of immunologic and inflammatory responses and these indications require drug agents with fewer side effects, Pim kinase inhibitors are expected to be useful in treating patients with colitis (Shen et al., *Dig. Dis. Sci.*, 2012, 57, 1822-31), peanut allergy (Wang et al., *J. All. Clin. Immunol.*, 2012, 130, 932-44), multiple sclerosis and lupus (Davis et al., "Small Molecule Dual Antagonist of Pim 1 and 3 Kinases Ameliorate Experimental Autoimmune Encephalomyelitis", 26th Congress of the European Committee for Treatment and Research in Multiple Sclerosis, 13-16 Oct. 2010, Gothenburg, Sweden, Poster P436; Robinson et al., *J. Immunol.*, 2012, 188, 119.9) and rheumatoid arthritis (Yang et al., *Immunol.* 2010, 131, 174-182) and other immunological and inflammatory disorders.

The Pim kinases have therefore been identified as useful targets for drug development efforts. Swords et al., *Curr. Drug Targets*, 2011, 12(14), 2059-66; Merkel et al., *Exp. Opin. Investig. Drugs*, 2012, 21, 425-38; Morwick et al., *Exp. Opin. Ther. Patents*, 2010, 20(2), 193-212.

Accordingly, there is a need for new compounds that inhibit Pim kinases. The present application describes new inhibitors of Pim kinases that are useful for treating diseases associated with the expression or activity of one or more Pim kinases, e.g., cancer and other diseases.

SUMMARY

The present disclosure provides, inter alia, a compound of Formula (I):

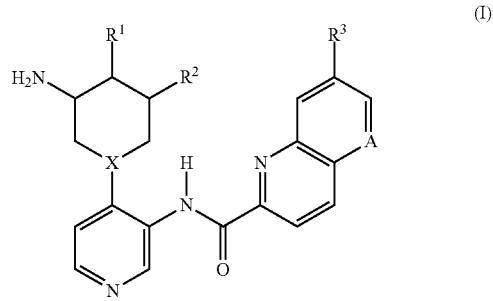

or a pharmaceutically acceptable salt thereof; wherein the variables are as defined below.

The present disclosure also provides a composition comprising a compound of Formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of Formula (I), or a pharmaceutically acceptable salt thereof.

The details of one or more embodiments are set forth in the description below. Other features, objects and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

I. Compounds

The present disclosure provides, inter alia, a compound of Formula (I):

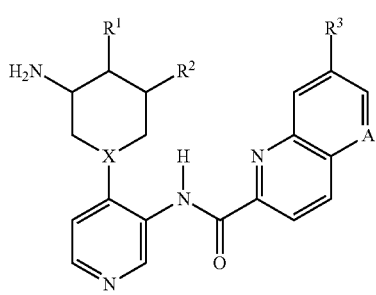

(I)

or a pharmaceutically acceptable salt thereof, wherein:
X is N or CH;
$R^1$ is H or OH;
$R^2$ is $C_{1-6}$ alkyl, $C_{1-3}$ haloalkyl or $C_{3-7}$ cycloalkyl;
A is N or CH; and
$R^3$ is H, halogen, $C_{1-6}$ alkyl, $C_{2-6}$ alkenyl, $C_{2-6}$ alkynyl, $C_{1-6}$ haloalkyl, Cy, -L-Cy, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$ or $S(O)_2NR^{c1}R^{d1}$, wherein said $C_{1-6}$ alkyl, $C_{2-6}$ alkenyl or $C_{2-6}$ alkynyl forming $R^3$ are each independently unsubstituted or substituted with 1, 2 or 3 substituents independently selected from halogen, $C_{1-3}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$;

Cy is unsubstituted or substituted $C_{6-10}$ aryl, unsubstituted or substituted 5-10 membered heteroaryl, unsubstituted or substituted $C_{3-6}$ cycloalkyl or unsubstituted or substituted 4-11 membered heterocycloalkyl, wherein the substituted $C_{6-10}$ aryl, 5-10 memberedheteroaryl, $C_{3-6}$ cycloalkyl or 4-11 membered heterocycloalkyl forming Cy is substituted with 1, 2, 3, 4 or 5 substituents each independently selected from halogen, $R^{Cy1}$, $R^{Cy2}$, $C_{2-6}$ alkenyl, $C_{2-6}$ alkynyl, $C_{1-6}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$, wherein each $R^{Cy1}$ is, independently, $C_{1-6}$ alkyl, each of which is independently unsubstituted or substituted with 1, 2 or 3 substituents independently selected from halogen, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$ $NR^{c1}S(O)_2R^{b1}$ and $S(O)_2NR^{c1}R^{d1}$; or wherein each $R^{Cy2}$ is, independently, $C_{6-10}$ aryl, $C_{3-7}$ cycloalkyl, 5-10 membered heteroaryl, or 4-7 membered heterocycloalkyl, each of which is independently unsubstituted or substituted with 1, 2 or 3 substituents independently selected from halogen, $C_{1-6}$ alkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$ $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$ $NR^{c1}S(O)_2R^{b1}$ and $S(O)_2NR^{c1}R^{d1}$;

L is unsubstituted $C_{1-6}$ alkylene or $C_{1-6}$ alkylene substituted with 1, 2 or 3 substituents independently selected from F, Cl, CN, OH, $O(C_{1-6}$ alkyl), $NH_2$, $NH(C_{1-6}$ alkyl) and $N(C_{1-6}$ alkyl)$_2$;

$R^{a1}$, $R^{b1}$, $R^{c1}$ and $R^{d1}$, at each occurrence, are independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl groups forming $R^{a1}$, $R^{b1}$, $R^{c1}$ and $R^{d1}$ are each optionally substituted with 1, 2, 3, 4 or 5 substituents independently selected from $C_{1-6}$ alkyl, $R^{Cy3}$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ and $S(O)_2NR^{c2}R^{d2}$;

or $R^{c1}$ and $R^{d1}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ and $S(O)_2NR^{c2}R^{d2}$;

wherein each $R^{Cy3}$ is, independently, phenyl, $C_{3-7}$ cycloalkyl, 5-6 membered heteroaryl, or 4-7 membered heterocycloalkyl, each of which is independently unsubstituted or substituted with 1, 2 or 3 substituents independently selected from halogen, $C_{1-6}$ alkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$ $NR^{c2}S(O)_2R^{b2}$ and $S(O)_2NR^{c2}R^{d2}$; and $R^{a2}$, $R^{b2}$, $R^{c2}$ and $R^{d2}$ are each independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{1-6}$ haloalkyl, $C_{2-6}$ alkenyl, and $C_{2-6}$ alkynyl forming $R^{a2}$, $R^{b2}$, $R^{c2}$ and $R^{d2}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy.

In some embodiments, the compound of Formula (I), or a pharmaceutically acceptable salt thereof, can be a compound according to Formula (II):

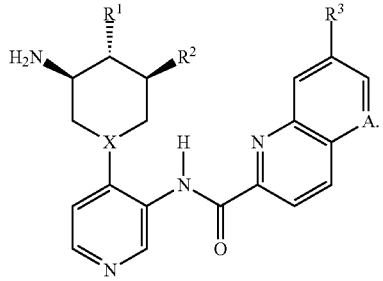
(II)

In some embodiments, X is N.

In some embodiments, X is CH.

In some embodiments, $R^1$ is OH.

In some embodiments, $R^1$ is H.

In some embodiments, $R^2$ is $C_{1-6}$ alkyl.

In some embodiments, $R^2$ is $C_{1-3}$ alkyl.

In some embodiments, $R^2$ is methyl.

In some embodiments, $R^2$ is $C_{1-3}$ haloalkyl, e.g., $CF_3$.

In some embodiments, $R^2$ is $C_{3-7}$ cycloalkyl.

In some embodiments, $R^2$ is cyclopropyl.

In some embodiments, A is N.

In some embodiments, A is CH.

In some embodiments, the compound of Formula (I), or a pharmaceutically acceptable salt thereof, is of any one of the following Formulae (III) to (VIII):

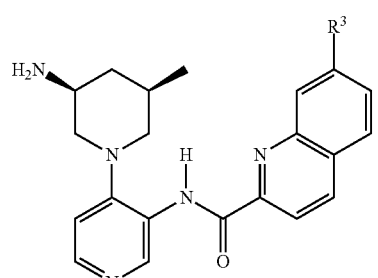
(III)

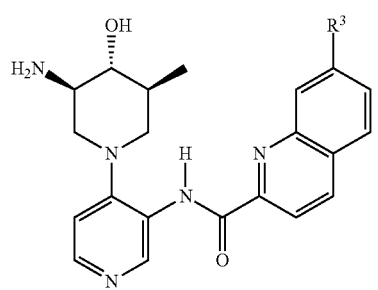
(IV)

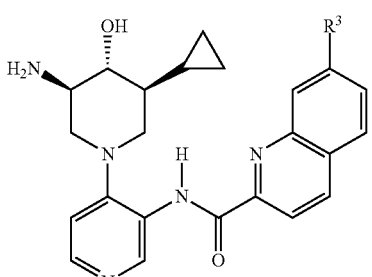
(V)

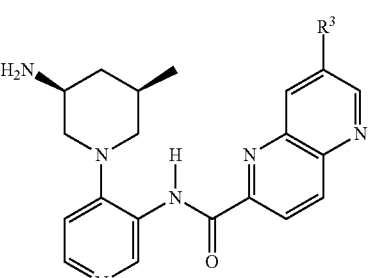
(VI)

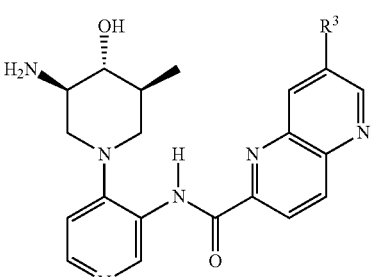
(VII)

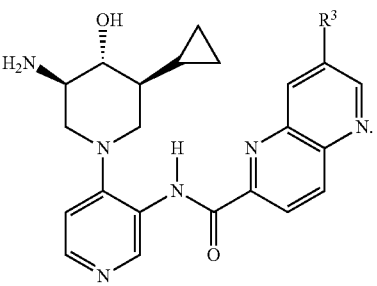
(VIII)

In some embodiments, $R^3$ is $C_{1-6}$ alkyl, Cy or -L-Cy, wherein the $C_{1-6}$ alkyl forming $R^3$ is unsubstituted or substituted with 1, 2 or 3 substituents independently selected from halogen, $C_{1-3}$ haloalkyl, CN, and $OR^{a1}$.

In some embodiments, $R^3$ is $C_{1-6}$ alkyl, Cy, or -L-Cy, wherein Cy is unsubstituted or substituted $C_{6-10}$ aryl, unsubstituted or substituted 5-10 membered heteroaryl, unsubstituted or substituted $C_{3-6}$ cycloalkyl or unsubstituted or substituted 4-11 membered heterocycloalkyl, wherein the substituted $C_{6-10}$ aryl, 5-10 memberedheteroaryl, $C_{3-6}$ cycloalkyl or 4-11 membered heterocycloalkyl forming Cy is substituted with 1, 2, or 3 substituents each independently selected from halogen, $R^{Cy1}$, $R^{Cy2}$, $C_{1-6}$ haloalkyl, CN, OH, and $C_{1-6}$ alkoxy, wherein each $R^{Cy1}$ is, independently, $C_{1-6}$ alkyl, each of which is independently unsubstituted or substituted with 1, 2 or 3 substituents independently selected from halogen, CN, $OR^{a1}$, wherein each $R^{Cy2}$ is, independently, $C_{6-10}$ aryl, $C_{3-7}$ cycloalkyl, 5-10 membered heteroaryl, or 4-7 membered heterocycloalkyl, each of which is independently unsubstituted or substituted with 1, 2 or 3 substituents independently selected from halogen, $C_{1-6}$ alkyl, CN and $OR^{a1}$, and wherein $R^{a1}$ is independently, at each occurrence, selected from H, $C_{1-6}$ alkyl, $C_{2-6}$ alkenyl, and $C_{2-6}$ alkynyl.

In some embodiments, $R^3$ is $C_{1-6}$ alkyl, Cy, or -L-Cy, wherein Cy is unsubstituted or substituted $C_{6-10}$ aryl, unsubstituted or substituted 5-10 membered heteroaryl, unsubstituted or substituted $C_{3-6}$ cycloalkyl or unsubstituted or substituted 4-11 membered heterocycloalkyl, wherein the substituted $C_{6-10}$ aryl, 5-10 memberedheteroaryl, $C_{3-6}$ cycloalkyl or 4-11 membered heterocycloalkyl forming Cy is substituted with 1, 2, or 3 substituents each independently selected from halogen, $R^{Cy1}$, $C_{6-10}$ aryl, $C_{3-7}$ cycloalkyl, 5-10 membered heteroaryl or 4-7 membered heterocycloalkyl, $C_{1-6}$ haloalkyl, CN, OH, and $C_{1-6}$ alkoxy, wherein each $R^{Cy1}$ is, independently, $C_{1-6}$ alkyl, each of which is independently unsubstituted or substituted with 1, 2 or 3 substituents independently selected from halogen, CN, and $OR^{a1}$, and wherein $R^{a1}$ is independently, at each occurrence, selected from H, $C_{1-6}$ alkyl, $C_{2-6}$ alkenyl, and $C_{2-6}$ alkynyl.

In some embodiments, $R^3$ is $C_{1-6}$ alkyl.
In some embodiments, $R^3$ is ethyl or isopropyl.
In some embodiments, $R^3$ is Cy.
In some embodiments, $R^3$ is -L-Cy.
In some embodiments, Cy is unsubstituted or substituted $C_{6-10}$ aryl.
In some embodiments, Cy is unsubstituted phenyl.
In some embodiments, Cy is substituted phenyl.
In some embodiments, Cy is phenyl substituted with 1, 2, or 3 substituents.
In some embodiments, Cy is phenyl substituted with 1, 2, or 3 substituents independently selected from halogen, CN, and $OR^{a1}$.
In some embodiments, Cy is phenyl substituted with 1, 2, or 3 substituents independently selected from fluoro, CN, and OH.
In some embodiments, Cy is 2-cyanophenyl, 2,6-difluorophenyl or 2,6-difluoro-4-methoxyphenyl.
In some embodiments, Cy is unsubstituted or substituted 5-10 membered heteroaryl.
In some embodiments, Cy is unsubstituted or substituted 5-10 membered heteroaryl, the ring atoms of which consist of carbon atoms and 1 or 2 nitrogen atoms.
In some embodiments, Cy is unsubstituted or substituted pyridinyl or pyrazolyl.
In some embodiments, Cy is unsubstituted pyridinyl.
In some embodiments, Cy is pyridinyl substituted with 1 substituent selected from $R^{Cy2}$ and $OR^{a1}$.
In some embodiments, Cy is 6-(morpholin-4-yl)pyridin-3-yl or 6-methoxypyridin-3-yl.
In some embodiments, Cy is pyrazolyl substituted with a $C_{1-6}$ alkyl group.
In some embodiments, Cy is 1-methyl-1H-pyrazol-4-yl or 1-ethyl-1H-pyrazol-4-yl.
In some embodiments, Cy is unsubstituted or substituted $C_{3-6}$ cycloalkyl.
In some embodiments, Cy is unsubstituted or substituted 4-11 membered heterocycloalkyl.
In some embodiments, Cy is unsubstituted or substituted heterocycloalkyl, the ring atoms of which consist of carbon atoms and 1, 2, or 3 heteroatoms independently selected from N and O.
In some embodiments, Cy is unsubstituted or substituted heterocycloalkyl, the ring atoms or which consist of carbon atoms and 1 or 2 nitrogen atoms.

In some embodiments, Cy is unsubstituted or substituted heterocycloalkyl, the ring atoms of which consist of carbon atoms, 1 oxygen atom and 1 nitrogen atom.
In some embodiments, a nitrogen atom of Cy forms the bond between Cy and the remainder of the molecule.
In some embodiments, Cy is unsubstituted or substituted pyrrolidinyl, piperidinyl, azetidinyl, piperazinyl or oxopiperazinyl.
In some embodiments, Cy is unsubstituted pyrrolidin-1-yl.
In some embodiments, Cy is pyrrolidin-1-yl substituted with a $C_{1-6}$ haloalkyl group.
In some embodiments, Cy is 3-(trifluoromethyl)pyrrolidin-1-yl.
In some embodiments, Cy is unsubstituted piperidin-1-yl.
In some embodiments, Cy is substituted piperidin-1-yl substituted at the 4-position.
In some embodiments, Cy is substituted piperidin-1-yl substituted at the 4-position by 1 substituent.
In some embodiments, Cy is substituted piperidin-1-yl substituted by 1 substituent selected from $R^{Cy2}$, CN, and $OR^a$.
In some embodiments, Cy is 4-hydroxypiperidin-1-yl, 4-cyanopiperidin-1-yl, 4-methoxypiperidin-1-yl, 4-(pyridin-4-yl)piperidin-1-yl, or 4-(morpholin-4-yl)piperidin-1-yl.
In some embodiments, Cy is unsubstituted azetidin-1-yl.
In some embodiments, Cy is azetidin-1-yl substituted with two $C_{1-6}$ alkyl groups.
In some embodiments, Cy is 3,3-dimethylazetidin-1-yl.
In some embodiments, Cy is unsubstituted or substituted piperazin-1-yl.
In some embodiments, Cy is 4-substituted piperazin-1-yl.
In some embodiments, Cy is a piperazin-1-yl substituted with at least one $C_{1-6}$ alkyl.
In some embodiments, Cy is piperazin-1-yl substituted only at the 4-position.
In some embodiments, Cy is piperazin-1-yl substituted only at the 4-position and wherein the 4-substituent is $C_{1-6}$ alkyl.
In some embodiments, Cy is 4-methylpiperazin-1-yl or 4-ethylpiperazin-1-yl.
In some embodiments, Cy is unsubstituted or substituted oxopiperazinyl.
In some embodiments, Cy is unsubstituted or substituted 3-oxopiperazin-1-yl.
In some embodiments, Cy is 3-oxopiperazin-1-yl substituted only at the 4-position and wherein the 4-substituent is $C_{1-6}$ alkyl.
In some embodiments, Cy is 4-methyl-3-oxopiperazin-1-yl or 4-ethyl-3-oxopiperazin-1-yl.
In some embodiments, Cy is unsubstituted or substituted 3-oxa-9-azaspiro[5.5]undecanyl, 1-oxa-8-azaspiro[4.5]decanyl, or morpholinyl.
In some embodiments, Cy is unsubstituted 3-oxa-9-azaspiro[5.5]undecan-9-yl, 1-oxa-8-azaspiro[4.5]decan-8-yl or morpholin-4-yl.
In some embodiments, Cy is unsubstituted or substituted heterocycloalkyl, the ring atoms of which consist of carbon atoms and 1 oxygen atom.
In some embodiments, Cy is unsubstituted or substituted tetrahydro-2H-pyranyl.
In some embodiments, Cy is unsubstituted tetrahydro-2H-pyran-4-yl.
In some embodiments, L is unsubstituted $C_{1-6}$ alkylene or $C_{1-6}$ alkylene substituted with 1, 2 or 3 substituents independently selected from F, Cl, CN, OH and $O(C_{1-6}$ alkyl).
In some embodiments, L is unsubstituted $C_{1-6}$ alkylene.

In some embodiments, L is $C_{1-3}$ alkylene.
In some embodiments, L is $C_{1-2}$ alkylene.
In some embodiments, L is $CH_2$.
In some embodiments, each $R^{Cy1}$ is $C_{1-6}$ alkyl.
In some embodiments, each $R^{Cy1}$ is methyl or ethyl.
In some embodiments, each $R^{Cy2}$ is 4 to 7 membered heterocycloalkyl.
In some embodiments, $R^{a1}$, $R^{b1}$, $R^{c1}$, $R^{d1}$, $R^{a2}$, $R^{b2}$, $R^{c2}$, and $R^{d2}$ are each independently selected from H and $C_{1-6}$ alkyl.
In some embodiments, $R^{a1}$, $R^{b1}$, $R^{c1}$, $R^{d1}$, $R^{a2}$, $R^{b2}$, $R^{c2}$, and $R^{d2}$ are each independently selected from H and methyl.

The compounds of Formula (I) include the following compounds, and pharmaceutically acceptable salts thereof:

N-{4-[3-amino-5-methylpiperidin-1-yl]pyridin-3-yl}-7-(2,6-difluorophenyl)-1,5-naphthyridine-2-carboxamide;
N-{4-[3-amino-5-methylpiperidin-1-yl]pyridin-3-yl}-7-isopropyl-1,5-naphthyridine-2-carboxamide;
N-{4-[3-amino-5-methylpiperidin-1-yl]pyridin-3-yl}-7-(tetrahydro-2H-pyran-4-yl)-1,5-naphthyridine-2-carboxamide;
N-{4-[3-amino-5-methylpiperidin-1-yl]pyridin-3-yl}-7-(2,6-difluoro-4-methoxyphenyl)-1,5-naphthyridine-2-carboxamide;
N-{4-[3-amino-5-methylpiperidin-1-yl]pyridin-3-yl}-7-(1-ethyl-1H-pyrazol-4-yl)-1,5-naphthyridine-2-carboxamide;
N-{4-[3-amino-4-hydroxy-5-methylpiperidin-1-yl]pyridin-3-yl}-7-isopropenyl-1,5-naphthyridine-2-carboxamide;
N-{4-[3-amino-4-hydroxy-5-methylpiperidin-1-yl]pyridin-3-yl}-7-(6-methoxypyridin-3-yl)-1,5-naphthyridine-2-carboxamide;
N-{4-[3-amino-4-hydroxy-5-methylpiperidin-1-yl]pyridin-3-yl}-7-morpholin-4-yl-1,5-naphthyridine-2-carboxamide;
N-{4-[3-amino-4-hydroxy-5-methylpiperidin-1-yl]pyridin-3-yl}-7-ethylquinoline-2-carboxamide;
N-{4-[3-amino-4-hydroxy-5-methylpiperidin-1-yl]pyridin-3-yl}-7-isopropylquinoline-2-carboxamide;
N-{4-[3-amino-4-hydroxy-5-methylpiperidin-1-yl]pyridin-3-yl}-7-(tetrahydro-2H-pyran-4-yl)quinoline-2-carboxamide;
N-{4-[3-amino-4-hydroxy-5-methylpiperidin-1-yl]pyridin-3-yl}-7-morpholin-4-ylquinoline-2-carboxamide;
N-{4-[3-amino-5-methylpiperidin-1-yl]pyridin-3-yl}-7-morpholin-4-ylquinoline-2-carboxamide;
N-{4-[3-amino-4-hydroxy-5-methylpiperidin-1-yl]pyridin-3-yl}-7-(3-oxa-9-azaspiro[5.5]undec-9-yl)quinoline-2-carboxamide;
N-{4-[3-amino-5-methylpiperidin-1-yl]pyridin-3-yl}-7-(3-oxa-9-azaspiro[5.5]undec-9-yl)quinoline-2-carboxamide;
N-{4-[3-amino-4-hydroxy-5-methylpiperidin-1-yl]pyridin-3-yl}-7-(4-cyanopiperidin-1-yl)quinoline-2-carboxamide;
N-{4-[3-amino-5-methylpiperidin-1-yl]pyridin-3-yl}-7-(4-cyanopiperidin-1-yl)quinoline-2-carboxamide;
N-{4-[3-amino-4-hydroxy-5-methylpiperidin-1-yl]pyridin-3-yl}-7-(4-methylpiperazin-1-yl)quinoline-2-carboxamide;
N-{4-[3-amino-5-methylpiperidin-1-yl]pyridin-3-yl}-7-(4-methylpiperazin-1-yl)quinoline-2-carboxamide;
N-{4-[3-amino-4-hydroxy-5-methylpiperidin-1-yl]pyridin-3-yl}-7-(4-pyridin-4-ylpiperidin-1-yl)quinoline-2-carboxamide;
N-{4-[3-amino-5-methylpiperidin-1-yl]pyridin-3-yl}-7-(4-pyridin-4-ylpiperidin-1-yl)quinoline-2-carboxamide;
N-{4-[3-amino-4-hydroxy-5-methylpiperidin-1-yl]pyridin-3-yl}-7-(4-ethyl-3-oxopiperazin-1-yl)quinoline-2-carboxamide;
N-{4-[3-amino-5-methylpiperidin-1-yl]pyridin-3-yl}-7-(4-ethyl-3-oxopiperazin-1-yl)quinoline-2-carboxamide;
N-{4-[3-amino-4-hydroxy-5-methylpiperidin-1-yl]pyridin-3-yl}-7-(4-methoxypiperidin-1-yl)quinoline-2-carboxamide;
N-{4-[3-amino-5-methylpiperidin-1-yl]pyridin-3-yl}-7-(4-methoxypiperidin-1-yl)quinoline-2-carboxamide;
N-{4-[3-amino-4-hydroxy-5-methylpiperidin-1-yl]pyridin-3-yl}-7-(4-morpholin-4-ylpiperidin-1-yl)quinoline-2-carboxamide;
N-{4-[3-amino-5-methylpiperidin-1-yl]pyridin-3-yl}-7-(4-morpholin-4-ylpiperidin-1-yl)quinoline-2-carboxamide;
N-{4-[3-amino-4-hydroxy-5-methylpiperidin-1-yl]pyridin-3-yl}-7-[3-(trifluoromethyl)pyrrolidin-1-yl]quinoline-2-carboxamide;
N-{4-[3-amino-5-methylpiperidin-1-yl]pyridin-3-yl}-7-[3-(trifluoromethyl)pyrrolidin-1-yl]quinoline-2-carboxamide;
N-{4-[3-amino-4-hydroxy-5-methylpiperidin-1-yl]pyridin-3-yl}-7-pyrrolidin-1-ylquinoline-2-carboxamide;
N-{4-[3-amino-5-methylpiperidin-1-yl]pyridin-3-yl}-7-pyrrolidin-1-ylquinoline-2-carboxamide;
N-{4-[3-amino-4-hydroxy-5-methylpiperidin-1-yl]pyridin-3-yl}-7-(3,3-dimethylazetidin-1-yl)quinoline-2-carboxamide;
N-{4-[3-amino-5-methylpiperidin-1-yl]pyridin-3-yl}-7-(3,3-dimethylazetidin-1-yl)quinoline-2-carboxamide;
N-{4-[3-amino-5-methylpiperidin-1-yl]pyridin-3-yl}-7-azetidin-1-ylquinoline-2-carboxamide;
N-{4-[3-amino-5-cyclopropyl-4-hydroxypiperidin-1-yl]pyridin-3-yl}-7-(2,6-difluoro-4-methoxyphenyl)-1,5-naphthyridine-2-carboxamide;
N-{4-[3-amino-5-cyclopropyl-4-hydroxypiperidin-1-yl]pyridin-3-yl}-7-(6-methoxypyridin-3-yl)-1,5-naphthyridine-2-carboxamide;
N-{4-[3-amino-5-cyclopropyl-4-hydroxypiperidin-1-yl]pyridin-3-yl}-7-(6-morpholin-4-ylpyridin-3-yl)-1,5-naphthyridine-2-carboxamide;
N-{4-[3-amino-5-cyclopropyl-4-hydroxypiperidin-1-yl]pyridin-3-yl}-7-(1-ethyl-1H-pyrazol-4-yl)-1,5-naphthyridine-2-carboxamide;
N-{4-[3-amino-5-cyclopropyl-4-hydroxypiperidin-1-yl]pyridin-3-yl}-7-(1-methyl-1H-pyrazol-4-yl)-1,5-naphthyridine-2-carboxamide;
N-{4-[3-amino-5-cyclopropyl-4-hydroxypiperidin-1-yl]pyridin-3-yl}-7-(3-oxa-9-azaspiro[5.5]undec-9-yl)-1,5-naphthyridine-2-carboxamide;
N-{4-[3-amino-5-cyclopropyl-4-hydroxypiperidin-1-yl]pyridin-3-yl}-7-(4-cyanopiperidin-1-yl)-1,5-naphthyridine-2-carboxamide;
N-{4-[3-amino-5-cyclopropyl-4-hydroxypiperidin-1-yl]pyridin-3-yl}-7-(1-oxa-8-azaspiro[4.5]dec-8-yl)-1,5-naphthyridine-2-carboxamide;
N-{4-[3-amino-4-hydroxy-5-methylpiperidin-1-yl]pyridin-3-yl}-7-(1-methyl-1H-pyrazol-4-yl)quinoline-2-carboxamide;
N-{4-[3-amino-4-hydroxy-5-methylpiperidin-1-yl]pyridin-3-yl}-7-(1-ethyl-1H-pyrazol-4-yl)quinoline-2-carboxamide;
N-{4-[3-amino-4-hydroxy-5-methylpiperidin-1-yl]pyridin-3-yl}-7-(6-methoxypyridin-3-yl)quinoline-2-carboxamide;

N-{4-[3-amino-4-hydroxy-5-methylpiperidin-1-yl]pyridin-3-yl}-7-(6-morpholin-4-ylpyridin-3-yl)quinoline-2-carboxamide;

N-(4-(3-amino-4-hydroxy-5-methylpiperidin-1-yl)pyridin-3-yl)-7-(pyridin-3-yl)quinoline-2-carboxamide;

N-{4-[3-amino-5-methylpiperidin-1-yl]pyridin-3-yl}-7-(1-methyl-1H-pyrazol-4-yl)quinoline-2-carboxamide;

N-{4-[3-amino-5-methylpiperidin-1-yl]pyridin-3-yl}-7-(2-cyanophenyl)quinoline-2-carboxamide;

N-(4-(3-amino-5-methylpiperidin-1-yl)pyridin-3-yl)-7-(4-hydroxypiperidin-1-yl)quinoline-2-carboxamide;

N-{4-[3-amino-5-(trifluoromethyl)piperidin-1-yl]pyridin-3-yl}-7-(2-cyanophenyl)-1,5-naphthyridine-2-carboxamide; and N-{4-[3-amino-4-hydroxy-5-methylpiperidin-1-yl]pyridin-3-yl}-7-[6-(tetrahydro-2H-pyran-4-yloxy)pyridin-3-yl]quinoline-2-carboxamide.

The compounds of Formula (I) include the following compounds, and pharmaceutically acceptable salts thereof:

N-{4-[(3S,5R)-3-amino-5-methylpiperidin-1-yl]pyridin-3-yl}-7-(2,6-difluorophenyl)-1,5-naphthyridine-2-carboxamide;

N-{4-[(3S,5R)-3-amino-5-methylpiperidin-1-yl]pyridin-3-yl}-7-isopropyl-1,5-naphthyridine-2-carboxamide;

N-{4-[(3S,5R)-3-amino-5-methylpiperidin-1-yl]pyridin-3-yl}-7-(tetrahydro-2H-pyran-4-yl)-1,5-naphthyridine-2-carboxamide;

N-{4-[(3S,5R)-3-amino-5-methylpiperidin-1-yl]pyridin-3-yl}-7-(2, 6-difluoro-4-methoxyphenyl)-1,5-naphthyridine-2-carboxamide;

N-{4-[(3S,5R)-3-amino-5-methylpiperidin-1-yl]pyridin-3-yl}-7-(1-ethyl-1H-pyrazol-4-yl)-1,5-naphthyridine-2-carboxamide;

N-{4-[(3R,4R,5S)-3-amino-4-hydroxy-5-methylpiperidin-1-yl]pyridin-3-yl}-7-isopropenyl-1,5-naphthyridine-2-carboxamide;

N-{4-[(3R,4R,5S)-3-amino-4-hydroxy-5-methylpiperidin-1-yl]pyridin-3-yl}-7-(6-methoxypyridin-3-yl)-1,5-naphthyridine-2-carboxamide;

N-{4-[(3R,4R,5S)-3-amino-4-hydroxy-5-methylpiperidin-1-yl]pyridin-3-yl}-7-morpholin-4-yl-1,5-naphthyridine-2-carboxamide;

N-{4-[(3R,4R,5S)-3-amino-4-hydroxy-5-methylpiperidin-1-yl]pyridin-3-yl}-7-ethylquinoline-2-carboxamide;

N-{4-[(3R,4R,5S)-3-amino-4-hydroxy-5-methylpiperidin-1-yl]pyridin-3-yl}-7-isopropylquinoline-2-carboxamide;

N-{4-[(3R,4R,5S)-3-amino-4-hydroxy-5-methylpiperidin-1-yl]pyridin-3-yl}-7-(tetrahydro-2H-pyran-4-yl)quinoline-2-carboxamide;

N-{4-[(3R,4R,5S)-3-amino-4-hydroxy-5-methylpiperidin-1-yl]pyridin-3-yl}-7-morpholin-4-ylquinoline-2-carboxamide;

N-{4-[(3S,5R)-3-amino-5-methylpiperidin-1-yl]pyridin-3-yl}-7-morpholin-4-ylquinoline-2-carboxamide;

N-{4-[(3R,4R,5S)-3-amino-4-hydroxy-5-methylpiperidin-1-yl]pyridin-3-yl}-7-(3-oxa-9-azaspiro[5.5]undec-9-yl)quinoline-2-carboxamide;

N-{4-[(3S,5R)-3-amino-5-methylpiperidin-1-yl]pyridin-3-yl}-7-(3-oxa-9-azaspiro[5.5]undec-9-yl)quinoline-2-carboxamide;

N-{4-[(3R,4R,5S)-3-amino-4-hydroxy-5-methylpiperidin-1-yl]pyridin-3-yl}-7-(4-cyanopiperidin-1-yl)quinoline-2-carboxamide;

N-{4-[(3S,5R)-3-amino-5-methylpiperidin-1-yl]pyridin-3-yl}-7-(4-cyanopiperidin-1-yl)quinoline-2-carboxamide;

N-{4-[(3R,4R,5S)-3-amino-4-hydroxy-5-methylpiperidin-1-yl]pyridin-3-yl}-7-(4-methylpiperazin-1-yl)quinoline-2-carboxamide;

N-{4-[(3S,5R)-3-amino-5-methylpiperidin-1-yl]pyridin-3-yl}-7-(4-methylpiperazin-1-yl)quinoline-2-carboxamide;

N-{4-[(3R,4R,5S)-3-amino-4-hydroxy-5-methylpiperidin-1-yl]pyridin-3-yl}-7-(4-pyridin-4-ylpiperidin-1-yl)quinoline-2-carboxamide;

N-{4-[(3S,5R)-3-amino-5-methylpiperidin-1-yl]pyridin-3-yl}-7-(4-pyridin-4-ylpiperidin-1-yl)quinoline-2-carboxamide;

N-{4-[(3R,4R,5S)-3-amino-4-hydroxy-5-methylpiperidin-1-yl]pyridin-3-yl}-7-(4-ethyl-3-oxopiperazin-1-yl)quinoline-2-carboxamide;

N-{4-[(3S,5R)-3-amino-5-methylpiperidin-1-yl]pyridin-3-yl}-7-(4-ethyl-3-oxopiperazin-1-yl)quinoline-2-carboxamide;

N-{4-[(3R,4R,5S)-3-amino-4-hydroxy-5-methylpiperidin-1-yl]pyridin-3-yl}-7-(4-methoxypiperidin-1-yl)quinoline-2-carboxamide;

N-{4-[(3S,5R)-3-amino-5-methylpiperidin-1-yl]pyridin-3-yl}-7-(4-methoxypiperidin-1-yl)quinoline-2-carboxamide;

N-{4-[(3R,4R,5S)-3-amino-4-hydroxy-5-methylpiperidin-1-yl]pyridin-3-yl}-7-(4-morpholin-4-ylpiperidin-1-yl)quinoline-2-carboxamide;

N-{4-[(3S,5R)-3-amino-5-methylpiperidin-1-yl]pyridin-3-yl}-7-(4-morpholin-4-ylpiperidin-1-yl)quinoline-2-carboxamide;

N-{4-[(3R,4R,5S)-3-amino-4-hydroxy-5-methylpiperidin-1-yl]pyridin-3-yl}-7-[3-(trifluoromethyl)pyrrolidin-1-yl]quinoline-2-carboxamide;

N-{4-[(3S,5R)-3-amino-5-methylpiperidin-1-yl]pyridin-3-yl}-7-[3-(trifluoromethyl)pyrrolidin-1-yl]quinoline-2-carboxamide;

N-{4-[(3R,4R,5S)-3-amino-4-hydroxy-5-methylpiperidin-1-yl]pyridin-3-yl}-7-pyrrolidin-1-ylquinoline-2-carboxamide;

N-{4-[(3S,5R)-3-amino-5-methylpiperidin-1-yl]pyridin-3-yl}-7-pyrrolidin-1-ylquinoline-2-carboxamide;

N-{4-[(3R,4R,5S)-3-amino-4-hydroxy-5-methylpiperidin-1-yl]pyridin-3-yl}-7-(3,3-dimethylazetidin-1-yl)quinoline-2-carboxamide;

N-{4-[(3S,5R)-3-amino-5-methylpiperidin-1-yl]pyridin-3-yl}-7-(3,3-dimethylazetidin-1-yl)quinoline-2-carboxamide;

N-{4-[(3S,5R)-3-amino-5-methylpiperidin-1-yl]pyridin-3-yl}-7-azetidin-1-ylquinoline-2-carboxamide;

N-{4-[(3R,4R,5S)-3-amino-5-cyclopropyl-4-hydroxypiperidin-1-yl]pyridin-3-yl}-7-(2,6-difluoro-4-methoxyphenyl)-1,5-naphthyridine-2-carboxamide;

N-{4-[(3R,4R,5S)-3-amino-5-cyclopropyl-4-hydroxypiperidin-1-yl]pyridin-3-yl}-7-(6-methoxypyridin-3-yl)-1,5-naphthyridine-2-carboxamide;

N-{4-[(3R,4R,5S)-3-amino-5-cyclopropyl-4-hydroxypiperidin-1-yl]pyridin-3-yl}-7-(6-morpholin-4-ylpyridin-3-yl)-1,5-naphthyridine-2-carboxamide;

N-{4-[(3R,4R,5S)-3-amino-5-cyclopropyl-4-hydroxypiperidin-1-yl]pyridin-3-yl}-7-(1-ethyl-1H-pyrazol-4-yl)-1,5-naphthyridine-2-carboxamide;

N-{4-[(3R,4R,5S)-3-amino-5-cyclopropyl-4-hydroxypiperidin-1-yl]pyridin-3-yl}-7-(1-methyl-1H-pyrazol-4-yl)-1,5-naphthyridine-2-carboxamide;

N-{4-[(3R,4R,5S)-3-amino-5-cyclopropyl-4-hydroxypiperidin-1-yl]pyridin-3-yl}-7-(3-oxa-9-azaspiro[5.5]undec-9-yl)-1,5-naphthyridine-2-carboxamide;

N-{4-[(3R,4R,5S)-3-amino-5-cyclopropyl-4-hydroxypiperidin-1-yl]pyridin-3-yl}-7-(4-cyanopiperidin-1-yl)-1,5-naphthyridine-2-carboxamide;
N-{4-[(3R,4R,5S)-3-amino-5-cyclopropyl-4-hydroxypiperidin-1-yl]pyridin-3-yl}-7-(1-oxa-8-azaspiro[4.5]dec-8-yl)-1,5-naphthyridine-2-carboxamide;
N-{4-[(3R,4R,5S)-3-amino-4-hydroxy-5-methylpiperidin-1-yl]pyridin-3-yl}-7-(1-methyl-1H-pyrazol-4-yl)quinoline-2-carboxamide;
N-{4-[(3R,4R,5S)-3-amino-4-hydroxy-5-methylpiperidin-1-yl]pyridin-3-yl}-7-(1-ethyl-1H-pyrazol-4-yl)quinoline-2-carboxamide;
N-{4-[(3R,4R,5S)-3-amino-4-hydroxy-5-methylpiperidin-1-yl]pyridin-3-yl}-7-(6-methoxypyridin-3-yl)quinoline-2-carboxamide;
N-{4-[(3R,4R,5S)-3-amino-4-hydroxy-5-methylpiperidin-1-yl]pyridin-3-yl}-7-(6-morpholin-4-ylpyridin-3-yl)quinoline-2-carboxamide;
N-(4-((3R,4R,5S)-3-amino-4-hydroxy-5-methylpiperidin-1-yl)pyridin-3-yl)-7-(pyridin-3-yl)quinoline-2-carboxamide;
N-{4-[(3S,5R)-3-amino-5-methylpiperidin-1-yl]pyridin-3-yl}-7-(1-methyl-1H-pyrazol-4-yl)quinoline-2-carboxamide;
N-{4-[(3S,5R)-3-amino-5-methylpiperidin-1-yl]pyridin-3-yl}-7-(2-cyanophenyl)quinoline-2-carboxamide;
N-(4-((3S,5R)-3-amino-5-methylpiperidin-1-yl)pyridin-3-yl)-7-(4-hydroxypiperidin-1-yl)quinoline-2-carboxamide;
N-{4-[(3S,5R)-3-amino-5-(trifluoromethyl)piperidin-1-yl]pyridin-3-yl}-7-(2-cyanophenyl)-1,5-naphthyridine-2-carboxamide; and
N-{4-[(3R,4R,5S)-3-amino-4-hydroxy-5-methylpiperidin-1-yl]pyridin-3-yl}-7-[6-(tetrahydro-2H-pyran-4-yloxy)pyridin-3-yl]quinoline-2-carboxamide.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1}halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, indanyl, indenyl and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, naphthyridine (including 1,2-, 1,3-, 1,4-, 1,5-, 1,6-, 1,7-, 1,8-, 2,3- and 2,6-naphthyridine), indole, benzothiophene, benzofuran, benzisoxazole, imidazo[1,2-b]thiazole, purine, or the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfide group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidine, azepane, dihydrobenzofuran, dihydrofuran, dihydropyran, morpholine, 3-oxa-9-azaspiro[5.5]undecane, 1-oxa-8-azaspiro[4.5]decane, piperidine, piperazine, oxopiperazine, pyran, pyrrolidine, quinuclidine, tetrahydrofuran, tetrahydropyran, 1,2,3,4-tetrahydroquinoline, tropane, and thiomorpholine.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); aq. (aqueous); atm. (atmosphere(s)); Boc (t-butoxycarbonyl); BOP ((benzotriazol-1-yloxy)tris(dimethylamino)phosphonium hexafluorophosphate); Cbz (carboxybenzyl); calc. (calculated); $Cs_2CO_3$ (cesium carbonate); d (doublet); dd (doublet of doublets); DCM (dichloromethane); DIAD (N,N'-diisopropyl azidodicarboxylate); DIC (N,N'-diisopropylcarbodiimide); DIPEA (N,N-diisopropylethylamine); DMAP (4-dimethylaminopyridine); DMF (N,N-dimethylformamide); ESI (electrospray ionization); Et (ethyl); $Et_2O$ (diethyl ether); EtOAc (ethyl acetate); Fmoc (9-fluorenylmethylmethoxycarbonyl); g (gram(s)); h (hour(s)); $H_2$ (hydrogen gas); HATU (N,N,N',N'-tetramethyl-O-(7-azabenzotriazol-1-yl)uronium hexafluorophosphate); HCl (hydrochloric acid/hydrogen chloride); HPLC (high performance liquid chromatography); Hz (hertz); IPA (isopropyl alcohol); J (coupling constant); $K_2CO_3$ (potassium carbonate); $K_3PO_4$ (potassium phosphate); LiHMDS (Lithium hexamethyldisilazide); LCMS (liquid chromatography—mass spectrometry); $LiAlH_4$ (lithium tetrahydroaluminate); $LiBH_4$ (lithium tetrahydroborate); m (multiplet); M (molar); $MgSO_4$ (magnesium sulfate); MS (Mass spectrometry); Me (methyl); MeCN (acetonitrile); MeI (methyl iodide); MeOH (methanol); mg (milligram(s)); min. (minutes(s)); mL (milliliter(s)); mmol (millimole(s)); $MoSO_4$ (molybdenum sulfate) N (normal); $N_2$ (nitrogen gas); $NaHCO_3$ (sodium bicarbonate); NaOH (sodium hydroxide); $Na_2SO_4$ (sodium sulfate); $NH_4OH$ (ammonium hydroxide); $NH_4Cl$ (ammonium chloride); nM (nanomolar); NMR (nuclear magnetic resonance spectroscopy); Pd (palladium); pM (picomolar); $PPh_3$ (triphenylphosphine); PTFE (polytetrafluoroethylene); RP-HPLC (reverse phase high performance liquid chromatography); t (triplet or tertiary); t-Bu (tert-butyl); t-BuOH (tert-butanol) TEA (triethylamine); TFA (trifluoroacetic acid); THF (tetrahydrofuran); $TiCl_4$ (titanium tetrachloride); g (microgram(s)); µL (microliter(s)); M (micromolar); wt % (weight percent).

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in Scheme 1. In the process shown in Scheme 1, a suitably substituted aromatic or heteroaromatic carboxaldehyde 1-1 ($X^1$=halogen, e.g. chloro, bromo, iodo) can be converted to a compound of Formula 1-2 (R=alkyl), e.g., by heating with a suitable alkyl bromopyruvate in the presence of pyridine. The resulting ester of Formula 1-2 can be hydrolyzed to a corresponding acid 1-3 under standard saponification conditions also known to one skilled in the art. (Wuts et al). The carboxylic acid 1-3 can then be reacted with an appropriately substituted aminopyridine 1-4 under conditions suitable for formation of an amide bond to form an amide of Formula 1-5. Suitable combinations for forming the amide bond include, e.g., the methods used to form amide bonds in peptides as described, e.g., in Jones, *Amino Acid and Peptide Synthesis*, $2^{nd}$ Ed., Oxford University Press, 2002; and Jones, *The Chemical Synthesis of Peptides (International Series of Monographs on Chemistry)* (Oxford University Press, 1994). An example of a suitable coupling agent is HATU/DIPEA.

The amide of Formula 1-5 can be coupled to $R^3$ under conditions suitable for formation of a bond such as a C—C bond or C—N bond to form a compound of formula 1-6. Suitable conditions include organometallic cross coupling reactions. Suitable conditions for forming a C—C bond include, e.g., Suzuki conditions, Stille conditions, Sonogashira conditions, Negishi conditions, Heck conditions and the like. Suitable conditions for formation of a C—N bond include, e.g., Buchwald-Hartwig amination conditions, and copper-mediated conditions, e.g. conditions described in D. M. T. Chan, K. L. Monaco, R.-P. Wang, M. P. Winters, Tetrahedron Lett. 1998, 39, 2933-2936 and P. Y. S. Lam, C. G. Clark, S. Saubern, J Adams, M P. P Winters, D. M. T. Chan, A. Combs, Tetrahedron Let. 1998, 39, 2941-2944. The substitutions of compound 1-6 can be further transformed to desired functional groups.

Compounds of Formula (I) can be prepared, e.g., using a process as illustrated in Scheme 2. In the process shown in Scheme 2, a suitably substituted aromatic or heteroaromatic carboxaldehyde 2-1 can be converted to a compound of Formula 2-2 (R=alkyl), e.g., by heating with a suitable alkyl bromopyruvate in the presence of pyridine. The resulting ester of Formula 2-2 can be hydrolyzed to a corresponding acid 2-3 under standard saponification conditions also known to one skilled in the art. (Wuts et al). The carboxylic acid 2-3 can then be reacted with an appropriately substituted aminopyridine 2-4 under conditions suitable for formation of an amide bond to form an amide of Formula 2-5, which corresponds to the compound of Formula (I). Suitable combinations for forming the amide bond include, e.g., the methods used to form amide bonds in peptides as described, e.g., in Jones, *Amino Acid and Peptide Synthesis*, $2^{nd}$ Ed., Oxford University Press, 2002; and Jones, *The Chemical Synthesis of Peptides (International Series of Monographs on Chemistry)* (Oxford University Press, 1994). An example of a suitable coupling agent is HATU/DIPEA. The substitutions of compound 2-5 can be further transformed to desired functional groups.

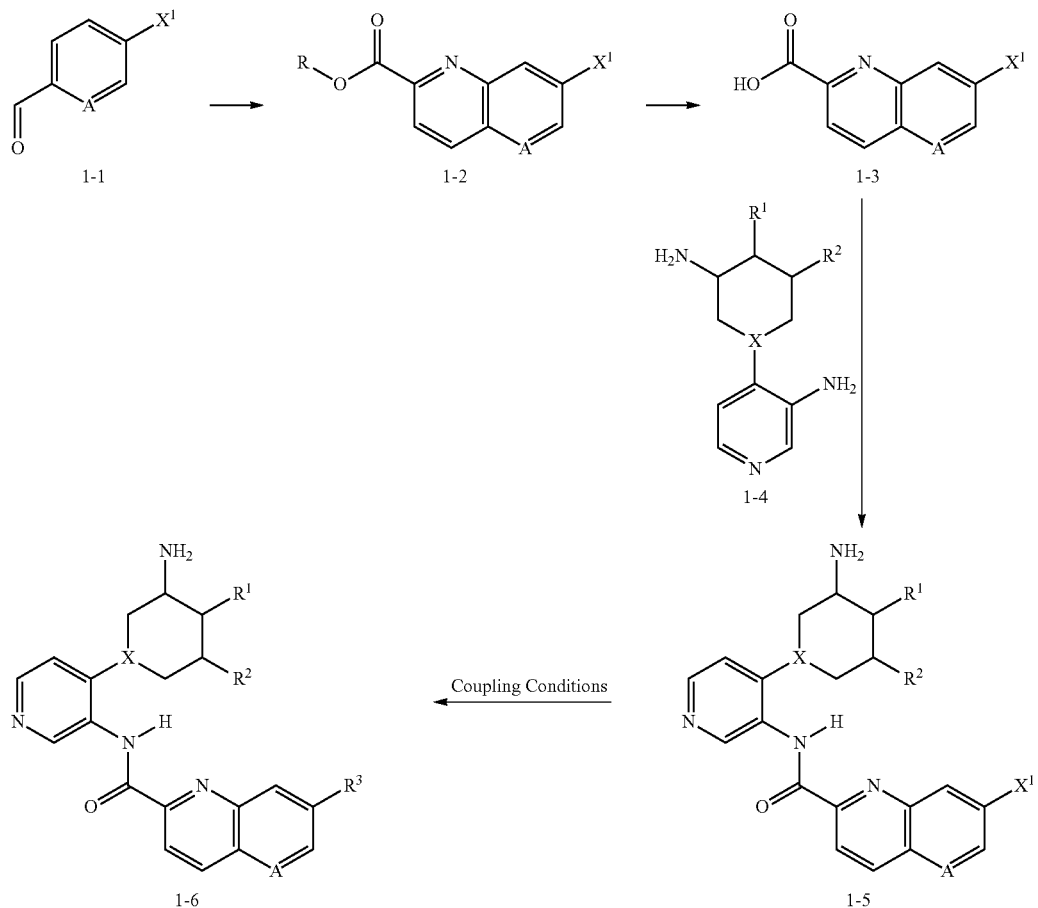

Scheme 2

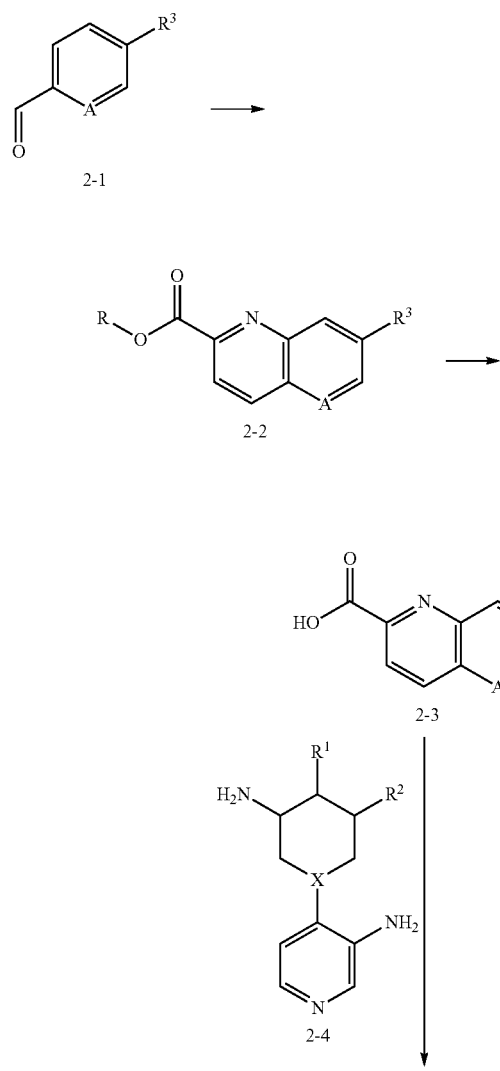

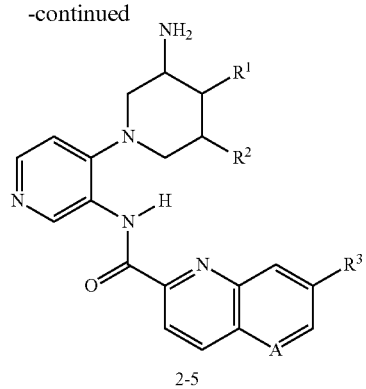

Other compounds of Formula (I) can be prepared by appropriate modifications of the synthetic route described above. For example, compounds according to Formula (I) with various functional groups can be prepared by suitable functional group interconversion reactions known to one of ordinary skill in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

The synthetic methods illustrated by Scheme 1 can be applied to the synthesis of quinoline compounds as shown in Scheme 3. A substituted benzaldehyde 3-1 ($X^1$=halogen, e.g. chloro, bromo, iodo) is heated with ethyl bromopyruvate in the presence of pyridine to provide quinoline 3-2. The resulting ester 3-2 is hydrolyzed to corresponding acid 3-3 and reacted with an appropriately substituted aminopyridine 3-4 under coupling conditions to afford an amide 3-5. The amide of Formula 3-5 can be coupled to $R^3$ under conditions suitable for formation of a C—C bond or C—N bond to form compound 3-6. Suitable conditions for forming a C—C bond include, e.g., Suzuki conditions, Stille conditions, Sonogashira conditions, Negishi conditions, and the like. Suitable conditions for formation of a C—N bond include, e.g., Buchwald-Hartwig amination conditions, and copper-mediated conditions, e.g. conditions described in D. M. T. Chan, K. L Monaco, R.-P. Wang, M. P. Winters, Tetrahedron Lett. 1998, 39, 2933-2936 and P. Y. S. Lam, C. G. Clark, S. Saubem, J Adams, M. P. Winters, D. M. T. Chan, A. Combs, Tetrahedron Lett. 1998, 39, 2941-2944. The substitutions of compound 3-6 can be further transformed to desired functional groups.

Scheme 3

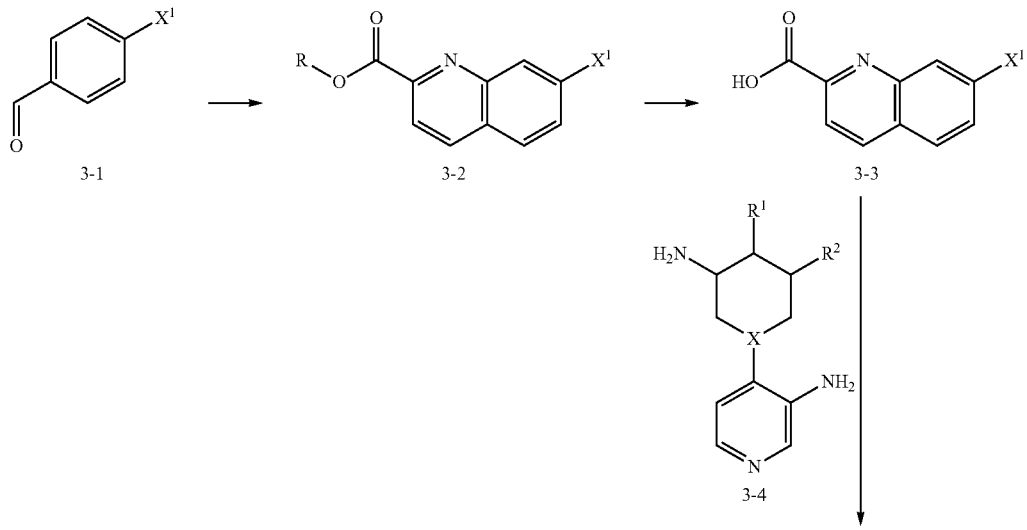

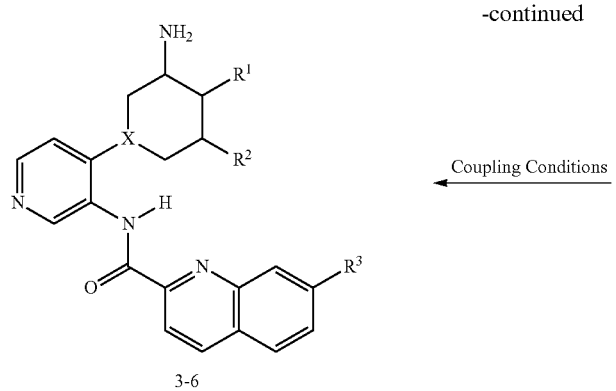

3-6

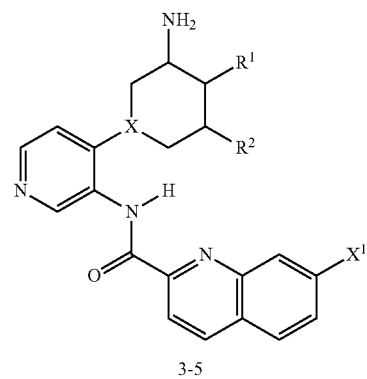

3-5

The synthetic method illustrated by Scheme 1 can be applied to the synthesis of 1,5-naphthyridine compounds as shown in Scheme 4. A substituted picolinaldehyde 4-1 ($X^1$=halogen, e.g. chloro, bromo, iodo) is heated with ethyl bromopyruvate in the presence of pyridine to provide naphthyridine 4-2. The resulting ester 4-2 is hydrolyzed to corresponding acid 4-3 and reacted with an appropriately substituted aminopyridine 4-4 under coupling conditions to afford an amide 4-5. The amide of Formula 4-5 can be coupled to $R^3$ under conditions suitable for formation of a C—C bond or C—N bond to form compound 4-6. Suitable conditions for forming a C—C bond include, e.g., Suzuki conditions, Stille conditions, Sonogashira conditions, Negishi conditions, and the like. Suitable conditions for formation of a C—N bond include, e.g., Buchwald-Hartwig amination conditions, and copper-mediated conditions, e.g. conditions described in D. M. T. Chan, K. L Monaco, R.-P. Wang, M. P. Winters, Tetrahedron Lett. 1998, 39, 2933-2936 and P. Y. S. Lam, C. G. Clark, S. Saubem, J Adams, M. P. Winters, D. M. T. Chan, A. Combs, Tetrahedron Lett. 1998, 39, 2941-2944. The substitutions of compound 4-6 can be further transformed to desired functional groups.

Scheme 4

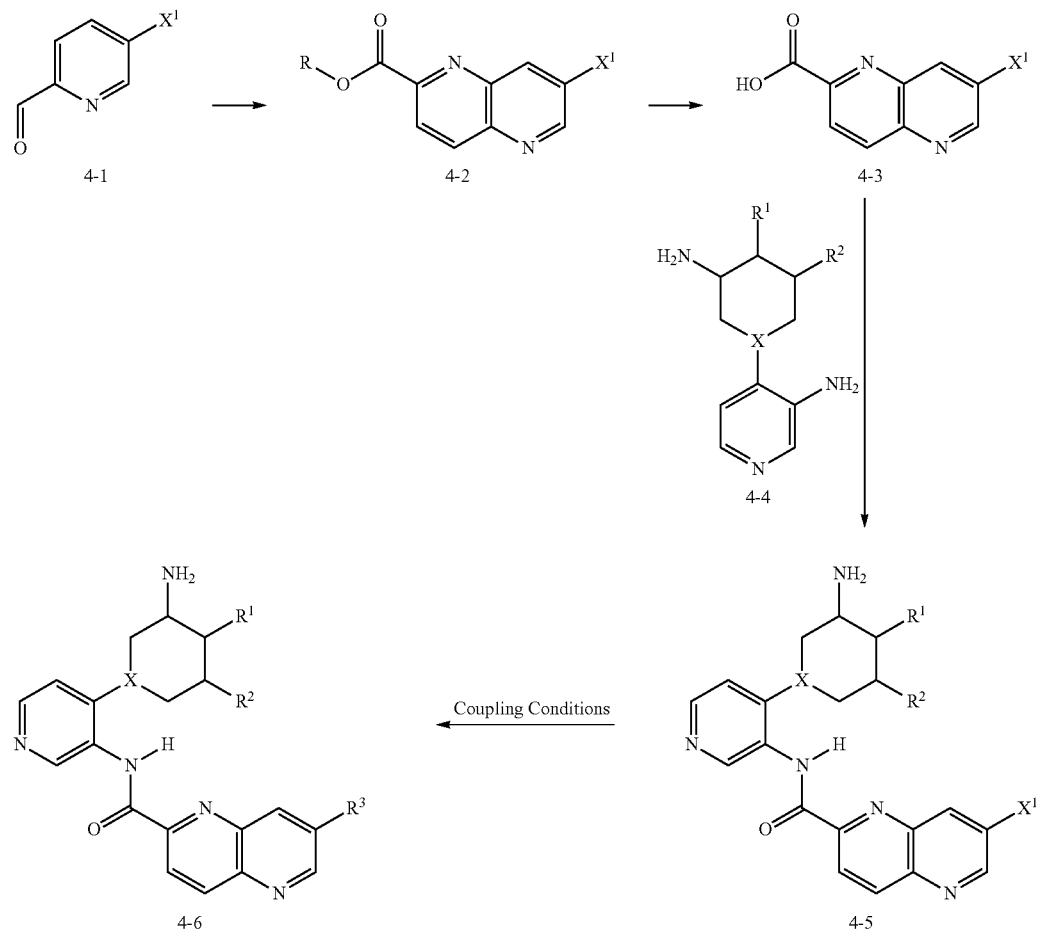

The synthetic methods illustrated by Scheme 2 can be applied to the synthesis of quinoline compounds as shown in Scheme 5. A substituted benzaldehyde 5-1 is heated with ethyl bromopyruvate in the presence of pyridine to provide quinoline 5-2. The resulting ester 5-2 is hydrolyzed to corresponding acid 5-3 and reacted with an appropriately substituted aminopyridine 5-4 under coupling conditions to afford an amide 5-5. The substitutions on 5-5 can be further transformed to desired functional groups in the final product, or in any of the steps of the synthesis, using methods know to one skilled in the art.

to provide naphthyridine 6-2. The resulting ester 6-2 is hydrolyzed to corresponding acid 6-3 and reacted with an appropriately substituted aminopyridine 6-4 under coupling conditions to afford an amide 6-5. The substitutions on 6-5 can be further transformed to desired functional groups in the final product, or in any of the steps of the synthesis, using methods know to one skilled in the art.

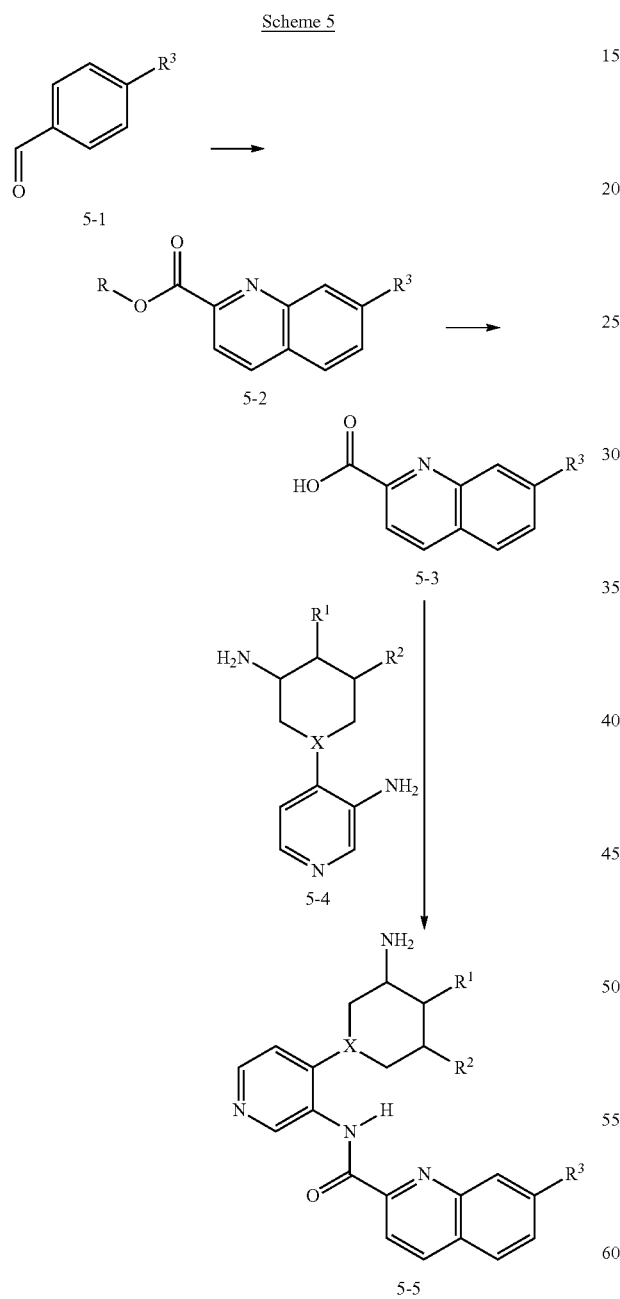

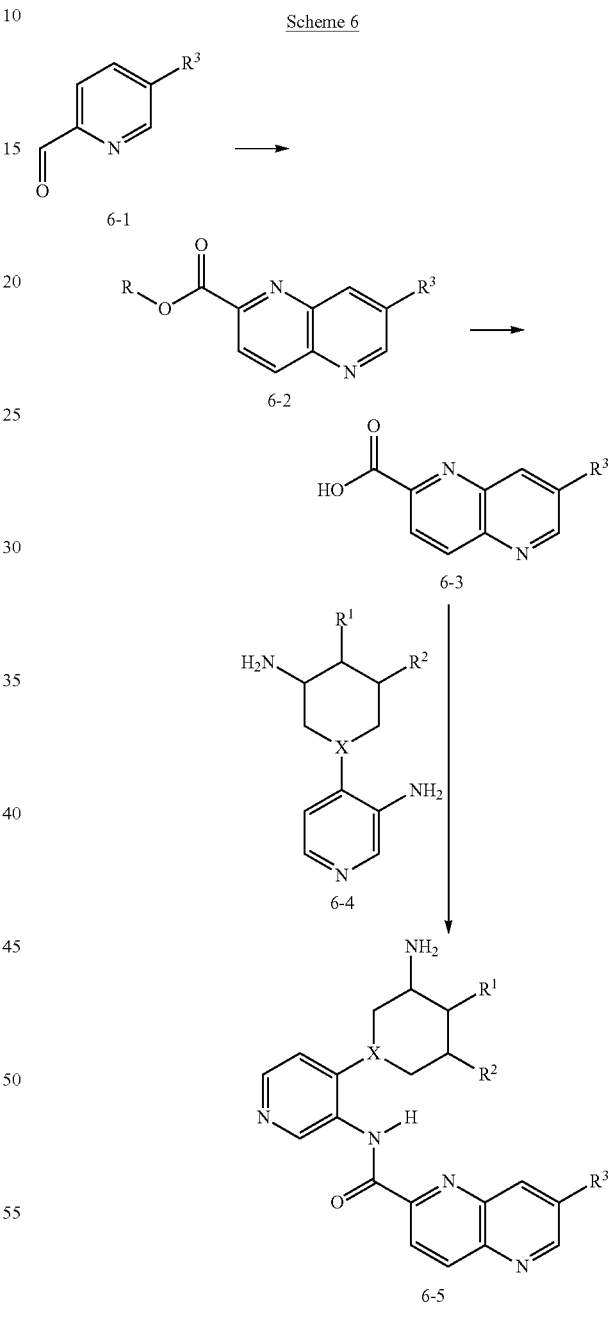

The synthetic method illustrated by Scheme 2 can be applied to the synthesis of 1,5-naphthyridine compounds as shown in Scheme 6. A substituted picolinaldehyde 6-1 is heated with ethyl bromopyruvate in the presence of pyridine Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of one or more members of the Pim kinase family and, thus, are useful in treating diseases and disorders associated with activity of Pim kinases. For the uses described herein, any of the compounds of the invention, including any of the embodiments thereof, may be used.

The compounds of the invention can inhibit one or more of Pim1, Pim2 and Pim3. In some embodiments the compounds are selective for one Pim kinase over another. "Selective" means that the compound binds to or inhibits a Pim kinase with greater affinity or potency, respectively, compared to a reference enzyme, such as another Pim kinase. For example, the compounds can be selective for Pim1 over Pim2 and Pim3, selective for Pim2 over Pim1 and Pim3, or selective for Pim3 over Pim1 and Pim2. In some embodiments, the compounds inhibit all of the Pim family members (e.g., Pim1, Pim2 and Pim3). In some embodiments, the compounds can be selective for Pim over other kinases such as receptor and non-receptor Ser/Thr kinases such as Akt1, Akt2, Akt3, TGF-βR, PKA, PKG, PKC, CaM-kinase, phosphorylase kinase, MEKK, ERK, MAPK and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK or ABL. In general, selectivity can be at least about 5-fold, at least about 10-fold, at least about 20-fold, at least about 50-fold, at least about 100-fold, at least about 200-fold, at least about 500-fold or at least about 1000-fold. The method of inhibiting a Pim1, Pim2 or Pim3 kinase includes contacting the appropriate enzyme with the compound of the invention, or any of the embodiments thereof, or a pharmaceutically acceptable salt thereof.

Thus, the present disclosure provides methods of treating a Pim kinase-associated disease or disorder in an individual (e.g., patient) by administering to the individual in need of such treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a Pim kinase-associated disease or disorder. Also provided is the use of a compound of the invention, or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated using the compounds of the invention include cancer, including, in particular, cancers in which Pim kinases are upregulated or an oncogene, e.g., Myc or Bcl2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (A ML), chronic lymphocytic leukemia (CLL), chronic myelogenous leukemia (C ML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated using the compounds of the invention also include myeloproliferative disorders such as polycythemia vera (PV), essential thrombocythemia (ET), chronic myelogenous leukemia (C ML) and the like. The myeloproliferative disorder can be myelofibrosis such as primary myelofibrosis (PMF), myelofibrosis with myeloid metaplasia (MMM), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

Pim kinase-associated diseases that can be treated with compounds according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated with compounds according to the invention also include atherosclerosis.

The compounds of the invention can also be used to inhibit disease processes in which Pim-kinases are involved, including angiogenesis and tumor metastasis.

Due to the fact that Pim kinases are regulated by the JAK/STAT pathway, the compounds of the invention are useful to treat diseases in which modulating JAK/STAT signaling is beneficial. Thus, other diseases that can be treated using the compounds of the invention include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitus (type I).

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

The Pim inhibitors of the present invention can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

The Pim inhibitors of the present invention can further be used in combination with one or more anti-inflammatory agents, steroids, immunosuppressants or therapeutic antibodies.

When more than one pharmaceutical agent is administered to a patient, they can be administered simultaneously, sequentially, or in combination (e.g., for more than two agents).

IV. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™).

In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Pim kinases in tissue samples, including human, and for identifying Pim kinase ligands by inhibition binding of a labeled compound. Accordingly, the present invention includes Pim kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro Pim kinase labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a Pim-kinase by monitoring its concentration variation when contacting with the Pim kinase, through tracking of the labeling. For example, a test compound (labeled) can be evaluated for its ability to reduce binding of another compound which is known to bind to a Pim kinase (i.e., standard compound). Accordingly, the ability of a test compound to compete with the standard compound for binding to the Pim kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of Pim kinase-associated diseases or disorders, such as cancer, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

The compounds of the Examples have been found to be Pim-kinase inhibitors according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, J. Combi. Chem., 2002, 4, 295-301; Blom et al., "Optimizing Preparative LC-MS Configurations and Methods for Parallel Synthesis Purification", J. Combi. Chem., 2003, 5, 670-83; and Blom et al., "Preparative LC-MS Purification: Improved Compound Specific Method Optimization", J. Combi. Chem., 2004, 6, 874-883.

Intermediate 1 tert-Butyl [(3S,5R)-1-(3-aminopyridin-4-yl)-5-methyl-piperidin-3-yl]carbamate

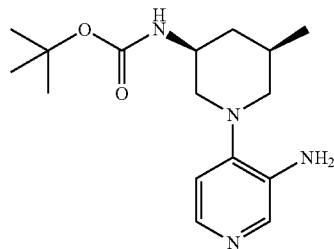 [SMILES: C[C@@H]1C[C@H](NC(=O)OC(C)(C)C)CN(c2ccncc2N)C1]

Step 1. 1-tert-butyl 2-methyl (2S,4R)-4-methyl-5-oxopyrrolidine-1, 2-dicarboxylate

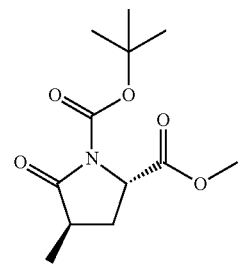 [SMILES: COC(=O)[C@@H]1C[C@@H](C)C(=O)N1C(=O)OC(C)(C)C]

A solution of 1-tert-butyl 2-methyl (2S)-5-oxopyrrolidine-1,2-dicarboxylate (16.1 g, 66.2 mmol) in THF (100 mL) was cooled to −78° C. LiHMDS in THF (1.0 M, 68.2 mL, 68.2 mmol) was added dropwise over 5 min. The resulting mixture was stirred at −78° C. for 35 min., then MeI (10.0 mL, 160 mmol) was added. The reaction was warmed to room temperature slowly overnight. The reaction was quenched with AcOH (7.5 mL, 130 mmol) and water (5 mL) and then the mixture concentrated under reduced pressure. The concentrated residue was further diluted with water and extracted with EtOAc (3 times). The combined extracts were washed with water and brine, dried over Na₂SO₄, filtered, and concentrated under reduced pressure. The residue was purified by silica gel column and eluted with 0-50% EtOAc/Hexanes over 45 min. Fractions were checked by TLC (MoSO₄ stain) and LCMS. 6.1 g (35% yield) of the sub-title compound was obtained. LCMS calc. for C₇H₁₂NO₃ (M+H-Boc+H)⁺: m/z=158.1; found: 158.1.

Step 2. tert-Butyl [(1S,3R)-4-hydroxy-1-(hydroxymethyl)-3-methylbutyl]carbamate

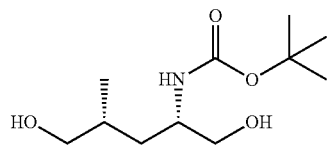 [SMILES: C[C@@H](CO)C[C@@H](CO)NC(=O)OC(C)(C)C]

A solution of 1-tert-butyl 2-methyl (2S,4R)-4-methyl-5-oxopyrrolidine-1,2-dicarboxylate (11.0 g, 42.8 mmol) in THF (100 mL) was cooled to 0° C. then LiBH₄ (2.8 g, 130 mmol) and then EtOH (22 mL) were added. The mixture was slowly allowed to warm to room temperature and stirred for 4 h. The reaction was quenched with water then extracted with EtOAc (3 times). The combined extracts were dried over Na₂SO₄, filtered, and concentrated under reduced pressure to give 4.5 g (45% yield) of the crude sub-title compound. The crude product was used without further purification.

Step 3. tert-Butyl [(3S,5R)-1-benzyl-5-methylpiperidin-3-yl]carbamate

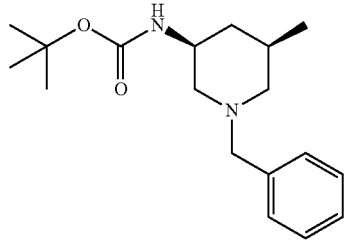 [SMILES: C[C@@H]1C[C@H](NC(=O)OC(C)(C)C)CN(Cc2ccccc2)C1]

A solution of tert-butyl [(1S,3R)-4-hydroxy-1-(hydroxymethyl)-3-methylbutyl]carbamate (9.50 g, 40.7 mmol) in DCM (200 mL) was cooled to 0° C. TEA (23 mL, 160 mmol) was added, followed by dropwise addition of methanesulfonyl chloride (9.4 mL, 120 mmol). The clear solution became cloudy and yellow and the mixture was stirred at 0° C. for 1 h. The mixture was diluted with DCM and washed with saturated aq. NaHCO₃ and water. The organic layer was dried over Na₂SO₄, filtered, and concentrated under reduced pressure to give an intermediate mesylate as a yellow oil that was used immediately for the next step. The intermediate mesylate and benzylamine (90 mL, 800 mmol) were combined in microwave vial, sealed and heated at 70° C. overnight. After 18 h, the mixture was quenched with 10% aq. NaOH. The mixture was then extracted with hexanes (3 times). The combined extracts were washed with brine, dried over MgSO₄, filtered, and concentrated under reduced pressure. The residue was purified on a silica gel column and eluted with 0-40% EtOAc/hexane over 34 min. to give 6.0 g (49% yield) of the sub-title compound as a white solid. LCMS calc. for C₁₈H₂₉N₂O₂ (M+H)⁺: m/z=305.2; found: 305.1.

Step 4. tert-Butyl [(3S,5R)-5-methylpiperidin-3-yl]carbamate

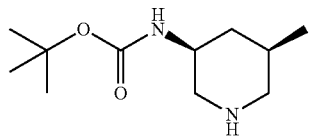

A mixture of tert-butyl [(3S,5R)-1-benzyl-5-methylpiperidin-3-yl]carbamate (4.5 g, 15 mmol), AcOH (2.0 mL, 35 mmol) and 10% Pd on carbon (1.6 g, 1.5 mmol) in EtOH (100 mL) was stirred in a Par-shaker under H₂ (50 psi) overnight. The mixture was filtered through a pad of diatomaceous earth and concentrated under reduced pressure. The residue was diluted with DCM (500 mL) and washed with saturated aq. NaHCO₃ solution. The aqueous layer was extracted twice with DCM. The combined DCM extract was dried over Na₂SO₄ and concentrated under reduced pressure to give 2.2 g (67% yield) of the sub-title compound as a white solid. LCMS calc. for C₁₁H₂₃N₂O₂ (M+H)⁺: m/z=: 215.2; found: 215.1.

Step 5. tert-Butyl [(3S,5R)-5-methyl-1-(3-nitropyridin-4-yl)piperidin-3-yl]carbamate

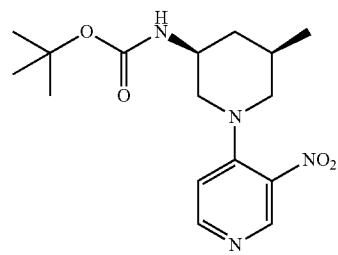 [SMILES: C[C@@H]1C[C@H](NC(=O)OC(C)(C)C)CN(c2ccncc2[N+](=O)[O-])C1]

A mixture of 4-chloro-3-nitropyridine (740 mg, 4.7 mmol), tert-butyl [(3S,5R)-5-methylpiperidin-3-yl]carbamate (1000.0 mg, 4.67 mmol) and DIPEA (2.4 mL, 14 mmol) was irradiated in a microwave oven for 1 h at 130° C. The reaction mixture was concentrated under reduced pressure and the residue was purified by column chromatography on silica gel using a CombiFlash® apparatus eluting with EtOAc/hexane (10-60%). The purification gave 1.21 g (80% yield) of the sub-title compound as a colorless oil. LCMS calc. for C₁₆H₂₅N₄O₄ (M+H)⁺: m/z 337.2; found: 337.1.

Step 6. tert-butyl [(3S,5R)-1-(3-aminopyridin-4-yl)-5-methylpiperidin-3-yl]carbamate A mixture of tert-butyl [(3S,5R)-5-methyl-1-(3-nitropyridin-4-yl)piperidin-3-yl]carbamate (100 mg, 0.3 mmol), iron powder (0.072 g, 1.3 mmol), AcOH (2.0 mL, 35 mmol) and water (0.2 mL, 10 mmol) was stirred at room temperature for 60 min. When the reaction was complete, the reaction mixture was concentrated under reduced pressure, diluted with EtOAc, filtered through a pad of diatomaceous earth, washed with aqueous NaHCO₃ solution, washed with water and brine, dried over Na₂SO₄, and concentrated under reduced pressure to give 60 mg (60% yield) of the title compound as a brown solid. LCMS calc. for $C_{16}H_{27}N_4O_2$ (M+H)⁺: m/z 307.1; found: 307.1.

Intermediate 2

N-{4-[(3S,5R)-3-Amino-5-methylpiperidin-1-yl]pyridin-3-yl}-7-bromo-1,5-naphthyridine-2-carboxamide

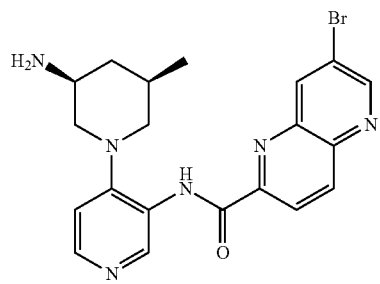 [SMILES: C[C@@H]1C[C@H](N)CN(c2ccncc2NC(=O)c2ccc3ncc(Br)cc3n2)C1]

Step 1. 7-Bromo-1,5-naphthyridine-2-carboxylic acid

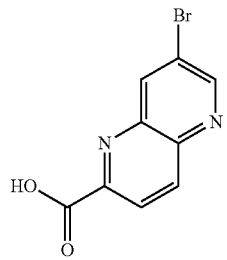 [SMILES: O=C(O)c1ccc2ncc(Br)cc2n1]

To a solution of 1,5-naphthyridine-2-carboxylic acid (from Princeton Bio, Catalogue Number PBMR019135; 0.87 g, 5.0 mmol) in AcOH (20 mL) was added N-bromosuccinimide (1.1 g, 6.0 mmol). The mixture was stirred at 120° C. overnight. The reaction was concentrated under reduced pressure, treated with EtOAc (30 mL), and filtered to afford the crude product as white solid which was used in the next step without further purification. LCMS calc. for $C_9H_6BrN_2O_2$[M+H]⁺ m/z: 253.1; found 253.1.

Step 2. N-{4-[(3S,5R)-3-Amino-5-methylpiperidin-1-yl]pyridin-3-yl}-7-bromo-1,5-naphthyridine-2-carboxamide To a solution of 7-bromo-1,5-naphthyridine-2-carboxylic acid (510 mg, 2.0 mmol) and tert-butyl [(3S,5R)-1-(3-aminopyridin-4-yl)-5-methylpiperidin-3-yl]carbamate (670 mg, 2.2 mmol) in DMF (12.0 mL) was added DIPEA (650 mg, 5.0 mmol) and HATU (912 mg, 2.40 mmol). The reaction mixture was stirred at room temperature for 2 h and was then concentrated under reduced pressure. The mixture was dissolved in DCM (10 mL) and TFA (1.54 mL, 20.0 mmol) was added. The reaction mixture was stirred at 50° C. for 1 h. The mixture was then concentrated under reduced pressure and purified by chromotography (MeOH/DCM 5-20%) to afford the title compound as colorless solid (650 mg, 74%). LCMS calc. for $C_{20}H_{22}BrN_6O$ [M+H]⁺ m/z: 441.1; found 441.1.

Intermediate 3 tert-Butyl ((3R,4R,5S)-1-(3-aminopyridin-4-yl)-4-{[tert-butyl(dimethyl)silyl]oxy}-5-methylpiperidin-3-yl)carbamate

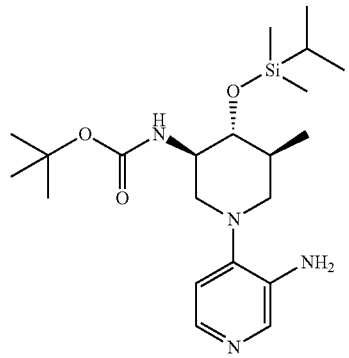 [SMILES: CC(C)[Si](C)(C)O[C@@H]1[C@@H](C)CN(c2ccncc2N)C[C@H]1NC(=O)OC(C)(C)C]

Step 1. tert-Butyl (4R)-4-{(1R,2R)-3-[(4R)-4-benzyl-2-oxo-1, 3-oxazolidin-3-yl]-1-hydroxy-2-methyl-3-oxopropyl}-2, 2-dimethyl-1, 3-oxazolidine-3-carboxylate

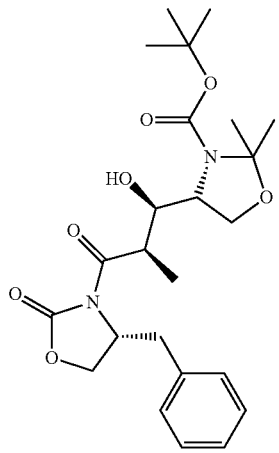

To a solution of (R)-3-(1-oxopropyl)-4-benzyl-2-oxazolidinone (12 g, 51 mmol) in DCM (300 mL) (0.13 M), 1.0 M TiCl₄ in DCM (51 mL, 51 mmol) was added at −40° C. The mixture was stirred at −40° C. for 10 min., then DIPEA (22 mL, 130 mmol) was added, forming a dark red solution. The mixture was stirred at 0° C. for 20 min. tert-Butyl (4R)-4-formyl-2,2-dimethyl-1,3-oxazolidine-3-carboxylate (12 g, 51 mmol) in DCM (100 mL) (0.5 M) was then added dropwise and the resulting mixture was stirred for 1.5 h at 0° C. LCMS showed 2 peaks with the mass corresponding to the title compound, one major peak and one minor peak (5:2). The reaction mixture was quenched by the addition of aq. NH₄Cl solution and the mixture was extracted with DCM. The organic phase was separated, washed with brine, dried over MgSO$_4$, concentrated under reduced pressure, and purified by chromatography on silica gel (0-40% EtOAc/hexane) to give 8 g (30% yield) of the sub-title compound as a colorless oil. LCMS calc. for C$_{24}$H$_{35}$N$_2$O$_7$ (M+H)$^+$: m/z=463.2; found: 463.1.

Step 2. tert-Butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate

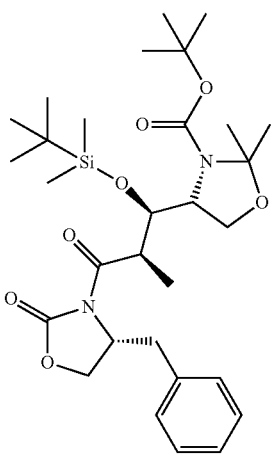

To a solution of tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate (12.1 g, 26.2 mmol) and 2,6-lutidine (5.4 mL, 47 mmol) in DCM (260 mL) (0.1 M) was added tert-butyldimethylsilyl trifluoromethanesulfonate (8.41 mL, 36.6 mmol) at −40° C. The mixture was stirred at −40° C. for 2 h. The reaction mixture was diluted with DCM, washed with saturated aq. NaHCO$_3$ solution, dried over Na$_2$SO$_4$, concentrated under reduced pressure, and purified by chromatography on silica gel (0-20% EtOAc/hexane) to give 14 g (92.8% yield) of the sub-title compound as a colorless gel. LCMS calc. for C$_{25}$H$_{41}$N$_2$O$_5$Si (M+H-Boc+H)$^+$: m z 477.3; found: 477.1.

Step 3. tert-Butyl (4R)-4-((1R,2S)-1-{[tert-butyl (dimethyl)silyl]oxy}-3-hydroxy-2-methylpropyl)-2, 2-dimethyl-1,3-oxazolidine-3-carboxylate

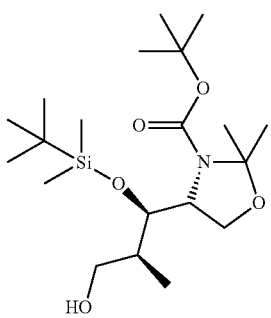

To a solution of tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2, 2-dimethyl-1,3-oxazo-lidine-3-carboxylate (14.0 g, 24.3 mmol) and EtOH (4.2 mL, 73 mmol) in THF (300 mL) (0.09 M) was added LiBH$_4$ (1.6 g, 73 mmol) at −30° C. The mixture was allowed to warm to 0° C. and stirred overnight. The reaction mixture was diluted with ether and 1 M NaOH was added. The resulting mixture was extracted with EtOAc and the organic extract was washed with brine, dried over Na$_2$SO$_4$, concentrated under reduced pressure, and purified by chromatography on silica gel (0-20% EtOAc/hexane) to give 4.1 g (42% yield) of the sub-title compound as a colorless oil. LCMS calc. for C$_{15}$H$_{34}$NO$_3$Si (M+H-Boc+H)$^+$: m/z=304.2; found: 304.1.

Step 4. tert-Butyl (4R)-4-((1R,2S)-3-azido-1-{[tert-butyl(dimethyl)silyl]oxy}-2-methylpropyl)-2,2-dimethyl-1,3-oxazolidine-3-carboxylate

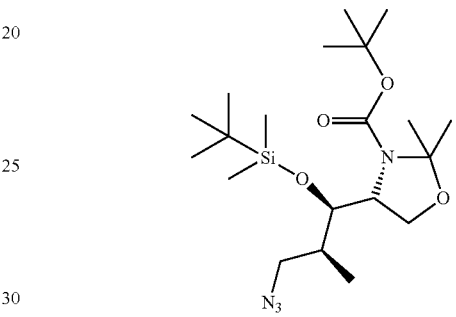

To a mixture of tert-butyl (4R)-4-((1R,2S)-1-{[tert-butyl (dimethyl)silyl]oxy}-3-hydroxy-2-methylpropyl)-2,2-dimethyl-1,3-oxazolidine-3-carboxylate (8.20 g, 20.3 mmol), diisopropyl azodicarboxylate (8.0 mL, 41 mmol) and PPh$_3$ (11 g, 41 mmol) in THF (100 mL) (0.18 M), diphenylphosphonic azide (8.8 mL, 41 mmol) was added. The mixture was stirred at room temperature overnight. The mixture was concentrated under reduced pressure, and the residue was purified by chromatography on silica gel (0-15% EtOAc/hexane) to give 5.2 g (60% yield) of the sub-title compound as a yellowish oil. LCMS calc. for C$_{20}$H$_{41}$N$_4$O$_4$Si (M+H)$^+$: m/z=429.3; found: 429.1.

Step 5. tert-Butyl [(1R,2R,3S)-4-azido-2-{[tert-butyl (dimethyl)silyl]oxy}-1-(hydroxymethyl)-3-methylbutyl]carbamate

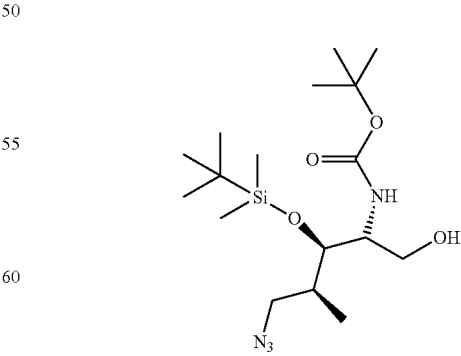

To a solution of tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate (10.5 g, 24.5 mmol) in EtOH (70 mL) was added pyridinium p-toluenesulfonate (12.3 g, 49.0 mmol) and the mixture was then heated under reflux for 2 days.

The volatile solvents were removed under reduced pressure and the residue was dissolved in DCM (200 mL, 0.1 M). To the resulting solution were added DIPEA (8.53 mL, 49.0 mmol) and di-tert-butyldicarbonate (6.42 g, 29.4 mmol). The reaction mixture was stirred at room temperature for 5 h. The mixture was concentrated under reduced pressure and purified by chromatography on silica gel (0-25% EtOAc/Hexane) to give 5.8 g (61% yield) of the sub-title compound as a colorless oil. LCMS calc. for $C_{12}H_{29}N_4O_2Si$ (M+H−Boc+H)$^+$: m/z=289.2; found: 289.1.

Step 6. (2R,3R,4S)-5-Azido-2-[(tert-butoxycarbonyl)amino]-3-{[tert-butyl(dimethyl)silyl]oxy}-4-methylpentyl methanesulfonate

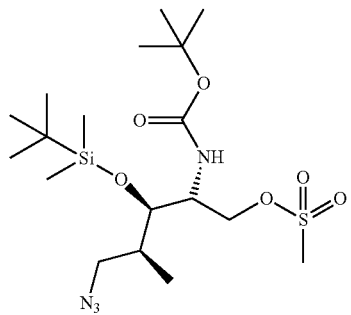

To a solution of tert-butyl [(1R,2R,3S)-4-azido-2-{[tert-butyl(dimethyl)silyl]oxy}-1-(hydroxymethyl)-3-methylbutyl]carbamate (5.80 g, 14.9 mmol) in pyridine (75 mL) at 0° C. was added methanesulfonyl chloride (1.50 mL, 19.4 mmol) and DMAP (0.36 g, 3.0 mmol). The mixture was stirred at 0° C. for 1 h. The solution was diluted with EtOAc, washed with saturated NaHCO$_3$ solution, concentrated under reduced pressure and purified by chromatography on silica gel (0-25% EtOAc/Hexane) to give 4.8 g (69% yield) of the sub-title compound as a colorless oil. LCMS calc. for $C_{13}H_{31}N_4O_4SSi$ (M+H−Boc)$^+$: m/z=367.2; found: 367.2.

Step 7. tert-Butyl ((3R,4R,5S)-4-{[tert-butyl(dimethyl)silyl]oxy}-5-methylpiperidin-3-yl)carbamate

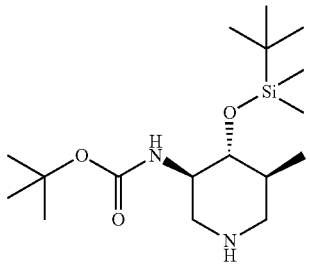 [SMILES: C[C@H]1CNC[C@@H](NC(=O)OC(C)(C)C)[C@@H]1O[Si](C)(C)C(C)(C)C]

A solution of (2R,3R,4S)-5-azido-2-[(tert-butoxycarbonyl)amino]-3-{[tert-butyl(dimethyl)silyl]oxy}-4-methylpentyl methanesulfonate (4.25 g, 9.11 mmol) in MeOH (100 mL) (0.09M) was deoxygenated with a stream of N$_2$ for 20 min. DIPEA (4.0 mL, 23 mmol) was added, followed by 10% Pd on carbon (0.97 g, 0.91 mmol). The reaction mixture was stirred under a balloon containing H$_2$ for 2 h. The solution was filtered through a pad of diatomaceous earth and rinsed with MeOH. The filtrate was concentrated under reduced pressure to give 2.10 g (66% yield) of the sub-title compound as a white solid. LCMS calc. for $C_{17}H_{37}N_2O_3Si$ (M+H)$^+$: m/z=345.3; found: 345.1.

Step 8. tert-Butyl [(3R,4R,5S)-4-{[tert-butyl(dimethyl)silyl]oxy}-5-methyl-1-(3-nitropyridin-4-yl)piperidin-3-yl]carbamate

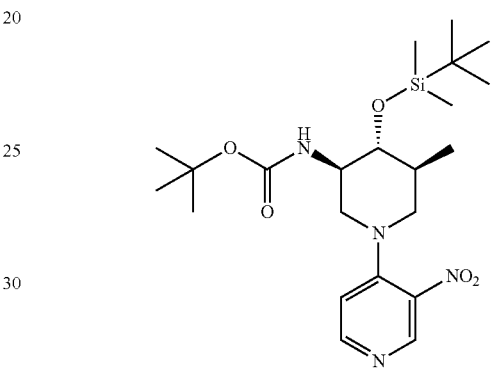

A mixture of 4-chloro-3-nitropyridine (150.0 mg, 0.9461 mmol) and tert-butyl ((3R,4R,5S)-4-{[tert-butyl(dimethyl)silyl]oxy}-5-methylpiperidin-3-yl)carbamate (300.0 mg, 0.8707 mmol) and TEA (0.3763 mL, 2.700 mmol) in IPA (10.0 mL) was stirred at 60° C. for 2 h. The reaction mixture was concentrated under reduced pressure and the residue was purified by column chromatography on silica gel using a CombiFlash® apparatus (eluting with 0 to 30% EtOAc in hexane) to give 100 mg (24% yield) of the sub-title compound. LCMS calc. for $C_{22}H_{39}N_4O_5Si$ (M+H)$^+$: m/z=467.3; found: 467.1.

Step 9. tert-Butyl ((3R,4R,5S)-1-(3-aminopyridin-4-yl)-4-{[tert-butyl(dimethyl)silyl]oxy}-5-methylpiperidin-3-yl) carbamate A mixture of tert-butyl [(3R,4R,5S)-4-{[tert-butyl(dimethyl)silyl]oxy}-5-methyl-1-(3-nitropyridin-4-yl)piperidin-3-yl]carbamate (100.00 mg, 0.27858 mmol), AcOH (10.00 mL) and iron powder (558.4 mg, 9.999 mmol) was stirred at ambient temperature for 2 h. The mixture was diluted with 30 mL of EtOAc and filtered through a pad of diatomaceous earth. The combined organic filtrate was then concentrated under reduced pressure. The residue was diluted with EtOAc and washed with aq. Na$_2$CO$_3$ solution and 0.2 M NaOH. The organic phase was concentrated under reduced pressure to give 50 mg (47% yield) of the title compound. LCMS calc. for $C_{22}H_{41}N_4O_3Si$ (M+H)$^+$: m/z=437.3; found: 437.1.

Intermediate 4

N-{4-[(3R,4R,5S)-3-Amino-4-hydroxy-5-methylpiperidin-1-yl]pyridin-3-yl}-7-bromo-1,5-naphthyridine-2-carboxamide

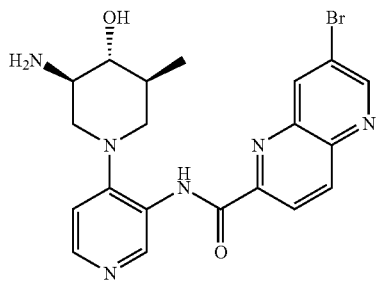 [SMILES: C[C@H]1CN(c2ccncc2NC(=O)c2ccc3ncc(Br)cc3n2)C[C@@H](N)[C@@H]1O]

To a solution of 7-bromo-1,5-naphthyridine-2-carboxylic acid (1700 mg, 6.9 mmol) and tert-butyl ((3R,4R,5S)-1-(3-aminopyridin-4-yl)-4-{[tert-butyl(dimethyl)silyl]oxy}-5-methylpiperidin-3-yl)carbamate (2500 mg, 5.7 mmol) in DMF (50 mL) was added DIPEA (1.8 g, 14.0 mmol) and HATU (2.4 g, 6.2 mmol). The reaction mixture was stirred at room temperature for 2 h before it was concentrated under reduced pressure. The mixture was dissolved in DCM (50 mL) and TFA (5.32 mL, 69 mmol) was added. The reaction was then stirred at 50° C. for 1 h before it was concentrated under reduced pressure and purified by chromatography (MeOH/DCM 5-20%) to afford the title product as colorless solid (1.80 g, 69%). LCMS calc. for $C_{20}H_{22}BrN_6O_2$[M+H]$^+$ m/z: 457.1; found 457.1.

Intermediate 5 tert-Butyl ((3R,4R,5S)-1-(3-aminopyridin-4-yl)-4-{[tert-butyl(dimethyl)silyl]oxy}-5-cyclopropylpiperidin-3-yl)carbamate

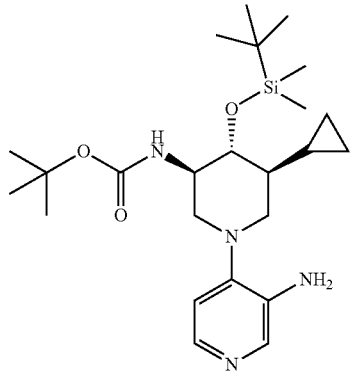 [SMILES: CC(C)(C)OC(=O)N[C@@H]1CN(c2ccncc2N)C[C@H](C2CC2)[C@H]1O[Si](C)(C)C(C)(C)C]

Step 1. tert-Butyl (4R)-4-{(1R,2R)-3-[(4R)-4-benzyl-2-oxo-1,3-oxazolidin-3-yl]-2-cyclopropyl-1-hydroxy-3-oxopropyl}-2,2-dimethyl-1,3-oxazolidine-3-carboxylate

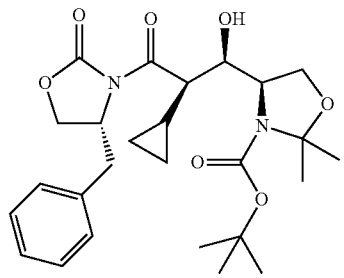 [SMILES: CC(C)(C)OC(=O)N1[C@@H]([C@H](O)[C@H](C(=O)N2C(=O)OC[C@H]2Cc2ccccc2)C2CC2)COC1(C)C]

To a solution of (4R)-4-benzyl-3-(cyclopropylacetyl)-1,3-oxazolidin-2-one (2.0 g, 7.7 mmol) in anhydrous DCM (45 mL) at −40° C. was added a solution of 1.0 M TiCl$_4$ in DCM (9.3 mL) dropwise under an atmosphere of N$_2$, forming a yellow slurry. After 10 min., DIPEA (3.36 mL, 19.3 mmol) was added dropwise, changing the color from yellow to deep purple. The reaction mixture was allowed to gradually warm to −20° C. while stirring over 1 h. The reaction mixture was then cooled to −40° C. prior to the dropwise addition of a solution of tert-butyl (4R)-4-formyl-2,2-dimethyl-1,3-oxazolidine-3-carboxylate (1.8 g, 7.85 mmol) (Aldrich cat#462063) in anhydrous DCM (5 mL). The reaction mixture was allowed to gradually warm to 0° C. for 1 h and then stirred for an additional 1.5 h at 0° C. The reaction was quenched by the addition of saturated aq. NH$_4$Cl (15 mL). After separation of the two layers that formed, the organic layer was washed with water and brine, dried over Na$_2$SO$_4$, concentrated under reduced pressure, and purified by flash chromatography (120 g silica gel, eluting with 0-60% EtOAc/hexanes) to afford the sub-title compound (1.9 g, 50%). LCMS (ESI) calc. for $C_{26}H_{36}N_2O_7$Na (M+Na)$^+$: m/z 511.2, found 511.1.

Step 2. tert-Butyl (4R)-4-((1R,2R)-3-[(4R)-4-benzyl-2-oxo-1,3-oxazolidin-3-yl]-1-{[tert-butyl(dimethyl)silyl]oxy}-2-cyclopropyl-3-oxopropyl)-2,2-dimethyl-1,3-oxazolidine-3-carboxylate

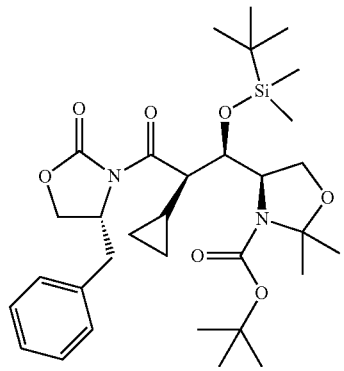 [SMILES: CC(C)(C)OC(=O)N1[C@@H]([C@H](O[Si](C)(C)C(C)(C)C)[C@H](C(=O)N2C(=O)OC[C@H]2Cc2ccccc2)C2CC2)COC1(C)C]

To a solution of tert-butyl (4R)-4-{(1R,2R)-3-[(4R)-4-benzyl-2-oxo-1,3-oxazolidin-3-yl]-2-cyclopropyl-1-hydroxy-3-oxopropyl)}-2,2-dimethyl-1,3-oxazolidine-3-carboxylate (1.80 g, 3.68 mmol) in anhydrous DCM (10 mL) at −40° C., 2,6-lutidine (0.85 mL, 7.3 mmol) was added under an atmosphere of N₂. After 10 min., a solution of tert-butyldimethylsilyl trifluoromethanesulfonate (1.1 mL, 4.9 mmol) in anhydrous DCM (1 mL) was added. The reaction mixture was allowed to warm gradually to ambient temperature while stirring overnight. The crude reaction mixture was diluted with 1,2-dichloroethane and cooled to 0° C., then quenched with saturated aq. NaHCO₃. After separation of the two layers, the organic layer was washed with water and brine, dried over Na₂SO₄, concentrated under reduced pressure, and purified by flash chromatography (120 g silica gel, eluting with 0-30% EtOAc/hexanes) to afford the sub-title compound (2.1 g, 95%). LCMS (ESI) calc. for $C_{32}H_{50}N_2O_7SiNa$ (M+Na)⁺: m/z=625.3, found 625.1.

Step 3. tert-Butyl (4R)-4-((1R,2S)-1-{[tert-butyl(dimethyl)silyl]oxy}-2-cyclopropyl-3-hydroxypropyl)-2,2-dimethyl-1,3-oxazolidine-3-carboxylate

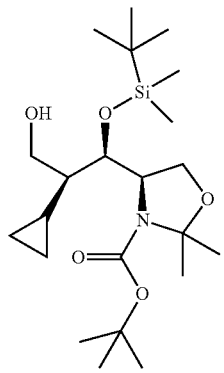 [SMILES: CC(C)(C)OC(=O)N1[C@@H]([C@H](O[Si](C)(C)C(C)(C)C)[C@H](CO)C2CC2)COC1(C)C]

A solution of tert-butyl (4R)-4-((1R,2R)-3-[(4R)-4-benzyl-2-oxo-1,3-oxazolidin-3-yl]-1-{[tert-butyl(dimethyl)silyl]oxy}-2-cyclopropyl-3-oxopropyl)-2,2-dimethyl-1,3-oxazolidine-3-carboxylate (3.3 g, 5.5 mmol) in anhydrous THF (50 mL) and EtOH (1 mL) under an atmosphere of N₂ was cooled to −30° C. prior to the addition of LiBH₄ (0.24 g, 11 mmol). The reaction mixture was gradually warmed to ambient temperature while stirring for 20 h. The crude reaction mixture was diluted with Et₂O (36 mL) and cooled to 0° C. prior to the addition of 1 M aq. NaOH (36 mL). After separation of the layers, the aqueous layer was extracted with EtOAc several times and the combined organic extracts were washed with brine, dried over Na₂SO₄, filtered, and concentrated under reduced pressure. The crude product was purified by flash column chromatography (120 g silica gel, eluting with 0-40% EtOAc/hexanes) to afford the sub-title compound (1.27 g, 54%). LCMS (ESI) calc. for $C_{22}H_{43}NO_5SiNa$ (M+Na)⁺: 452.3, found 452.0.

Step 4. tert-Butyl (4R)-4-((1R,2S)-3-azido-1-{[tert-butyl(dimethyl)silyl]oxy}-2-cyclopropylpropyl)-2,2-dimethyl-1,3-oxazolidine-3-carboxylate

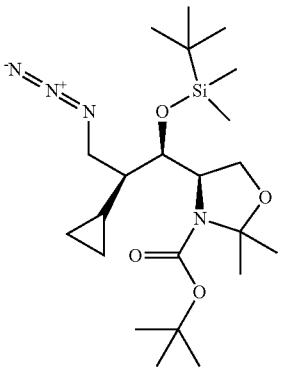

To a solution of tert-butyl (4R)-4-((1R,2S)-1-{[tert-butyl(dimethyl)silyl]oxy}-2-cyclopropyl-3-hydroxypropyl)-2,2-dimethyl-1,3-oxazolidine-3-carboxylate (1.3 g, 3.0 mmol) and PPh₃ (1.6 g, 6.1 mmol) in anhydrous THF (20 mL) was added diisopropyl azodicarboxylate (1.2 mL, 5.9 mmol) dropwise under an atmosphere of N₂. Upon completion of the addition, a precipitate was formed. The reaction mixture was stirred for 30 min. prior to the addition of a solution of diphenylphosphonic azide (1.3 mL, 6.2 mmol) in anhydrous THF (1.0 mL). After stirring at ambient temperature for 3 h, the volatile organic solvents were removed under reduced pressure and the crude product was purified by flash column chromatography (120 g of silica gel, eluting with 0-15% EtOAc-hexanes) to afford the sub-title compound as a light yellow oil (1.18 g, 86%). LCMS (ESI) calc. for $C_{17}H_{35}N_4O_2Si$ (M+H−Boc+H)⁺: 355.30, found 355.1.

Step 5. tert-Butyl [(1R,2R,3S)-4-azido-2-{[tert-butyl(dimethyl)silyl]oxy}-3-cyclopropyl-1-(hydroxymethyl)butyl]carbamate

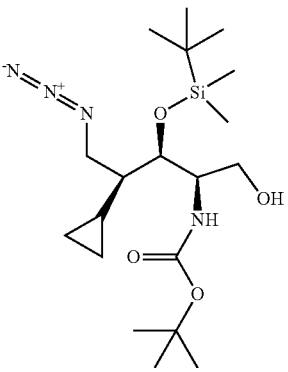

To a solution of tert-butyl (4R)-4-((1R,2S)-3-azido-1-{[tert-butyl(dimethyl)silyl]oxy}-2-cyclopropylpropyl)-2,2-dimethyl-1,3-oxazolidine-3-carboxylate (1.16 g, 2.55 mmol) in MeOH (5 mL) at 0° C. was added TFA (4.9 mL, 64 mmol) and the resulting solution was stirred at ambient temperature for 1 h. The volatile organic solvents were removed under reduced pressure and the residue was azeotropically washed with toluene (2×3 mL). The residue was dissolved in anhydrous DCM (18 mL), then DIPEA (0.99 g, 7.6 mmol) and di-tert-butyldicarbonate (0.84 g, 3.8 mmol) were added and the resulting solution was stirred at ambient temperature for 1 h. The volatile solvents were removed under reduced pressure and the crude product was purified by flash column chromatography (120 g silica gel, eluting with 0-100% EtOAc/hexanes) to afford the sub-title compound (0.57 g, 54%) and the desilylated product (0.2 g, 26%). LCMS (ESI) calc. for $C_{14}H_{31}N_4O_2Si$ (M+H-Boc+H)$^+$: m/z=315.3, found 315.0.

Step 6. tert-Butyl-(2R,3R,4S)-5-azido-2-[(tert-butoxycarbonyl)amino]-3-{[tert-butyl(dimethyl)silyl]oxy}-4-cyclopropylpentyl methanesulfonate

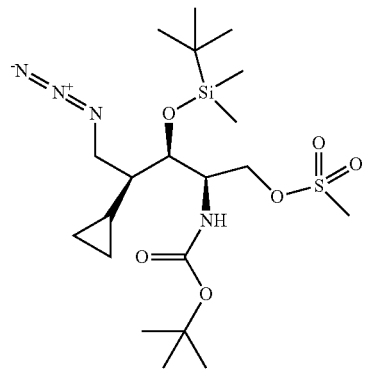

To a solution of tert-butyl [(1R,2R,3S)-4-azido-2-{[tert-butyl(dimethyl)-14-sulfanyl]oxy}-3-cyclopropyl-1-(hydroxymethyl)butyl]carbamate (0.240 g, 0.573 mmol) in anhydrous pyridine (2.0 mL) −20° C. was added DMAP (0.014 g, 0.11 mmol) and methanesulfonyl chloride (0.044 mL, 0.57 mmol). The reaction mixture was allowed to warm gradually to 5° C. and stirred for 2 h. The crude reaction mixture was diluted with EtOAc and concentrated under reduced pressure onto silica gel and purified by flash column chromatography (24 g silica gel, eluting with 0-20% EtOAc-hexanes) to afford the sub-title compound (0.240 g, 86%). LCMS (ESI) calc. for $C_{15}H_{33}N_4O_4SSi$ (M+H-Boc+H)$^+$: m/z=393.2; found 393.0.

Step 7. ((3R,4R,5S)-4-{[tert-butyl(dimethyl)silyl]oxy}-5-cyclopropylpiperidin-3-yl)carbamate

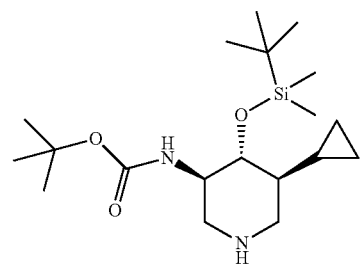 [SMILES: CC(C)(C)OC(=O)N[C@@H]1CNC[C@H](C2CC2)[C@H]1O[Si](C)(C)C(C)(C)C]

A solution of (2R,3R,4S)-5-azido-2-[(tert-butoxycarbonyl)amino]-3-{[tert-butyl (dimethyl)silyl]oxy}-4-cyclopropylpentyl methanesulfonate (0.250 g, 0.507 mmol) and DIPEA (0.26 mL, 1.5 mmol) in MeOH (8.0 mL) was purged with $N_2$ prior to the addition of 10% Pd (dry basis) on activated carbon, wet, Degussa type E101 NE/W (0.080 g, 0.076 mmol). The reaction mixture was stirred under an atmosphere of $H_2$ via a balloon for 2 h. The inorganics were then filtered off, rinsed thoroughly with MeOH and EtOAc, and the filtrate was concentrated under reduced pressure to afford the sub-title compound (0.244 g). LCMS (ESI) calc. for $C_{19}H_{39}N_2O_3Si$ (M+H)$^+$: m/z=371.3, found 371.1. $^1$H NMR (500 MHz, CDCl$_3$) δ 4.56 (s, 1H), 3.36-3.23 (m, 3H), 3.04 (dd, J=13.0, 3.1 Hz, 1H), 2.35 (ddd, J=14.7, 12.5, 11.0 Hz, 2H), 1.43 (s, 9H), 0.75 (tt, J=9.4, 4.7 Hz, 1H), 0.63-0.52 (m, 1H), 0.47 (ddt, J=13.0, 8.2, 4.1 Hz, 1H), 0.38 (qd, J=9.2, 5.5 Hz, 2H), 0.08--0.02 (m, 1H) ppm.

Step 8. tert-Butyl [(3R,4R,5S)-4-{[tert-butyl(dimethyl)silyl]oxy}-5-cyclopropyl-1-(3-nitropyridin-4-yl)piperidin-3-yl]carbamate

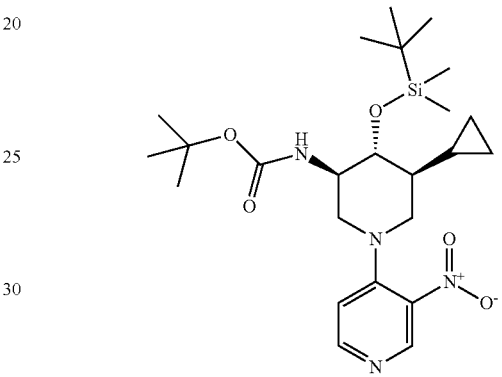

A mixture of tert-butyl ((3R,4R,5S)-4-{[tert-butyl(dimethyl)silyl]oxy}-5-cyclopropylpiperidin-3-yl)carbamate (0.180 g, 0.486 mmol), 4-chloro-3-nitropyridine (0.10 g, 0.63 mmol) and TEA (0.20 mL, 1.4 mmol) in IPA (1.8 mL) was heated at 75° C. in a sealed vial for 1 h. After cooling to ambient temperature, the reaction mixture was diluted with EtOAc (40 mL) and water (3 mL). The layers that formed were separated, the organic layer was washed with water (2×3 mL) and the combined aqueous phases were back extracted with EtOAc (3 mL). The combined organic layers were washed with brine (3 mL), dried over Na$_2$SO$_4$, filtered, and concentrated under reduced pressure. The crude product was purified by flash column chromatography (20 g silica gel column, eluting with 0-20% EtOAc/hexanes) to afford the sub-title compound (0.135 g, 56%). LCMS (ESI) calc. for $C_{24}H_{41}N_4O_5Si$ (M+H)$^+$: m/z=493.3, found 493.1.

Step 9. tert-Butyl ((3R,4R,5S)-1-(3-aminopyridin-4-yl)-4-{[tert-butyl(dimethyl)silyl]oxy}-5-cyclopropylpiperidin-3-yl) carbamate A mixture of tert-butyl [(3R,4R,5S)-4-{[tert-butyl(dimethyl)silyl]oxy}-5-cyclopropyl-1-(3-nitropyridin-4-yl)piperidin-3-yl]carbamate (0.140 g, 0.284 mmol) and 10% Pd (dry basis) on activated carbon, wet, Degussa type E101 NE/W (0.040 g, 0.038 mmol) in MeOH (3.5 mL) and EtOAc (0.5 mL) was purged with $N_2$ prior to stirring under an atmosphere of $H_2$ (introduced via a balloon) overnight. The crude reaction mixture was filtered through a pad of diatomaceous earth and the inorganics were washed thoroughly with EtOAc. The filtrate was concentrated under reduced pressure afford the sub-title compound (0.125 g, 95%). LCMS (ESI) calc. for $C_{24}H_{43}N_4O_3Si$ (M+H)$^+$: m/z=463.3, found 463.1.

Example 1

N-{4-[(3S,5R)-3-Amino-5-methylpiperidin-1-yl]pyridin-3-yl}-7-(2,6-difluorophenyl)-1,5-naphthyridine-2-carboxamide

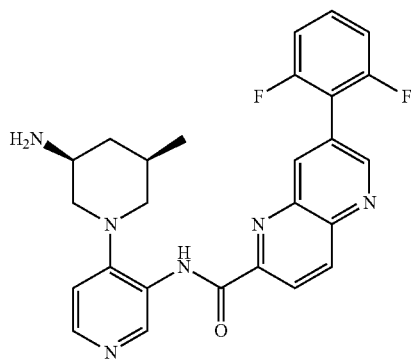 [SMILES: C[C@@H]1C[C@H](N)CN(c2ccncc2NC(=O)c2ccc3ncc(-c4c(F)cccc4F)cc3n2)C1]

To a solution of N-{4-[(3S,5R)-3-amino-5-methylpiperidin-1-yl]pyridin-3-yl}-7-bromo-1,5-naphthyridine-2-carboxamide (20.0 mg, 0.0453 mmol), 2-(2,6-difluorophenyl)-4,4,5,5-tetramethyl-1,3,2-dioxaborolane (from Combi-Blocks, Catalogue Number: PN2659; 22.0 mg, 0.0916 mmol) in 1,4-dioxane (1.0 mL) and water (0.3 mL) were added $Cs_2CO_3$ (30 mg, 0.091 mmol) and (2'-aminobiphenyl-2-yl)(chloro)[dicyclohexyl(2',4',6'-triisopropylbiphenyl-2-yl)phosphoranylidene]palladium (3.6 mg, 0.0045 mmol). The reaction mixture was stirred at 90° C. for 1 h before it was diluted and purified by RP-HPLC (pH 10) to yield the title product (10.0 mg, 47%). LCMS calc. for $C_{26}H_{25}F_2N_6O$ $[M+H]^+$ m/z: 475.1; found 475.1. $^1H$ NMR (500 MHz, DMSO-$d_6$) δ 9.39 (s, 1H), 9.24 (d, J=3.0 Hz, 1H), 8.77 (d, J=5.0 Hz, 1H), 8.76 (s, 1H), 8.63 (s, 1H), 8.58 (d, J=5.0 Hz, 1H), 8.28 (d, J=5.0 Hz, 1H), 7.65 (m, 1H), 7.35 (t, J=10.0 Hz, 2H), 7.13 (d, J=5.0 Hz, 1H), 3.27 (m, 2H), 3.20 (d, J=15.0 Hz, 1H), 3.10 (m, 1H), 3.09 (m, 1H), 2.32 (t, J=12.5 Hz, 1H), 2.23 (t, J=12.5 Hz, 1H), 2.15 (m, 1H), 1.98 (d, J=12.5 Hz, 1H), 0.82 (d, J=5.0 Hz, 3H) ppm.

Example 2

N-{4-[(3S,5R)-3-Amino-5-methylpiperidin-1-yl]pyridin-3-yl}-7-isopropyl-1,5-naphthyridine-2-carboxamide

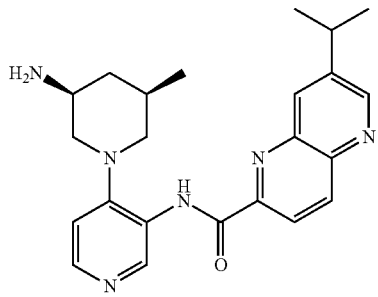 [SMILES: CC(C)c1cnc2ccc(C(=O)Nc3cnccc3N3C[C@H](C)C[C@H](N)C3)nc2c1]

To a solution of N-{4-[(3S,5R)-3-amino-5-methylpiperidin-1-yl]pyridin-3-yl})-7-bromo-1,5-naphthyridine-2-carboxamide (20.0 mg, 0.0453 mmol), 2-isopropenyl-4,4,5,5-tetramethyl-1,3,2-dioxaborolane (from Sigma-Aldrich, Catalogue Number: 663212; 15.4 mg, 0.0916 mmol) in 1,4-dioxane (1.0 mL) and water (0.3 mL) were added $Cs_2CO_3$ (30 mg, 0.091 mmol) and (2'-aminobiphenyl-2-yl)(chloro)[dicyclohexyl(2',4',6'-triisopropylbiphenyl-2-yl)phosphoranylidene]palladium (3.6 mg, 0.0045 mmol). The reaction mixture was stirred at 90° C. for 1 h before it was concentrated under reduced pressure. The mixture was dissolved in MeOH (1 mL) and Pd on carbon (10% wt, 10 mg) was added. The reaction mixture was stirred under a $H_2$ balloon for 2 h before it was filtered, diluted, and purified by RP-HPLC (pH 10). LCMS calc. for $C_{23}H_{29}N_6O$ $[M+H]^+$ m/z: 405.1; found 405.1.

Example 3

N-{4-[(3S,5R)-3-Amino-5-methylpiperidin-1-yl]pyridin-3-yl}-7-(tetrahydro-2H-pyran-4-yl)-1,5-naphthyridine-2-carboxamide

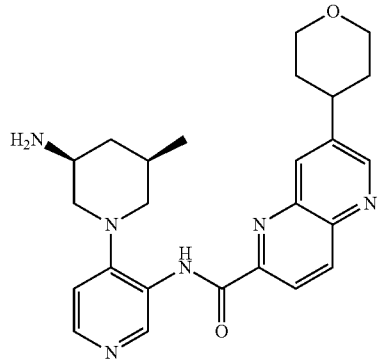 [SMILES: C[C@@H]1C[C@H](N)CN(c2ccncc2NC(=O)c2ccc3ncc(C4CCOCC4)cc3n2)C1]

This compound was synthesized by the same method described in Example 2 by using 4-(4,4,5,5-tetramethyl-1,3,2-dioxaborolan-2-yl)-3,6-dihydro-2H-pyran (from Sigma-Aldrich, Catalogue Number: D10417) instead of 2-isopropenyl-4,4,5,5-tetramethyl-1,3,2-dioxaborolane. LCMS calc. for $C_{25}H_{31}N_6O_2$ $[M+H]^+$ m/z: 447.1; found 447.1.

Example 4

N-{4-[(3S,5R)-3-Amino-5-methylpiperidin-1-yl]pyridin-3-yl}-7-(2,6-difluoro-4-methoxyphenyl)-1,5-naphthyridine-2-carboxamide

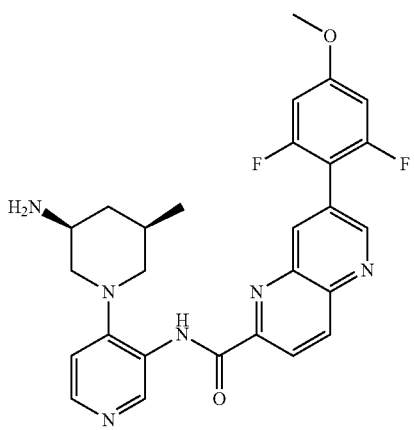 [SMILES: COc1cc(F)c(-c2cnc3ccc(C(=O)Nc4cnccc4N4C[C@H](C)C[C@H](N)C4)nc3c2)c(F)c1]

This compound was synthesized by the same method described in Example 1 by using (2,6-difluoro-4-methoxyphenyl)boronic acid (from Sigma-Aldrich, Catalogue Number: 593060) instead of 2-(2,6-difluorophenyl)-4,4,5,5-tetramethyl-1,3,2-dioxaborolane. LCMS calc. for $C_{27}H_{27}F_2N_6O_2[M+H]^+$ m/z: 505.1; found 505.1.

Example 5

N-{4-[(3S,5R)-3-Amino-5-methylpiperidin-1-yl]pyridin-3-yl}-7-(1-ethyl-1H-pyrazol-4-yl)-1,5-naphthyridine-2-carboxamide

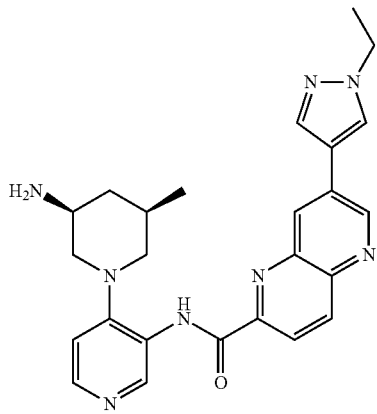 [SMILES: CCn1cc(-c2cnc3ccc(C(=O)Nc4cnccc4N4C[C@H](C)C[C@H](N)C4)nc3c2)cn1]

This compound was synthesized by the same method described in Example 1 by using 1-ethyl-1H-pyrazol-4-yl)boronic acid instead of 2-(2,6-difluorophenyl)-4,4,5,5-tetramethyl-1,3,2-dioxaborolane. LCMS calc. for $C_{25}H_{29}N_8O$ [M+H]$^+$ m/z: 457.2; found 457.1.

Example 6

N-{4-[(3R,4R,5S)-3-Amino-4-hydroxy-5-methylpiperidin-1-yl]pyridin-3-yl}-7-isopropenyl-1,5-naphthyridine-2-carboxamide

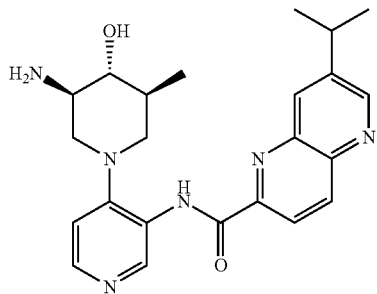 [SMILES: CC(C)c1cnc2ccc(C(=O)Nc3cnccc3N3C[C@@H](N)[C@H](O)[C@@H](C)C3)nc2c1]

This compound was synthesized by the same method described in Example 2 by using tert-butyl((3R,4R,5S)-1-(3-aminopyridin-4-yl)-4-{[tert-butyl(dimethyl)silyl]oxy}-5-methylpiperidin-3-yl)carbamate instead of N-{4-[(3S,5R)-3-amino-5-methylpiperidin-1-yl]pyridin-3-yl}-7-bromo-1,5-naphthyridine-2-carboxamide. LCMS calc. for $C_{23}H_{29}N_6O_2$ [M+H]$^+$ m/z: 421.1; found 421.1. $^1$H NMR (500 MHz, DMSO-d$_6$) δ 10.56 (s, 1H), 9.44 (s, 1H), 9.11 (d, J=3.0 Hz, 1H), 8.66 (d, J=5.0 Hz, 1H), 8.45 (d, J=5.0 Hz, 1H), 8.28 (d, J=5.0 Hz, 1H), 7.15 (d, J=5.0 Hz, 1H), 4.98 (d, J=5.0 Hz, 1H), 3.29 (m, 2H), 3.09 (m, 1H), 2.81 (m, 1H), 2.57 (t, J=10.0 Hz, 1H), 2.49 (m, 5H), 2.16 (m, 1H), 1.40 (s, 3H), 1.38 (s, 3H), 0.91 (d, J=10.0 Hz, 3H) ppm.

Example 7

N-{4-[(3R,4R,5S)-3-Amino-4-hydroxy-5-methylpiperidin-1-yl]pyridin-3-yl}-7-(6-methoxypyridin-3-yl)-1,5-naphthyridine-2-carboxamide

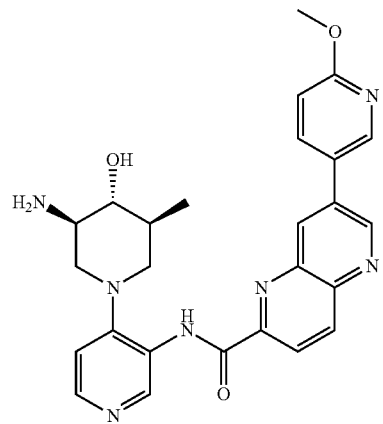 [SMILES: COc1ccc(-c2cnc3ccc(C(=O)Nc4cnccc4N4C[C@@H](N)[C@H](O)[C@@H](C)C4)nc3c2)cn1]

This compound was synthesized by the same method described in Example 6 by using 2-methoxy-5-(4,4,5,5-tetramethyl-1,3,2-dioxaborolan-2-yl)pyridine (from Sigma-Aldrich, Catalogue Number: 636029) instead of 2-isopropenyl-4,4,5,5-tetramethyl-1,3,2-dioxaborolane. LCMS calc. for $C_{26}H_{28}N_7O_3$ [M+H]$^+$ m/z: 486.1; found 486.1.

Example 8

N-{4-[(3R,4R,5S)-3-Amino-4-hydroxy-5-methylpiperidin-1-yl]pyridin-3-yl}-7-morpholin-4-yl-1,5-naphthyridine-2-carboxamide

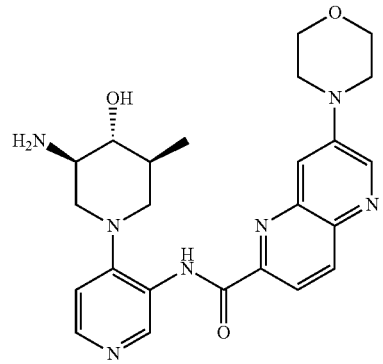 [SMILES: C[C@H]1CN(c2ccncc2NC(=O)c2ccc3ncc(N4CCOCC4)cc3n2)C[C@@H](N)[C@@H]1O]

To a vial, N-{4-[(3R,4R,5S)-3-amino-4-hydroxy-5-methylpiperidin-1-yl]pyridin-3-yl}-7-bromo-1,5-naphthyridine-2-carboxamide (30.0 mg, 0.0656 mmol), K$_3$PO$_4$ (70 mg, 0.33 mmol), dicyclohexyl(2',6'-diisopropoxybiphenyl-2-yl)phosphine-(2'-aminobiphenyl-2-yl)(chloro)palladium (1:1) (34.9 mg, 0.0449 mmol), and dicyclohexyl(2',6'-diisopropoxybiphenyl-2-yl)phosphine (26.2 mg, 0.0561 mmol) were added. The vial was sealed with a PTFE screw-cap, evacuated, and backfilled with N₂ (this process was repeated a total of three times). A solution of morpholine (76.4 mg, 0.877 mmol) in anhydrous t-BuOH (1.0 mL) was added via syringe. The reaction was heated at 100° C. After 2 h at 100° C., the reaction was complete. The product was purified by RP-HPLC (pH=10). LCMS calc. for $C_{24}H_{30}N_7O_3$ [M+H]⁺ m/z: 464.2; found 464.1.

Example 9

N-{4-[(3R,4R,5S)-3-Amino-4-hydroxy-5-methylpiperidin-1-yl]pyridin-3-yl}-7-ethylquinoline-2-carboxamide

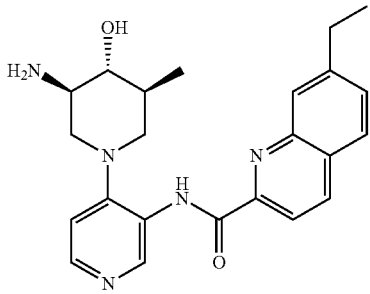 [SMILES: CCc1ccc2ccc(C(=O)Nc3cnccc3N3C[C@@H](N)[C@H](O)[C@@H](C)C3)nc2c1]

Step 1. tert-Butyl ((3R,4R,5S)-1-(3-{[(7-bromoquinolin-2-yl)carbonyl]amino}pyridin-4-yl)-4-{[tert-butyl(dimethyl)silyl]oxy}-5-methylpiperidin-3-yl)carbamate

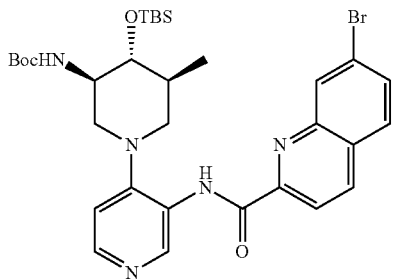 [SMILES: C[C@H]1CN(c2ccncc2NC(=O)c2ccc3ccc(Br)cc3n2)C[C@@H](NC(=O)OC(C)(C)C)[C@@H]1O[Si](C)(C)C(C)(C)C]

To a mixture of 7-bromoquinoline-2-carboxylic acid (Aldrich, 158.1 mg, 0.6272 mmol), tert-butyl ((3R,4R,5S)-1-(3-aminopyridin-4-yl)-4-{[tert-butyl(dimethyl)silyl]oxy}-5-methylpiperidin-3-yl)carbamate (281.0 mg, 0.6434 mmol) and HATU (715.0 mg, 1.88 mmol) was added DMF (4.0 mL) followed by DIPEA (407.9 mg, 3.156 mmol). After stirring at room temperature for 3 h, the reaction was concentrated under reduced pressure. The residue was purified on silica gel (40 g, 0-100% EtOAc in hexanes) to give the sub-title product as a yellow solid (375.4 mg, 89%). LCMS calc. for $C_{32}H_{45}BrN_5O_4Si$ (M+H)⁺: m/z=670.2; found 670.3.

Step 2. tert-Butyl [(3R,4R,5S)-4-{[tert-butyl(dimethyl)silyl]oxy}-5-methyl-1-(3-{[(7-vinylquinolin-2-yl)carbonyl]amino}pyridin-4-yl)piperidin-3-yl]carbamate

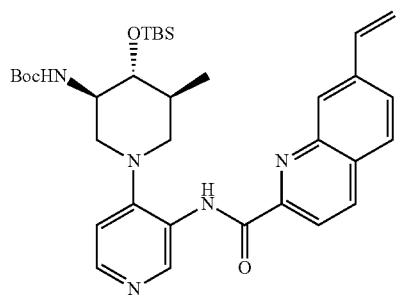 [SMILES: C=Cc1ccc2ccc(C(=O)Nc3cnccc3N3C[C@H](C)[C@@H](O[Si](C)(C)C(C)(C)C)[C@H](NC(=O)OC(C)(C)C)C3)nc2c1]

To a screw-cap vial equipped with a magnetic stir bar was added tert-butyl ((3R,4R,5S)-1-(3-{[(7-bromoquinolin-2-yl)carbonyl]amino}pyridin-4-yl)-4-{[tert-butyl(dimethyl)silyl]oxy}-5-methylpiperidin-3-yl)carbamate (287.6 mg, 0.4288 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 34.2 mg, 0.0435 mmol), and $K_3PO_4$ (396.1 mg, 1.866 mmol). The vial was sealed with a PTFE-lined septum, evacuated, and backfilled with N₂ (this process was repeated a total of three times). A solution of 4,4,5,5-tetramethyl-2-vinyl-1,3,2-dioxaborolane (Aldrich, 198.4 mg, 1.288 mmol) in 1,4-dioxane (3.00 mL) was added followed by deoxygenated water (1.00 mL). The reaction mixture was stirred at 80° C. for 1 h. After cooling to room temperature, the reaction was filtered through a silica gel plug (eluted with EtOAc). The filtrate was washed with brine, dried over $Na_2SO_4$, filtered, and concentrated. The resulting residue was purified on silica gel (40 g, 0-100% EtOAc in hexanes) to give the sub-title product as a red semi-solid (257.1 mg, 97%). LCMS calc. for $C_{34}H_{48}N_5O_4Si$ (M+H)⁺: m/z=618.3; found 618.3.

Step 3. N-{4-[(3R,4R,5S)-3-Amino-4-hydroxy-5-methylpiperidin-1-yl]pyridin-3-yl}-7-ethylquinoline-2-carboxamide To a solution of tert-butyl [(3R,4R,5S)-4-{[tert-butyl(dimethyl)silyl]oxy}-5-methyl-1-(3-{[(7-vinylquinolin-2-yl)carbonyl]amino}pyridin-4-yl)piperidin-3-yl]carbamate (257.1 mg, 0.4161 mmol) in MeOH (3.00 mL) was added 10 wt % Pd on carbon (95.6 mg). The mixture was stirred at room temperature under H₂ atmosphere (1 atm) for 15 h. The reaction was then filtered through a pad of diatomaceous earth (eluted with MeOH), and concentrated. To the resulting residue was added 4.0 M HCl in dioxane (7.00 mL, 28.0 mmol). After stirring at room temperature for 3 h, the reaction mixture was concentrated. The residue was purified using RP-HPLC (XBridge™ C18 column, eluting with a gradient of MeCN/water containing 0.1% NH₄OH, at flow rate of 30 mL/min.) to afford the title product as a white solid (47.6 mg, 28%). LCMS calc. for $C_{23}H_{28}N_5O_2$ (M+H)⁺: m/z=406.2; found 406.3.

Example 10

N-{4-[(3R,4R,5S)-3-Amino-4-hydroxy-5-methylpiperidin-1-yl]pyridin-3-yl}-7-isopropylquinoline-2-carboxamide

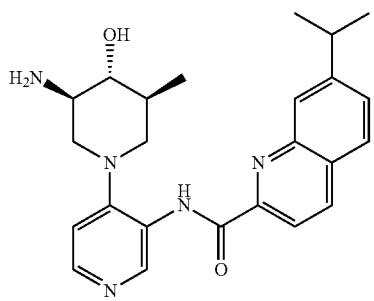 [SMILES: CC(C)c1ccc2ccc(C(=O)Nc3cnccc3N3C[C@@H](N)[C@H](O)[C@@H](C)C3)nc2c1]

Step 1. tert-Butyl [(3R,4R,5S)-4-{[tert-butyl(dimethyl)silyl]oxy}-1-(3-{[(7-isopropenylquinolin-2-yl)carbonyl]amino}pyridin-4-yl)-5-methylpiperidin-3-yl]carbamate

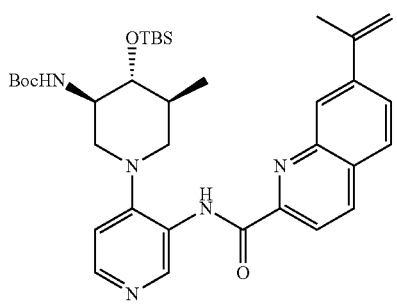 [SMILES: C=C(C)c1ccc2ccc(C(=O)Nc3cnccc3N3C[C@H](C)[C@@H](O[Si](C)(C)C(C)(C)C)[C@H](NC(=O)OC(C)(C)C)C3)nc2c1]

To a screw-cap vial equipped with a magnetic stir bar was added tert-butyl ((3R,4R,5S)-1-(3-{[(7-bromoquinolin-2-yl)carbonyl]amino}pyridin-4-yl)-4-{[tert-butyl(dimethyl)silyl]oxy}-5-methylpiperidin-3-yl)carbamate (from Example 8, Step 1, 275.3 mg, 0.4104 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 29.3 mg, 0.0372 mmol), and $K_3PO_4$ (380.0 mg, 1.790 mmol). The vial was sealed with a PTFE-lined septum, evacuated, and backfilled with $N_2$ (this process was repeated a total of three times). A solution of 2-isopropenyl-4,4,5,5-tetramethyl-1,3,2-dioxaborolane (215.7 mg, 1.284 mmol) in 1,4-dioxane (3.00 mL) was added, followed by deoxygenated water (1.00 mL). The reaction mixture was stirred at 80° C. for 1 h. After cooling to room temperature, the reaction was filtered through a pad of diatomaceous earth (eluted with EtOAc). The filtrate was washed with brine, dried over $Na_2SO_4$, filtered, and concentrated. The resulting residue was purified on silica gel (40 g, 0-100% EtOAc in hexanes) to give the sub-title product as a yellow foamy solid (206.1 mg, 79%). LCMS calc. for $C_{35}H_{50}N_5O_4Si$ $(M+H)^+$: m/z=632.4; found 632.4.

Step 2. N-{4-[(3R,4R,5S)-3-Amino-4-hydroxy-5-methylpiperidin-1-yl]pyridin-3-yl}-7-isopropylquinoline-2-carboxamide To a solution of tert-butyl [(3R,4R,5S)-4-{[tert-butyl(dimethyl)silyl]oxy}-1-(3-{[(7-isopropenylquinolin-2-yl)carbonyl]amino}pyridin-4-yl)-5-methylpiperidin-3-yl]carbamate (206.1 mg, 0.3262 mmol) in MeOH (3.00 mL) was added 10 wt % Pd on carbon (85.6 mg). The mixture was stirred at room temperature under $H_2$ atmosphere (1 atm) for 15 h. The reaction was then filtered through a pad of diatomaceous earth (eluted with MeOH), and concentrated. To the resulting residue was added 4.0 M HCl in dioxane (5.00 mL, 20.0 mmol). After stirring at room temperature for 3 h, the reaction mixture was concentrated. The residue was purified using RP-HPLC (XBridge™ C18 column, eluting with a gradient of MeCN/water containing 0.1% $NH_4OH$, at flow rate of 30 mL/min.) to afford the title product as a white solid (70.8 mg, 52%). LCMS calc. for $C_{24}H_{30}N_5O_2$ $(M+H)^+$: m/z=420.2; found 420.2. $^1H$ NMR (500 MHz, DMSO-$d_6$) δ 10.64 (s, 1H), 9.48 (s, 1H), 8.61 (d, J=8.4 Hz, 1H), 8.26 (d, J=5.3 Hz, 1H), 8.23 (d, J=8.4 Hz, 1H), 8.05 (d, J=8.5 Hz, 1H), 8.00 (s, 1H), 7.70 (d, J=8.5, 1H), 7.15 (d, J=5.3 Hz, 1H), 4.98 (d, J=4.8 Hz, 1H), 3.34-3.03 (m, 4H), 2.81 (m, 1H), 2.58 (t, J=11.0 Hz, 1H), 2.48 (t, J=11.0 Hz, 1H), 2.25-2.10 (m, 1H), 1.62 (br, 2H), 1.35 (d, J=6.9 Hz, 6H), 0.92 (d, J=6.6 Hz, 3H) ppm.

Example 11

N-{4-[(3R,4R,5S)-3-Amino-4-hydroxy-5-methylpiperidin-1-yl]pyridin-3-yl}-7-(tetrahydro-2H-pyran-4-yl)quinoline-2-carboxamide

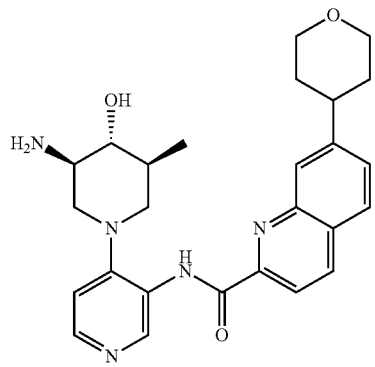

Step 1. tert-Butyl {(3R,4R,5S)-4-{[tert-butyl(dimethyl)silyl]oxy}-1-[3-({[7-(3,6-dihydro-2H-pyran-4-yl)quinolin-2-yl]carbonyl}amino)pyridin-4-yl]-5-methylpiperidin-3-yl}carbamate

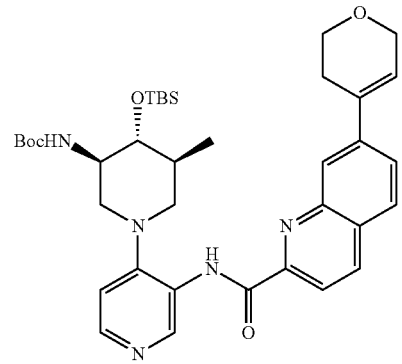 [SMILES: C[C@H]1CN(c2ccncc2NC(=O)c2ccc3ccc(C4=CCOCC4)cc3n2)C[C@@H](NC(=O)OC(C)(C)C)[C@@H]1O[Si](C)(C)C(C)(C)C]

To a screw-cap vial equipped with a magnetic stir bar was added tert-butyl ((3R,4R,5S)-1-(3-{[(7-bromoquinolin-2-yl)carbonyl]amino}pyridin-4-yl)-4-{[tert-butyl(dimethyl)silyl]oxy}-5-methylpiperidin-3-yl)carbamate (from Example 8, Step 1, 190.5 mg, 0.2840 mmol), 4-(4,4,5,5-tetramethyl-1,3,2-dioxaborolan-2-yl)-3,6-dihydro-2H-pyran (Aldrich, 118.0 mg, 0.5617 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 26.7 mg, 0.0339 mmol), and $K_3PO_4$ (207.0 mg, 0.9752 mmol). The vial was sealed with a PTFE-lined septum, evacuated, and backfilled with $N_2$ (this process was repeated a total of three times). 1,4-Dioxane (3.00 mL) was added, followed by deoxygenated water (1.00 mL). The reaction mixture was stirred at 80° C. for 1 h. After cooling to room temperature, the reaction was filtered through a pad of diatomaceous earth (eluted with EtOAc). The filtrate was washed with brine, dried over $Na_2SO_4$, filtered, and concentrated. The resulting residue was purified on silica gel (40 g, 0-100% EtOAc in hexanes) to give the sub-title product as a yellow foamy solid (123.2 mg, 64%). LCMS calc. for $C_{37}H_{52}N_5O_5Si$ (M+H)$^+$: m/z=674.4; found 674.3.

Step 2. N-{4-[(3R,4R,5S)-3-Amino-4-hydroxy-5-methylpiperidin-1-yl]pyridin-3-yl}-7-(tetrahydro-2H-pyran-4-yl)quinoline-2-carboxamide To a solution of tert-butyl {(3R,4R,5S)-4-{[tert-butyl(dimethyl)silyl]oxy}-1-[3-({[7-(3,6-dihydro-2H-pyran-4-yl)quinolin-2-yl]carbonyl}amino)pyridin-4-yl]-5-methylpiperidin-3-yl}carbamate (123.2 mg, 0.1828 mmol) in MeOH (2.00 mL) was added 10 wt % Pd on carbon (48.8 mg). The mixture was stirred at room temperature under $H_2$ atmosphere (1 atm.) for 15 h. The reaction mixture was then filtered through a pad of diatomaceous earth (eluted with MeOH), and concentrated. To the resulting residue was added 4.0 M HCl in dioxane (5.00 mL, 20.0 mmol). After stirring at room temperature for 3 h, the reaction mixture was concentrated. The residue was purified using RP-HPLC (XBridge™ C18 column, eluting with a gradient of MeCN/water containing 0.1% $NH_4OH$, at flow rate of 30 mL/min.) to afford the title product as a white solid (46.4 mg, 55%). LCMS calc. for $C_{26}H_{32}N_5O_3$ (M+H)$^+$: m/z=462.3; found 462.2.

Example 12

N-{4-[(3R,4R,5S)-3-Amino-4-hydroxy-5-methylpiperidin-1-yl]pyridin-3-yl}-7-morpholin-4-ylquinoline-2-carboxamide

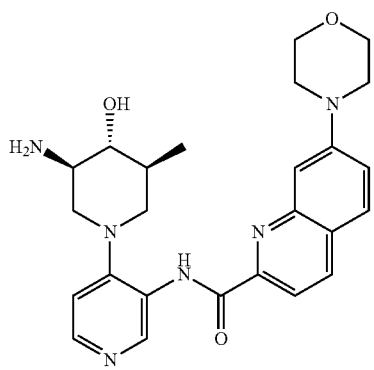 [SMILES: C[C@H]1CN(c2ccncc2NC(=O)c2ccc3ccc(N4CCOCC4)cc3n2)C[C@@H](N)[C@@H]1O]

Step 1. Methyl 7-bromoquinoline-2-carboxylate

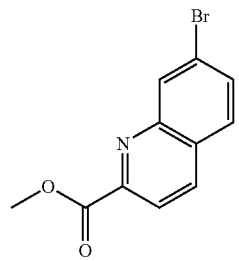

To a mixture of 7-bromoquinoline-2-carboxylic acid (4.25 g, 16.9 mmol) and $K_2CO_3$ (3.54 g, 25.6 mmol) was added DMF (20.0 mL). The mixture was cooled to 0° C. Then a solution of MeI (2.89 g, 20.4 mmol) in DMF (11.0 mL) was added slowly. The reaction mixture was allowed to warm to room temperature. After stirring at room temperature for 16 h, the reaction mixture was poured into water (150 mL) and extracted with EtOAc (3×100 mL). The combined organic layers were washed with brine, dried over $Na_2SO_4$, filtered, and concentrated. The resulting residue was purified on silica gel (120 g, 0-50% DCM in EtOAc) to give the sub-title product as a pale yellow solid (4.07 g, 91%). LCMS calc. for $C_{11}H_9BrNO_2$ (M+H)$^+$: m/z=266.0; found 265.9.

Step 2. 7-Morpholin-4-ylquinoline-2-carboxylic acid

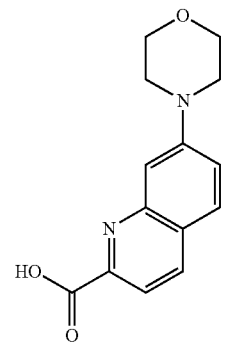 [SMILES: O=C(O)c1ccc2ccc(N3CCOCC3)cc2n1]

To a screw-cap vial equipped with a magnetic stir bar was added methyl 7-bromoquinoline-2-carboxylate (438.2 mg, 1.647 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 112.0 mg, 0.1442 mmol), and $Cs_2CO_3$ (1.752 g, 5.377 mmol). The vial was sealed with a PTFE-lined septum, evacuated and backfilled with $N_2$ (this process was repeated a total of three times). A solution of morpholine (251.6 mg, 2.888 mmol) in anhydrous t-BuOH (6.00 mL) was added via syringe. The mixture was heated to 100° C. for 10 h. After cooling to room temperature, the reaction mixture was poured into brine (50 mL) and extracted with EtOAc (3×50 mL). The aqueous layer was acidified to pH 4 with AcOH. Then it was extracted with DCM (10×50 mL). The combined organic layer was dried over $Na_2SO_4$, filtered, and concentrated to give the crude product as a yellow solid (405.1 mg) which was used directly in the next step without further purification. LCMS calc. for $C_{14}H_{15}N_2O_3$ (M+H)$^+$: m/z=259.1; found 259.1.

Step 3. N-{4-[(3R,4R,5S)-3-Amino-4-hydroxy-5-methylpiperidin-1-yl]pyridin-3-yl}-7-morpholin-4-ylquinoline-2-carboxamide To a mixture of 7-morpholin-4-ylquinoline-2-carboxylic acid (70.0 mg, 0.271 mmol), tert-butyl ((3R,4R,5S)-1-(3-aminopyridin-4-yl)-4-{[tert-butyl(dimethyl)silyl]oxy}-5-methylpiperidin-3-yl)carbamate (122.2 mg, 0.2798 mmol) and HATU (318.5 mg, 0.8376 mmol) was added DMF (2.50 mL) followed by DIPEA (198.5 mg, 1.536 mmol). After stirring at room temperature for 1 h, the reaction was concentrated under reduced pressure. The residue was purified on silica gel (40 g, 0-100% EtOAc in hexanes) to give a brown semi-oil. To this brown semi-oil was added 4.0 M HCl in dioxane (4.00 mL, 16.0 mmol). The mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (45.1 mg, 36%). LCMS calc. for C$_{25}$H$_{31}$N$_6$O$_3$ (M+H)$^+$: m/z=463.2; found 463.2. $^1$H NMR (500 MHz, DMSO-d$_6$) δ 10.79 (s, 1H), 9.53 (s, 1H), 8.45 (d, J=8.3 Hz, 1H), 8.26 (d, J=5.3 Hz, 1H), 8.02 (d, J=8.2 Hz, 1H), 7.94 (d, J=9.2 Hz, 1H), 7.63 (dd, J=9.2, 2.3 Hz, 1H), 7.34 (d, J=2.3 Hz, 1H), 7.16 (d, J=5.3 Hz, 1H), 5.06 (d, J=4.3 Hz, 1H), 3.82-3.78 (m, 4H), 3.38 (m, 4H), 3.23 (m, 1H), 3.19-3.10 (m, 2H), 2.83 (m, 1H), 2.58 (t, J=10.9 Hz, 1H), 2.49 (m, 1H), 2.30-2.14 (m, 1H), 1.63 (br, 2H), 0.93 (d, J=6.6 Hz, 3H) ppm.

Example 13

N-{4-[(3S,5R)-3-Amino-5-methylpiperidin-1-yl]pyridin-3-yl}-7-morpholin-4-ylquinoline-2-carboxamide

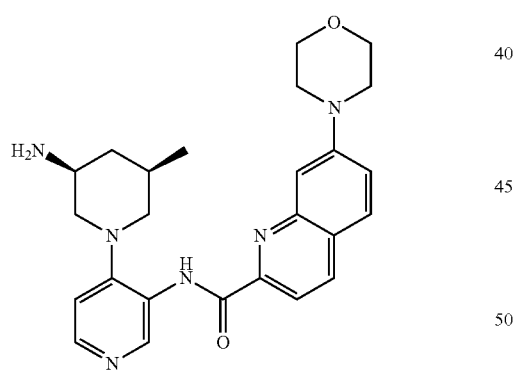

To a mixture of 7-morpholin-4-ylquinoline-2-carboxylic acid (70.0 mg, 0.271 mmol), tert-butyl [(3S,5R)-1-(3-aminopyridin-4-yl)-5-methylpiperidin-3-yl]carbamate (84.6 mg, 0.276 mmol) and HATU (315.0 mg, 0.8284 mmol) was added DMF (2.50 mL) followed by DIPEA (195.4 mg, 1.512 mmol). After stirring at room temperature for 1 h, the reaction was concentrated under reduced pressure. The residue was purified on silica gel (40 g, 5% MeOH in DCM) to give a brown semi-oil. To this brown semi-oil was added DCM (2.00 mL), and TFA (2.00 mL). The mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (33.2 mg, 27%). LCMS calc. for C$_{25}$H$_{31}$N$_6$O$_2$ (M+H)$^+$: m/z=447.3; found 447.2. $^1$H NMR (500 MHz, DMSO-d$_6$) δ 10.66 (s, 1H), 9.47 (s, 1H), 8.45 (d, J=8.3 Hz, 1H), 8.26 (d, J=5.3 Hz, 1H), 8.03 (d, J=8.2 Hz, 1H), 7.95 (d, J=9.2 Hz, 1H), 7.65 (dd, J=9.1, 2.2 Hz, 1H), 7.26 (d, J=2.2 Hz, 1H), 7.15 (d, J=5.3 Hz, 1H), 3.83 (m, 4H), 3.36 (m, 4H), 3.33-3.13 (m, 3H), 2.29 (m, 2H), 2.25-2.14 (m, 1H), 2.03 (m, 1H), 1.60 (br, 2H), 0.88 (m, 4H) ppm.

Example 14

N-{4-[(3R,4R,5S)-3-Amino-4-hydroxy-5-methylpiperidin-1-yl]pyridin-3-yl}-7-(3-oxa-9-azaspiro[5.5]undec-9-yl)quinoline-2-carboxamide

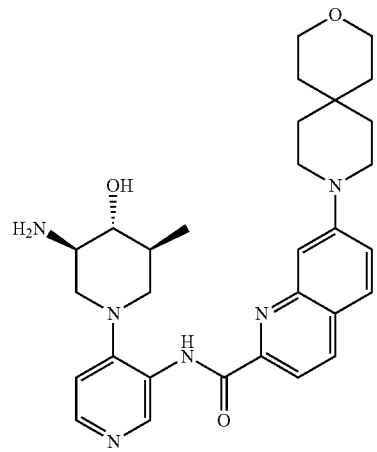 [SMILES: C[C@H]1CN(c2ccncc2NC(=O)c2ccc3ccc(N4CCC5(CCOCC5)CC4)cc3n2)C[C@@H](N)[C@@H]1O]

Step 1. 7-(3-Oxa-9-azaspiro[5.5]undec-9-yl)quinoline-2-carboxylic acid

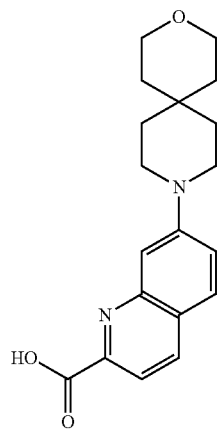 [SMILES: O=C(O)c1ccc2ccc(N3CCC4(CCOCC4)CC3)cc2n1]

To a screw-cap vial equipped with a magnetic stir bar was added methyl 7-bromoquinoline-2-carboxylate (256.2 mg, 0.9628 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 72.9 mg, 0.0939 mmol), and Cs$_2$CO$_3$ (1.005 g, 3.084 mmol). The vial was sealed with a PTFE-lined septum, evacuated and backfilled with N$_2$ (this process was repeated a total of three times). A solution of 3-oxa-9-azaspiro[5.5]undecane (273.0 mg, 1.758 mmol) in anhydrous t-BuOH (4.00 mL) was added via syringe. The mixture was heated to 100° C. for 10 h. After cooling to room temperature, the reaction mixture was poured into brine (50 mL) and extracted with EtOAc (3×50 mL). The aqueous layer was acidified to pH 4 with AcOH. Then it was extracted with DCM (10×50 mL). The combined organic layer was dried over $Na_2SO_4$, filtered, and concentrated to give the crude product as a yellow solid (310.6 mg) which was used directly in the next step without further purification. LCMS calc. for $C_{19}H_{23}N_2O_3$ (M+H)$^+$: m/z=327.2; found 327.1.

Step 2. N-{4-[(3R,4R,5S)-3-Amino-4-hydroxy-5-methylpiperidin-1-yl]pyridin-3-yl}-7-(3-oxa-9-azaspiro[5.5]undec-9-yl)quinoline-2-carboxamide To a mixture of 7-(3-oxa-9-azaspiro[5.5]undec-9-yl)quinoline-2-carboxylic acid (95.5 mg, 0.292 mmol), tert-butyl ((3R,4R,5S)-1-(3-aminopyridin-4-yl)-4-{[tert-butyl(dimethyl)silyl]oxy}-5-methylpiperidin-3-yl)carbamate (139.2 mg, 0.3188 mmol) and HATU (361.6 mg, 0.9510 mmol) was added DMF (2.00 mL) followed by DIPEA (300.0 μL, 1.722 mmol). After stirring at room temperature for 2 h, the reaction was concentrated under reduced pressure. The residue was purified on silica gel (40 g, 0-100% EtOAc in hexanes) to give a brown semi-oil. To this brown semi-oil was added 4.0 M HCl in dioxane (4.00 mL, 16.0 mmol). The mixture was stirred at room temperature for 2 h, and was then concentrated under reduced pressure. The residue was purified using RP-HPLC (XBridge™ C18 column, eluting with a gradient of MeCN/water containing 0.1% $NH_4OH$, at flow rate of 30 mL/min.) to afford the title product as a yellow solid (62.1 mg, 40%). LCMS calc. for $C_{30}H_{39}N_6O_3$ (M+H)$^+$: m/z=531.3; found 531.3. $^1$H NMR (500 MHz, DMSO-$d_6$) δ 10.76 (s, 1H), 9.53 (s, 1H), 8.39 (d, J=8.2 Hz, 1H), 8.25 (d, J=5.2 Hz, 1H), 7.96 (d, J=8.2 Hz, 1H), 7.88 (d, J=9.2 Hz, 1H), 7.60 (dd, J=9.2, 2.5 Hz, 1H), 7.32 (d, J=2.4 Hz, 1H), 7.15 (d, J=5.3 Hz, 1H), 5.06 (s, 1H), 3.64-3.54 (m, 4H), 3.49-3.41 (m, 4H), 3.25-3.20 (m, 1H), 3.20-3.14 (m, 1H), 3.14-3.07 (m, 1H), 2.83 (m, 1H), 2.58 (t, J=10.9 Hz, 1H), 2.49 (m, 1H), 2.28-2.13 (m, 1H), 1.70-1.56 (m, 6H), 1.53-1.43 (m, 4H), 0.93 (d, J=6.6 Hz, 3H) ppm.

Example 15

N-{4-[(3S,5R)-3-Amino-5-methylpiperidin-1-yl]pyridin-3-yl}-7-(3-oxa-9-azaspiro[5.5]undec-9-yl)quinoline-2-carboxamide

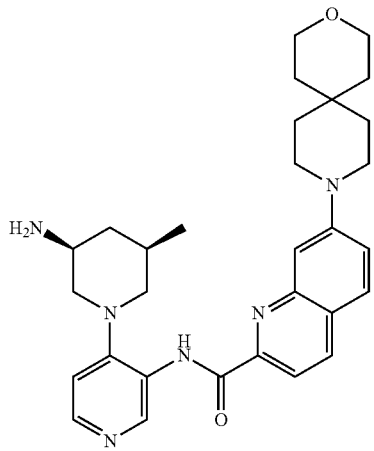 [SMILES: C[C@@H]1C[C@H](N)CN(c2ccncc2NC(=O)c2ccc3ccc(N4CCC5(CCOCC5)CC4)cc3n2)C1]

To a mixture of 7-(3-oxa-9-azaspiro[5.5]undec-9-yl)quinoline-2-carboxylic acid (96.8 mg, 0.296 mmol), tert-butyl [(3S,5R)-1-(3-aminopyridin-4-yl)-5-methylpiperidin-3-yl]carbamate (103.4 mg, 0.3375 mmol) and HATU (351.6 mg, 0.9247 mmol) was added DMF (2.00 mL) followed by DIPEA (300.0 μL, 1.722 mmol). After stirring at room temperature for 2 h, the reaction was diluted with EtOAc. The mixture was washed with water, and brine. The organic layer was dried over $Na_2SO_4$, filtered, and concentrated. To the resulting residue was added DCM (2.00 mL) and TFA (2.00 mL). The reaction mixture was stirred at room temperature for 2 h, and then concentrated. The residue was purified using RP-HPLC (XBridge™ C18 column, eluting with a gradient of MeCN/water containing 0.1% $NH_4OH$, at flow rate of 30 mL/min.) to afford the title product as a yellow solid (62.4 mg, 41%). LCMS calc. for $C_{30}H_{39}N_6O_2$ (M+H)$^+$: m/z=515.3; found 515.3.

Example 16

N-{4-[(3R,4R,5S)-3-Amino-4-hydroxy-5-methylpiperidin-1-yl]pyridin-3-yl}-7-(4-cyanopiperidin-1-yl)quinoline-2-carboxamide

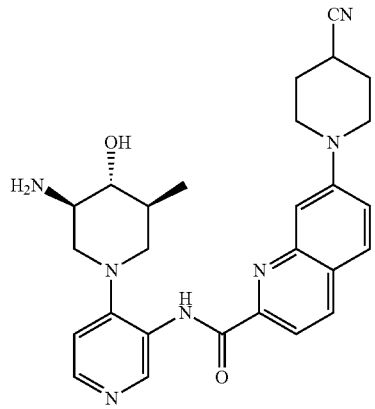 [SMILES: C[C@H]1CN(c2ccncc2NC(=O)c2ccc3ccc(N4CCC(C#N)CC4)cc3n2)C[C@@H](N)[C@@H]1O]

Step 1.
7-(4-Cyanopiperidin-1-yl)quinoline-2-carboxylic acid [1.0]-trifluoroacetic acid

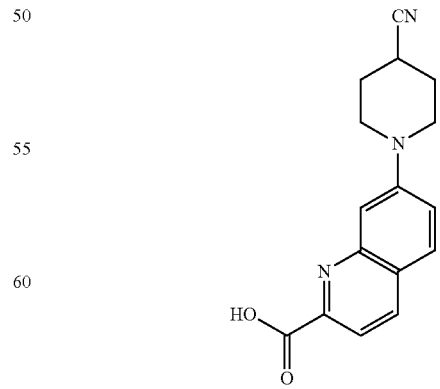

To a screw-cap vial equipped with a magnetic stir bar was added methyl 7-bromoquinoline-2-carboxylate (240.4 mg, 0.9034 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 81.7 mg, 0.1052 mmol), and Cs$_2$CO$_3$ (893.0 mg, 2.741 mmol). The vial was sealed with a PTFE-lined septum, evacuated and backfilled with N$_2$ (this process was repeated a total of three times). A solution of piperidine-4-carbonitrile (181.0 mg, 1.643 mmol) in anhydrous t-BuOH (6.00 mL) was added via syringe. The mixture was heated to 100° C. for 10 h. After cooling to room temperature, the reaction mixture was diluted with MeOH (20 mL). AcOH (1.00 mL, 17.6 mmol) was added. The mixture was filtered through a pad of diatomaceous earth (eluted with MeOH). The filtrate was concentrated under reduced pressure, and the residue was purified using RP-HPLC (XBridge™ C18 column, eluting with a gradient of MeCN/water containing 0.05% TFA, at flow rate of 30 mL/min.) to afford the title product as a red solid (126.4 mg, 35%). LCMS calc. for C$_{16}$H$_{16}$N$_3$O$_2$ (M+H)$^+$: m/z=282.1; found 282.1.

Step 2. N-{4-[(3R,4R,5S)-3-Amino-4-hydroxy-5-methylpiperidin-1-yl]pyridin-3-yl}-7-(4-cyanopiperidin-1-yl)quinoline-2-carboxamide To a mixture of 7-(4-cyanopiperidin-1-yl)quinoline-2-carboxylic acid [1.0]-trifluoroacetic acid (62.5 mg, 0.158 mmol), tert-butyl ((3R,4R,5S)-1-(3-aminopyridin-4-yl)-4-{[tert-butyl(dimethyl)silyl]oxy}-5-methylpiperidin-3-yl)carbamate (91.4 mg, 0.209 mmol) and HATU (219.1 mg, 0.5762 mmol) was added DMF (2.00 mL) followed by DIPEA (180.0 mg, 1.393 mmol). After stirring at room temperature for 18 h, the reaction was diluted with EtOAc. The mixture was washed with water and brine. The organic layer was dried over Na$_2$SO$_4$, filtered, and concentrated. To the resulting residue was added 4.0 M HCl in dioxane (4.00 mL, 16.0 mmol). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (42.8 mg, 56%). LCMS calc. for C$_{27}$H$_{32}$N$_7$O$_2$ (M+H)$^+$: m/z=486.3; found 486.3.

Example 17

N-{4-[(3S,5R)-3-Amino-5-methylpiperidin-1-yl]pyridin-3-yl}-7-(4-cyanopiperidin-1-yl)quinoline-2-carboxamide

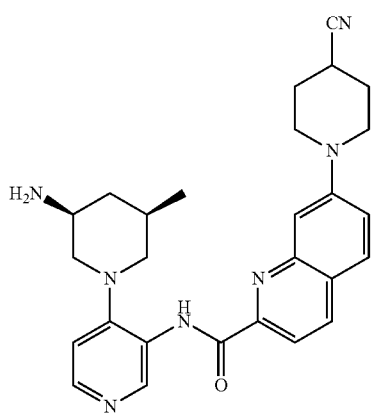 [SMILES: C[C@@H]1C[C@H](N)CN(c2ccncc2NC(=O)c2ccc3ccc(N4CCC(C#N)CC4)cc3n2)C1]

To a mixture of 7-(4-cyanopiperidin-1-yl)quinoline-2-carboxylic acid [1.0]-trifluoroacetic acid (57.3 mg, 0.145 mmol), tert-butyl [(3S,5R)-1-(3-aminopyridin-4-yl)-5-methylpiperidin-3-yl]carbamate (55.1 mg, 0.180 mmol) and HATU (196.1 mg, 0.5157 mmol) was added DMF (2.00 mL) followed by DIPEA (163.8 mg, 1.267 mmol). After stirring at room temperature for 18 h, the reaction mixture was diluted with EtOAc. The mixture was washed with water and brine. The organic layer was dried over Na$_2$SO$_4$, filtered, and concentrated. To the resulting residue was added DCM (2.00 mL) and TFA (2.00 mL). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (41.9 mg, 62%). LCMS calc. for C$_{27}$H$_{32}$N$_7$O (M+H)$^+$: m/z=470.3; found 470.2.

Example 18

N-{4-[(3R,4R,5S)-3-Amino-4-hydroxy-5-methylpiperidin-1-yl]pyridin-3-yl}-7-(4-methylpiperazin-1-yl)quinoline-2-carboxamide

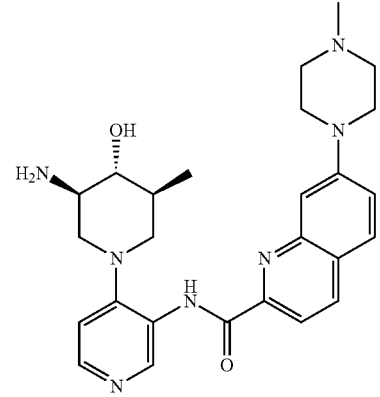 [SMILES: C[C@H]1CN(c2ccncc2NC(=O)c2ccc3ccc(N4CCN(C)CC4)cc3n2)C[C@@H](N)[C@@H]1O]

Step 1.
7-(4-Methylpiperazin-1-yl)quinoline-2-carboxylic acid [1.0]-trifltioroacetic acid

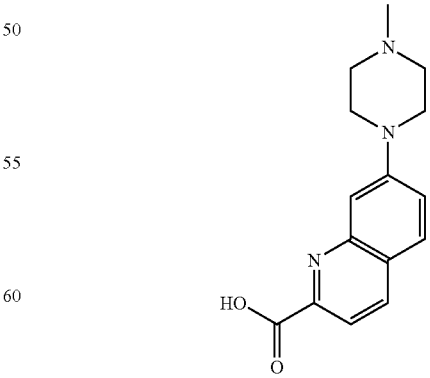

To a screw-cap vial equipped with a magnetic stir bar was added methyl 7-bromoquinoline-2-carboxylate (158.7 mg, 0.5964 mmol), dicyclohexyl(2',6'-diisopropoxybiphenyl-2- yl)phosphine-(2'-aminobiphenyl-2-yl)(chloro)palladium (1:1) (RuPhos Pd G2, Aldrich, 52.9 mg, 0.0681 mmol), and Cs$_2$CO$_3$ (602.4 mg, 1.849 mmol). The vial was sealed with a PTFE-lined septum, evacuated, and backfilled with N$_2$ (this process was repeated a total of three times). A solution of 1-methylpiperazine (125.7 mg, 1.255 mmol) in anhydrous t-BuOH (4.00 mL) was added via syringe. The mixture was heated to 100° C. for 10 h. After cooling to room temperature, the reaction mixture was diluted with MeOH (20 mL). AcOH (1.00 mL, 17.6 mmol) was added. The mixture was filtered through a pad of diatomaceous earth (eluted with MeOH). The filtrate was concentrated under reduced pressure, and the residue was purified using RP-HPLC (XBridge™ C18 column, eluting with a gradient of MeCN/water containing 0.05% TFA, at flow rate of 30 mL/min.) to afford the title product as a red solid (180.2 mg, 78%). LCMS calc. for C$_{15}$H$_{18}$N$_3$O$_2$ (M+H)$^+$: m/z=272.1; found 272.1.

Step 2. N-{4-[(3R,4R,5S)-3-Amino-4-hydroxy-5-methylpiperidin-1-yl]pyridin-3-yl}-7-(4-methylpiperazin-1-yl)quinoline-2-carboxamide To a mixture of 7-(4-methylpiperazin-1-yl)quinoline-2-carboxylic acid [1.0]-trifluoroacetic acid (90.3 mg, 0.234 mmol), tert-butyl ((3R,4R,5S)-1-(3-aminopyridin-4-yl)-4-{[tert-butyl(dimethyl)silyl]oxy}-5-methylpiperidin-3-yl) carbamate (94.6 mg, 0.217 mmol) and HATU (258.1 mg, 0.6788 mmol) was added DMF (2.00 mL) followed by DIPEA (237.3 mg, 1.836 mmol). After stirring at room temperature for 18 h, the reaction was diluted with EtOAc. The mixture was washed with water, and brine. The organic layer was dried over Na$_2$SO$_4$, filtered, and concentrated. To the resulting residue was added 0.4.0 M HCl in dioxane (4.00 mL, 16.0 mmol). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (22.7 mg, 22%). LCMS calc. for C$_{26}$H$_{34}$N$_7$O$_2$ (M+H)$^+$: m/z=476.3; found 476.3.

Example 19

N-{4-[(3S,5R)-3-Amino-5-methylpiperidin-1-yl]pyridin-3-yl}-7-(4-methylpiperazin-1-yl)quinoline-2-carboxamide

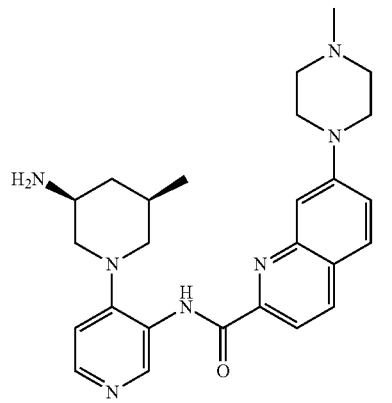 [SMILES: C[C@@H]1C[C@H](N)CN(c2ccncc2NC(=O)c2ccc3ccc(N4CCN(C)CC4)cc3n2)C1]

To a mixture of 7-(4-methylpiperazin-1-yl)quinoline-2-carboxylic acid [1.0]-trifluoroacetic acid (78.4 mg, 0.203 mmol), tert-butyl [(3S,5R)-1-(3-aminopyridin-4-yl)-5-methylpiperidin-3-yl]carbamate (53.7 mg, 0.175 mmol) and HATU (238.7 mg, 0.6278 mmol) was added DMF (2.00 mL) followed by DIPEA (196.1 mg, 1.517 mmol). After stirring at room temperature for 18 h, the reaction was diluted with EtOAc. The mixture was washed with water, and brine. The organic layer was dried over Na$_2$SO$_4$, filtered, and concentrated. To the resulting residue was added DCM (2.00 mL) and TFA (2.00 mL). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (24.9 mg, 31%). LCMS calc. for C$_{26}$H$_{34}$N$_7$O (M+H)$^+$: m/z=460.3; found 460.3.

Example 20

N-{4-[(3R,4R,5S)-3-Amino-4-hydroxy-5-methylpiperidin-1-yl]pyridin-3-yl}-7-(4-pyridin-4-ylpiperidin-1-yl)quinoline-2-carboxamide

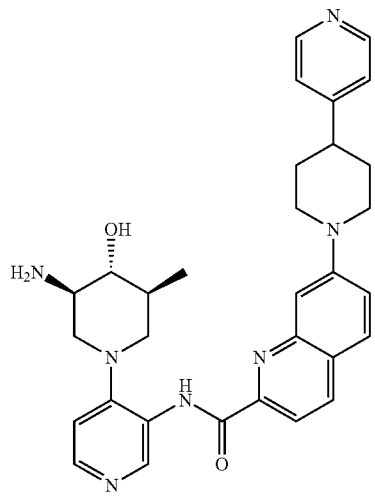 [SMILES: C[C@H]1CN(c2ccncc2NC(=O)c2ccc3ccc(N4CCC(c5ccncc5)CC4)cc3n2)C[C@@H](N)[C@@H]1O]

Step 1. 7-(4-Pyridin-4-ylpiperidin-1-yl)quinoline-2-carboxylic acid [1.0]-trifluoroacetic acid

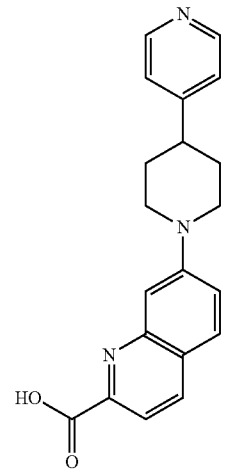 [SMILES: O=C(O)c1ccc2ccc(N3CCC(c4ccncc4)CC3)cc2n1]

To a screw-cap vial equipped with a magnetic stir bar was added methyl 7-bromoquinoline-2-carboxylate (245.1 mg, 0.9211 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 74.5 mg, 0.0959 mmol), 4-piperidin-4-ylpyridine [1.0]-HCl (340.8 mg, 1.715 mmol), and Cs$_2$CO$_3$ (1.811 g, 5.558 mmol). The vial was sealed with a PTFE-lined septum, evacuated, and backfilled with N$_2$ (this process was repeated a total of three times). Anhydrous t-BuOH (6.00 mL) was added via syringe. The mixture was heated at 100° C. for 10 h. After cooling to room temperature, the reaction mixture was diluted with MeOH (20 mL). AcOH (1.00 mL, 17.6 mmol) was added. The mixture was filtered through a pad of diatomaceous earth (eluted with MeOH). The filtrate was concentrated under reduced pressure, and the residue was purified using RP-HPLC (XBridge™ C18 column, eluting with a gradient of MeCN/water containing 0.05% TFA, at flow rate of 30 mL/min.) to afford the title product as a red solid (184.8 mg, 45%). LCMS calc. for C$_{20}$H$_{20}$N$_3$O$_2$ (M+H)$^+$: m/z=334.2; found 334.1.

Step 2. N-{4-[(3R,4R,5S)-3-Amino-4-hydroxy-5-methylpiperidin-1-yl]pyridin-3-yl}-7-(4-pyridin-4-ylpiperidin-1-yl)quinoline-2-carboxamide To a mixture of 7-(4-pyridin-4-ylpiperidin-1-yl)quinoline-2-carboxylic acid [1.0]-trifluoroacetic acid (103.6 mg, 0.2316 mmol), tert-butyl ((3R,4R,5S)-1-(3-aminopyridin-4-yl)-4-{[tert-butyl(dimethyl)silyl]oxy}-5-methylpiperidin-3-yl)carbamate (96.7 mg, 0.221 mmol) and HATU (269.6 mg, 0.7090 mmol) was added DMF (2.00 mL) followed by DIPEA (256.0 mg, 1.981 mmol).) After stirring at room temperature for 18 h, the reaction was diluted with EtOAc. The mixture was washed with water, and brine. The organic layer was dried over Na$_2$SO$_4$, filtered, and concentrated. To the resulting residue was added 4.0 M HCl in dioxane (4.00 mL, 16.0 mmol). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (49.4 mg, 42%). LCMS calc. for C$_{31}$H$_{36}$N$_7$O$_2$ (M+H)$^+$: m/z=538.3; found 538.3.

Example 21

N-{4-[(3S,5R)-3-Amino-5-methylpiperidin-1-yl]pyridin-3-yl}-7-(4-pyridin-4-ylpiperidin-1-yl)quinoline-2-carboxamide

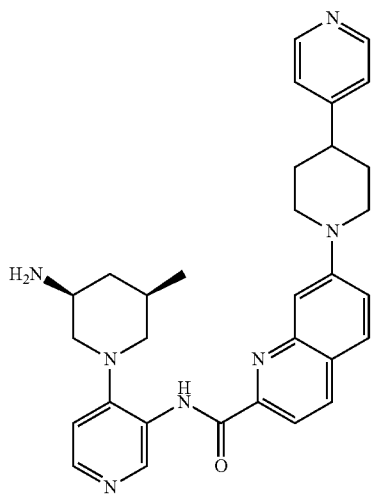 [SMILES: C[C@@H]1C[C@H](N)CN(c2ccncc2NC(=O)c2ccc3ccc(N4CCC(c5ccncc5)CC4)cc3n2)C1]

To a mixture of 7-(4-pyridin-4-ylpiperidin-1-yl)quinoline-2-carboxylic acid [1.0]-trifluoroacetic acid (83.1 mg, 0.186 mmol), tert-butyl [(3S,5R)-1-(3-aminopyridin-4-yl)-5-methylpiperidin-3-yl]carbamate (53.0 mg, 0.173 mmol) and HATU (221.0 mg, 0.5812 mmol) was added DMF (2.00 mL) followed by DIPEA (195.8 mg, 1.515 mmol). After stirring at room temperature for 18 h, the reaction was diluted with EtOAc. The mixture was washed with water, and brine. The organic layer was dried over Na$_2$SO$_4$, filtered, and concentrated. To the resulting residue was added DCM (2.00 mL) and TFA (2.00 mL). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (41.4 mg, 46%). LCMS calc. for C$_{31}$H$_{36}$N$_7$O (M+H)$^+$: m/z=522.3; found 522.3.

Example 22

N-{4-[(3R,4R,5S)-3-Amino-4-hydroxy-5-methylpiperidin-1-yl]pyridin-3-yl}-7-(4-ethyl-3-oxopiperazin-1-yl)quinoline-2-carboxamide

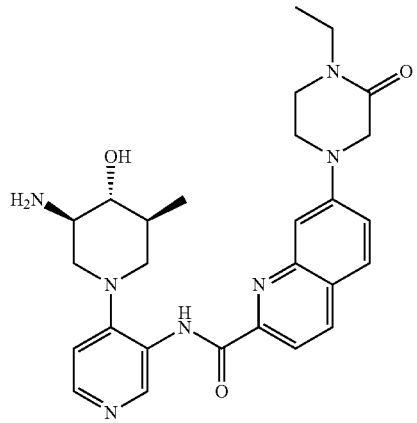 [SMILES: CCN1CCN(c2ccc3ccc(C(=O)Nc4cnccc4N4C[C@@H](N)[C@H](O)[C@@H](C)C4)nc3c2)CC1=O]

Step 1. 7-(4-Ethyl-3-oxopiperazin-1-yl)quinoline-2-carboxylic acid [1.0]-trifluoroacetic acid

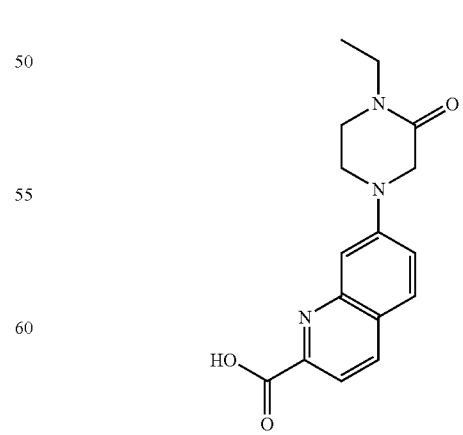

To a screw-cap vial equipped with a magnetic stir bar was added methyl 7-bromoquinoline-2-carboxylate (152.9 mg, 0.5746 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 56.1 mg, 0.0722 mmol), and Cs$_2$CO$_3$ (595.5 mg, 1.828 mmol). The vial was sealed with a PTFE-lined septum, evacuated and backfilled with N$_2$ (this process was repeated a total of three times). A solution of 1-ethylpiperazin-2-one (153.2 mg, 1.195 mmol) in anhydrous t-BuOH (4.00 mL) was added via syringe. The mixture was heated to 100° C. for 10 h. After cooling to room temperature, the reaction mixture was diluted with MeOH (20 mL). AcOH (1.00 mL, 17.6 mmol) was added. The mixture was filtered through a pad of diatomaceous earth (eluted with MeOH). The filtrate was concentrated under reduced pressure, and the residue was purified using RP-HPLC (XBridge™ C18 column, eluting with a gradient of MeCN/water containing 0.05% TFA, at flow rate of 30 mL/min.) to afford the title product as a red solid (117.3 mg, 49%). LCMS calc. for C$_{16}$H$_{18}$N$_3$O$_3$ (M+H)$^+$: m/z=300.1; found 300.1.

Step 2. N-{4-[(3R,4R,5S)-3-Amino-4-hydroxy-5-methylpiperidin-1-yl]pyridin-3-yl}-7-(4-ethyl-3-oxopiperazin-1-yl)quinoline-2-carboxamide To a mixture of 7-(4-ethyl-3-oxopiperazin-1-yl)quinoline-2-carboxylic acid [1.0]-trifluoroacetic acid (56.6 mg, 0.137 mmol), tert-butyl ((3R,4R,5S)-1-(3-aminopyridin-4-yl)-4-{[tert-butyl(dimethyl)silyl]oxy}-5-methylpiperidin-3-yl)carbamate (57.7 mg, 0.132 mmol) and HATU (166.8 mg, 0.4387 mmol) was added DMF (2.00 mL) followed by DIPEA (160.1 mg, 1.239 mmol). After stirring at room temperature for 18 h, the reaction was diluted with EtOAc. The mixture was washed with water, and brine. The organic layer was dried over Na$_2$SO$_4$, filtered, and concentrated. To the resulting residue was added 0.4.0 M HCl in dioxane (4.00 mL, 16.0 mmol). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (40.5 mg, 61%). LCMS calc. for C$_{27}$H$_{34}$N$_7$O$_3$ (M+H)$^+$: m/z=504.3; found 504.3.

Example 23

N-{4-[(3S,5R)-3-Amino-5-methylpiperidin-1-yl]pyridin-3-yl}-7-(4-ethyl-3-oxopiperazin-1-yl)quinoline-2-carboxamide To a mixture of 7-(4-ethyl-3-oxopiperazin-1-yl)quinoline-2-carboxylic acid [1.0]-trifluoroacetic acid (60.8 mg, 0.147 mmol), tert-butyl [(3S,5R)-1-(3-aminopyridin-4-yl)-5-methylpiperidin-3-yl]carbamate (44.1 mg, 0.144 mmol) and HATU (176.7 mg, 0.4647 mmol) was added DMF (2.00 mL) followed by DIPEA (163.2 mg, 1.263 mmol). After stirring at room temperature for 18 h, the reaction was diluted with EtOAc. The mixture was washed with water, and brine. The organic layer was dried over Na$_2$SO$_4$, filtered, and concentrated. To the resulting residue was added DCM (2.00 mL) and TFA (2.00 mL). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (43.4 mg, 62%). LCMS calc. for C$_{27}$H$_{34}$N$_7$O$_2$ (M+H)$^+$: m/z=488.3; found 488.3.

Example 24

N-{4-[(3R,4R,5S)-3-Amino-4-hydroxy-5-methylpiperidin-1-yl]pyridin-3-yl}-7-(4-methoxypiperidin-1-yl)quinoline-2-carboxamide

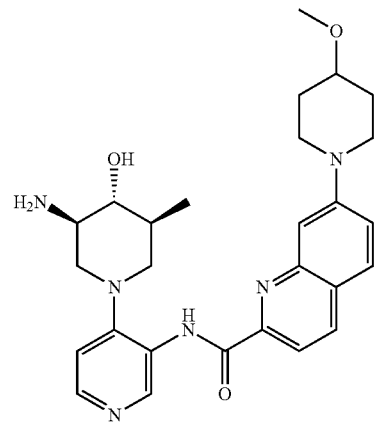

Step 1.
7-(4-Methoxypiperidin-1-yl)quinoline-2-carboxylic acid [1.0]-trifluoroacetic acid

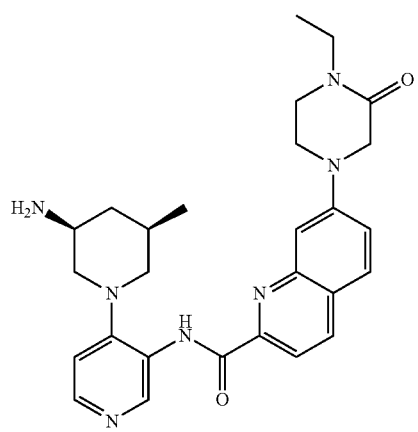 [SMILES: CCN1CCN(c2ccc3ccc(C(=O)Nc4cnccc4N4C[C@H](C)C[C@H](N)C4)nc3c2)CC1=O]

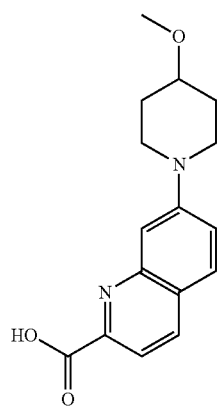 [SMILES: COC1CCN(c2ccc3ccc(C(=O)O)nc3c2)CC1]

To a screw-cap vial equipped with a magnetic stir bar was added methyl 7-bromoquinoline-2-carboxylate (151.9 mg, 0.5708 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 57.4 mg, 0.0739 mmol), and Cs$_2$CO$_3$ (598.9 mg, 1.838 mmol). The vial was sealed with a PTFE-lined septum, evacuated and backfilled with N$_2$ (this process was repeated a total of three times). A solution of 4-methoxypiperidine (148.4 mg, 1.288 mmol) in anhydrous t-BuOH (4.00 mL) was added via syringe. The mixture was heated to 100° C. for 10 h. After cooling to room temperature, the reaction mixture was diluted with MeOH (20 mL). AcOH (1.00 mL, 17.6 mmol) was added. The mixture was filtered through a pad of diatomaceous earth (eluted with MeOH). The filtrate was concentrated under reduced pressure, and the residue was purified using RP-HPLC (XBridge™ C18 column, eluting with a gradient of MeCN/water containing 0.05% TFA, at flow rate of 30 mL/min.) to afford the title product as a red solid (77.4 mg, 34%). LCMS calc. for C$_{16}$H$_{19}$N$_2$O$_3$ (M+H)$^+$: m/z=287.1; found 287.1.

Step 2. N-{4-[(3R,4R,5S)-3-Amino-4-hydroxy-5-methylpiperidin-1-yl]pyridin-3-yl}-7-(4-methoxypiperidin-1-yl)quinoline-2-carboxamide To a mixture of 7-(4-methoxypiperidin-1-yl)quinoline-2-carboxylic acid [1.0]-trifluoroacetic acid (37.8 mg, 0.0944 mmol), tert-butyl ((3R,4R,5S)-1-(3-aminopyridin-4-yl)-4-{[tert-butyl(dimethyl)silyl]oxy}-5-methylpiperidin-3-yl)carbamate (42.4 mg, 0.0971 mmol) and HATU (120.3 mg, 0.3164 mmol) was added DMF (2.00 mL) followed by DIPEA (117.9 mg, 0.9122 mmol). After stirring at room temperature for 18 h, the reaction was diluted with EtOAc. The mixture was washed with water, and brine. The organic layer was dried over Na$_2$SO$_4$, filtered, and concentrated. To the resulting residue was added 4.0 M HCl in dioxane (4.00 mL, 16.0 mmol). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (26.7 mg, 58%). LCMS calc. for C$_{27}$H$_{35}$N$_6$O$_3$ (M+H)$^+$: m/z=491.3; found 491.3.

Example 25

N-{4-[(3S,5R)-3-Amino-5-methylpiperidin-1-yl]pyridin-3-yl}-7-(4-methoxypiperidin-1-yl)quinoline-2-carboxamide

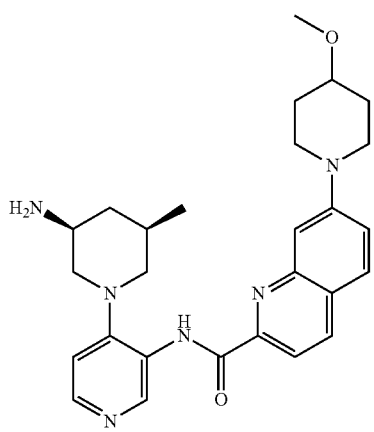 [SMILES: COC1CCN(c2ccc3ccc(C(=O)Nc4cnccc4N4C[C@H](C)C[C@H](N)C4)nc3c2)CC1]

To a mixture of 7-(4-methoxypiperidin-1-yl)quinoline-2-carboxylic acid [1.0]-trifluoroacetic acid (41.2 mg, 0.103 mmol), tert-butyl [(3S,5R)-1-(3-aminopyridin-4-yl)-5-methylpiperidin-3-yl]carbamate (32.5 mg, 0.106 mmol) and HATU (132.2 mg, 0.3477 mmol) was added DMF (2.00 mL) followed by DIPEA (140.2 mg, 1.085 mmol). After stirring at room temperature for 18 h, the reaction was diluted with EtOAc. The mixture was washed with water, and brine. The organic layer was dried over Na$_2$SO$_4$, filtered, and concentrated. To the resulting residue was added DCM (2.00 mL) and TFA (2.00 mL). The reaction mixture was stirred at room temperature for 2 h, and then concentrated. The residue was purified using RP-HPLC (XBridge™ C18 column, eluting with a gradient of MeCN/water containing 0.1% NH$_4$OH, at flow rate of 30 mL/min.) to afford the title product as a yellow solid (26.2 mg, 54%). LCMS calc. for C$_{27}$H$_{35}$N$_6$O$_2$ (M+H)$^+$: m/z=475.3; found 475.2.

Example 26

N-{4-[(3R,4R,5S)-3-Amino-4-hydroxy-5-methylpiperidin-1-yl]pyridin-3-yl}-7-(4-morpholin-4-ylpiperidin-1-yl)quinoline-2-carboxamide

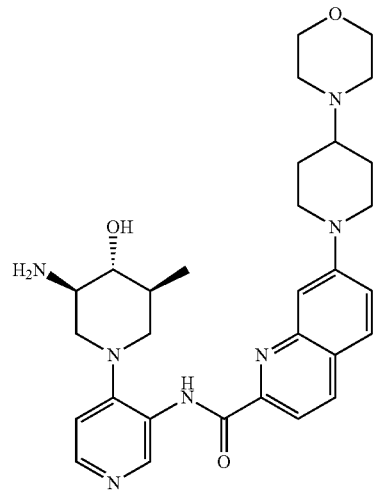 [SMILES: C[C@H]1CN(c2ccncc2NC(=O)c2ccc3ccc(N4CCC(N5CCOCC5)CC4)cc3n2)C[C@@H](N)[C@@H]1O]

Step 1. 7-(4-Morpholin-4-ylpiperidin-1-yl)quinoline-2-carboxylic acid [1.0]-trifluoroacetic acid

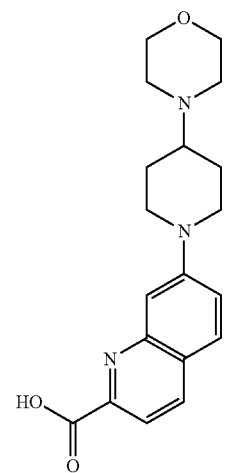 [SMILES: O=C(O)c1ccc2ccc(N3CCC(N4CCOCC4)CC3)cc2n1]

To a screw-cap vial equipped with a magnetic stir bar was added methyl 7-bromoquinoline-2-carboxylate (154.9 mg, 0.5821 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 57.1 mg, 0.0735 mmol), and $Cs_2CO_3$ (623.3 mg, 1.913 mmol). The vial was sealed with a PTFE-lined septum, evacuated and backfilled with $N_2$ (this process was repeated a total of three times). A solution of 4-piperidin-4-ylmorpholine (215.7 mg, 1.267 mmol) in anhydrous t-BuOH (4.00 mL) was added via syringe. The mixture was heated to 100° C. for 10 h. After cooling to room temperature, the reaction mixture was diluted with MeOH (20 mL). AcOH (1.00 mL, 17.6 mmol) was added. The mixture was filtered through a pad of diatomaceous earth (eluted with MeOH). The filtrate was concentrated under reduced pressure, and the residue was purified using RP-HPLC (XBridge™ C18 column, eluting with a gradient of MeCN/water containing 0.05% TFA, at flow rate of 30 mL/min.) to afford the title product as a red solid (147.0 mg, 55%). LCMS calc. for $C_{19}H_{24}N_3O_3$ $(M+H)^+$: m/z=342.2; found 342.2.

Step 2. N-{4-[(3R,4R,5S)-3-Amino-4-hydroxy-5-methylpiperidin-1-yl]pyridin-3-yl}-7-(4-morpholin-4-ylpiperidin-1-yl)quinoline-2-carboxamide To a mixture of 7-(4-morpholin-4-ylpiperidin-1-yl)quinoline-2-carboxylic acid [1.0]-trifluoroacetic acid (74.9 mg, 0.164 mmol), tert-butyl ((3R,4R,5S)-1-(3-aminopyridin-4-yl)-4-{[tert-butyl(dimethyl)silyl]oxy}-5-methylpiperidin-3-yl)carbamate (73.3 mg, 0.168 mmol) and HATU (206.9 mg, 0.5441 mmol) was added DMF (2.00 mL) followed by DIPEA (230.7 mg, 1.785 mmol). After stirring at room temperature for 18 h, the reaction was diluted with EtOAc. The mixture was washed with water, and brine. The organic layer was dried over $Na_2SO_4$, filtered, and concentrated. To the resulting residue was added 4.0 M HCl in dioxane (4.00 mL, 16.0 mmol). The reaction mixture was stirred at room temperature for 2 h, and then concentrated. The residue was purified using RP-HPLC (XBridge™ C18 column, eluting with a gradient of MeCN/water containing 0.1% $NH_4OH$, at flow rate of 30 mL/min.) to afford the title product as a yellow solid (35.6 mg, 40%). LCMS calc. for $C_{30}H_{40}N_7O_3$ $(M+H)^+$: m/z=546.3; found 546.3.

Example 27

N-{4-[(3S,5R)-3-Amino-5-methylpiperidin-1-yl]pyridin-3-yl}-7-(4-morpholin-4-ylpiperidin-1-yl)quinoline-2-carboxamide

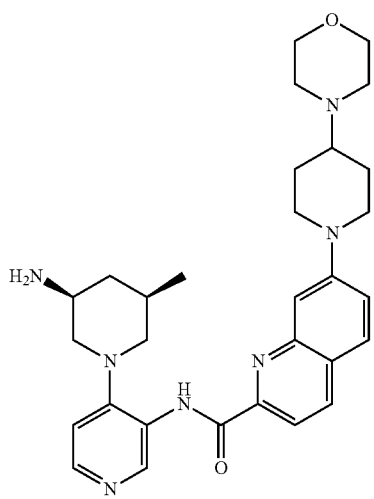 [SMILES: C[C@@H]1C[C@H](N)CN(c2ccncc2NC(=O)c2ccc3ccc(N4CCC(N5CCOCC5)CC4)cc3n2)C1]

To a mixture of 7-(4-morpholin-4-ylpiperidin-1-yl)quinoline-2-carboxylic acid [1.0]-trifluoroacetic acid (73.9 mg, 0.162 mmol), tert-butyl [(3S,5R)-1-(3-aminopyridin-4-yl)-5-methylpiperidin-3-yl]carbamate (49.8 mg, 0.162 mmol) and HATU (197.2 mg, 0.5186 mmol) was added DMF (2.00 mL) followed by DIPEA (226.0 mg, 1.749 mmol). After stirring at room temperature for 18 h, the reaction was diluted with EtOAc. The mixture was washed with water, and brine. The organic layer was dried over $Na_2SO_4$, filtered, and concentrated. To the resulting residue was added DCM (2.00 mL) and TFA (2.00 mL). The reaction mixture was stirred at room temperature for 2 h, and then concentrated. The residue was purified using RP-HPLC (XBridge™ C18 column, eluting with a gradient of MeCN/water containing 0.1% $NH_4OH$, at flow rate of 30 mL/min.) to afford the title product as a yellow solid (34.3 mg, 40%). LCMS calc. for $C_{30}H_{40}N_7O_2$ $(M+H)^+$: m/z=530.3; found 530.3.

Example 28

N-{4-[(3R,4R,5S)-3-Amino-4-hydroxy-5-methylpiperidin-1-yl]pyridin-3-yl}-7-[3-(trifluoromethyl)pyrrolidin-1-yl]quinoline-2-carboxamide

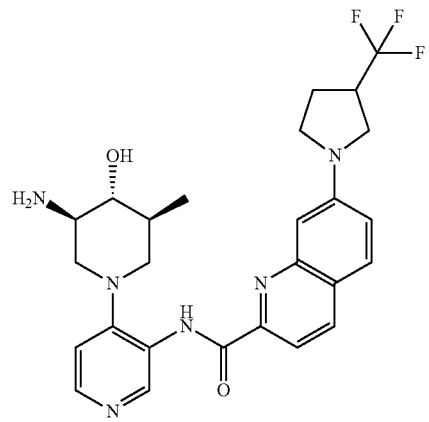 [SMILES: C[C@H]1CN(c2ccncc2NC(=O)c2ccc3ccc(N4CCC(C(F)(F)F)C4)cc3n2)C[C@@H](N)[C@@H]1O]

Step 1: 7-[3-(Trifluoromethyl)pyrrolidin-1-yl]quinoline-2-carboxylic acid

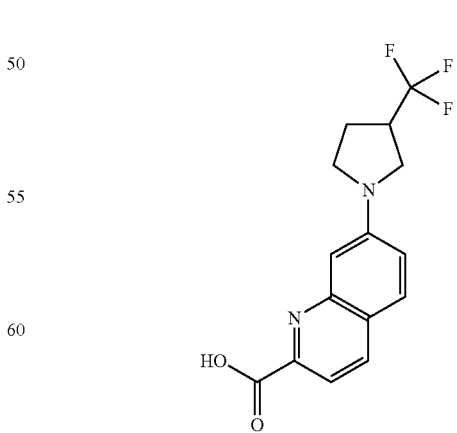

A mixture of methyl 7-bromoquinoline-2-carboxylate (40.0 mg, 0.15 mmol), dicyclohexyl(2',6'-diisopropoxybiphenyl-2-yl)phosphine-(2'-aminobiphenyl-2-yl)(chloro)palladium (1:1) (23.4 mg, 0.03 mmol) and Cs$_2$CO$_3$ (0.17 g, 0.53 mmol) in a sealed tube was evacuated and backfilled with N$_2$. A solution of 3-(trifluoromethyl)pyrrolidine HCl (47.5 mg, 0.27 mmol) in anhydrous t-BuOH (0.62 mL) was then added. The resulting reaction mixture was heated to 100° C. and stirred for 16 h. The reaction mixture was cooled to room temperature, neutralized with 4M HCl and diluted with EtOAc. The aqueous layer was extracted with EtOAc (2×) to remove impurities. The solvents and water were removed under reduced pressure. The residue was diluted with THF, dried, filtered and concentrated under reduced pressure to give the yellow solid (70 mg, 95%). LCMS calc. for C$_{15}$H$_{14}$F$_3$N$_2$O$_2$ (M+H)$^+$: m/z=311.3. Found: 311.3.

Step 2: tert-Butyl ((3R,4R,5S)-4-{[tert-butyl(dimethyl)silyl]oxy}-5-methyl-1-{3-[({7-[3-(trifluoromethyl)pyrrolidin-1-yl]quinolin-2-yl}carbonyl)amino]pyridin-4-yl}piperidin-3-yl)carbamate

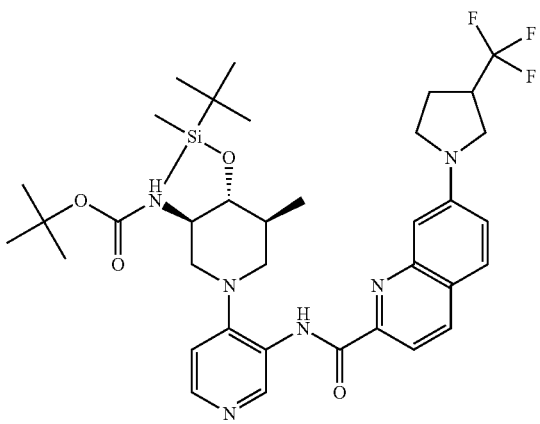

To a mixture of 7-[3-(trifluoromethyl)pyrrolidin-1-yl]quinoline-2-carboxylic acid (10.0 mg, 0.032 mmol), tert-butyl ((3R,4R,5S)-1-(3-aminopyridin-4-yl)-4-{[tert-butyl(dimethyl)silyl]oxy}-5-methylpiperidin-3-yl)carbamate (16.9 mg, 0.039 mmol) and HATU (36.8 mg, 0.097 mmol) was added DMF (0.20 mL), followed by DIPEA (16.8 μL, 0.097 mmol). The reaction mixture was stirred at room temperature for 20 h. The cloudy mixture was diluted with THF, filtered, and concentrated to give the crude intermediate, which was purified by preparative LCMS (pH=10 method; XBridge™ PrepC18 5 m OBD™ column, 30×10 mm, 60 mL/min., eluting with a gradient of MeCN and water with NH$_4$OH) to give the sub-title product as light yellow powder (4 mg, 17%). LCMS calc. for C$_{37}$H$_{52}$F$_3$N$_6$O$_4$Si (M+H)$^+$: m/z=729.3. Found: 729.3.

Step 3: N-{4-[(3R,4R,5S)-3-Amino-4-hydroxy-5-methylpiperidin-1-yl]pyridin-3-yl}-7-[3-(trifluoromethyl)pyrrolidin-1-yl]quinoline-2-carboxamide A solution of tert-butyl ((3R,4R,5S)-4-{[tert-butyl(dimethyl)silyl]oxy}-5-methyl-1-{3-[({7-[3-(trifluoromethyl)pyrrolidin-1-yl]quinolin-2-yl}carbonyl)amino]pyridin-4-yl}piperidin-3-yl)carbamate in 4.0 M HCl in dioxane (0.48 mL, 1.9 mmol) was stirred at room temperature for 60 min. The reaction mixture was concentrated under reduced pressure. The residue was purified on preparative LCMS (pH=10 method; XBridge™ preparative C18 5 m OBD™ column, 30×10 mm, 60 mL/min., eluting with a gradient of MeCN and water with NH$_4$OH) to give the sub-title product as yellow powder (1.0 mg, 6%). LCMS calc. for C$_{26}$H$_{30}$F$_3$N$_6$O$_2$ (M+H)$^+$: m/z=515.2. Found: 515.3.

Example 29

N-{4-[(3S,5R)-3-Amino-5-methylpiperidin-1-yl]pyridin-3-yl}-7-[3-(trifluoromethyl)pyrrolidin-1-yl]quinoline-2-carboxamide

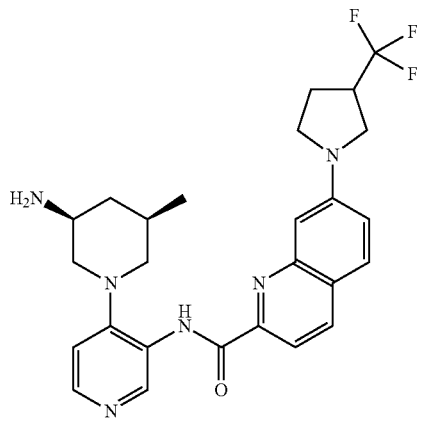 [SMILES: C[C@@H]1C[C@H](N)CN(c2ccncc2NC(=O)c2ccc3ccc(N4CCC(C(F)(F)F)C4)cc3n2)C1]

The title compound was prepared according to the procedure Example 28, using the following two starting materials, 7-[3-(trifluoromethyl)pyrrolidin-1-yl]quinoline-2-carboxylic acid (10.0 mg, 0.032 mmol) (prepared in Example 27, step 1) and tert-butyl [(3S,5R)-1-(3-aminopyridin-4-yl)-5-methylpiperidin-3-yl]carbamate (11.8 mg, 0.039 mmol), to afford the title product as a light yellow powder in 8% yield (3 steps). LCMS calc. for C$_{26}$H$_{30}$F$_3$N$_6$O (M+H)$^+$: m/z=499.2. Found: 499.3.

Example 30

N-{4-[(3R,4R,5S)-3-Amino-4-hydroxy-5-methylpiperidin-1-yl]pyridin-3-yl}-7-pyrrolidin-1-ylquinoline-2-carboxamide

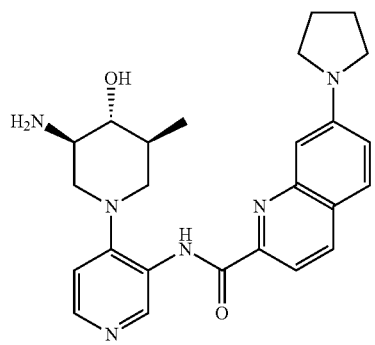 [SMILES: C[C@H]1CN(c2ccncc2NC(=O)c2ccc3ccc(N4CCCC4)cc3n2)C[C@@H](N)[C@@H]1O]

Step 1: 7-Pyrrolidin-1-ylquinoline-2-carboxylic acid

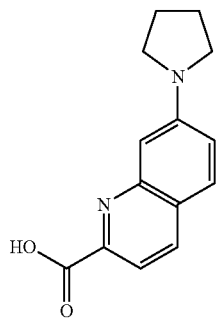 [SMILES: O=C(O)c1ccc2ccc(N3CCCC3)cc2n1]

A mixture of methyl 7-bromoquinoline-2-carboxylate (40.0 mg, 0.15 mmol), dicyclohexyl(2',6'-diisopropoxybiphenyl-2-yl)phosphine-(2'-aminobiphenyl-2-yl)(chloro)palladium (1:1) (23.4 mg, 0.03 mmol) and $Cs_2CO_3$ (0.17 g, 0.53 mmol) in a sealed tube was evacuated and backfilled with $N_2$. A solution of pyrrolidine (19.2 mg, 0.27 mmol) in anhydrous t-BuOH (0.62 mL) was then added. The reaction mixture was heated to 100° C. and stirred for 16 h. The reaction mixture was cooled to room temperature, neutralized with 4 M HCl and diluted with EtOAc. The aqueous layer was extracted with EtOAc (2×) to remove impurities. The solvents and water were removed under reduced pressure. The residue was diluted with THF, dried, filtered, and concentrated under reduced pressure to give the sub-title compound as a yellow solid (31 mg, 86%). LCMS calc. for $C_{14}H_{15}N_2O_2$ $(M+H)^+$: m/z=243.1. Found: 243.2.

Step 2: N-{4-[(3R,4R,5S)-3-Amino-4-hydroxy-5-methylpiperidin-1-yl]pyridin-3-yl}-7-pyrrolidin-1-ylquinoline-2-carboxamide The title compound was prepared according to the procedure Example 28, using the following two starting materials, 7-pyrrolidin-1-ylquinoline-2-carboxylic acid (10.0 mg, 0.04 mmol) and tert-butyl ((3R,4R,5S)-1-(3-aminopyridin-4-yl)-4-{[tert-butyl(dimethyl)silyl]oxy}-5-methylpiperidin-3-yl)carbamate (21.6 mg, 0.050 mmol), to give the title product as yellow powder (3.7 mg, 21%). LCMS calc. for $C_{25}H_{31}N_6O_2$ $(M+H)^+$: m/z=447.2. Found: 447.3.

Example 31

N-{4-[(3S,5R)-3-Amino-5-methylpiperidin-1-yl]pyridin-3-yl}-7-pyrrolidin-1-ylquinoline-2-carboxamide

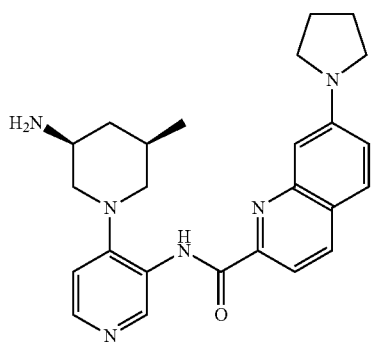 [SMILES: C[C@@H]1C[C@H](N)CN(c2ccncc2NC(=O)c2ccc3ccc(N4CCCC4)cc3n2)C1]

The title compound was prepared according to the procedure Example 28, using the following two starting materials, 7-pyrrolidin-1-ylquinoline-2-carboxylic acid (10.0 mg, 0.041 mmol) and tert-butyl [(3S,5R)-1-(3-aminopyridin-4-yl)-5-methylpiperidin-3-yl]carbamate (15.2 mg, 0.050 mmol), to afford the title product as light yellow powder in 13% yield (3 steps). LCMS calc. for $C_{25}H_{31}N_6O$ $(M+H)^+$: m/z=431.3. Found: 431.2.

Example 32

N-{4-[(3R,4R,5S)-3-Amino-4-hydroxy-5-methylpiperidin-1-yl]pyridin-3-yl}-7-(3,3-dimethylazetidin-1-yl)quinoline-2-carboxamide

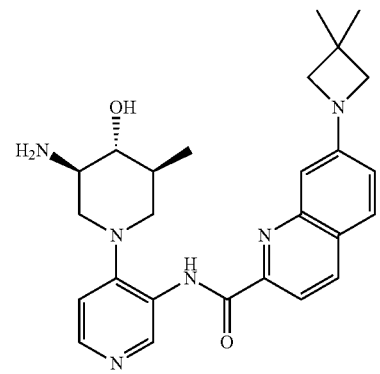 [SMILES: C[C@H]1CN(c2ccncc2NC(=O)c2ccc3ccc(N4CC(C)(C)C4)cc3n2)C[C@@H](N)[C@@H]1O]

Step 1: 7-(3,3-Dimethylazetidin-1-yl)quinoline-2-carboxylic acid

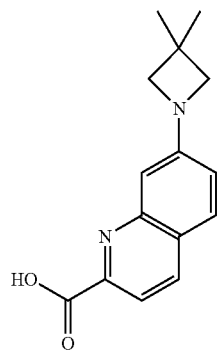 [SMILES: CC1(C)CN(c2ccc3ccc(C(=O)O)nc3c2)C1]

A mixture of methyl 7-bromoquinoline-2-carboxylate (40.0 mg, 0.15 mmol), dicyclohexyl(2',6'-diisopropoxybiphenyl-2-yl)phosphine-(2'-aminobiphenyl-2-yl)(chloro)palladium (1:1) (23.4 mg, 0.03 mmol) and $Cs_2CO_3$ (0.17 g, 0.53 mmol) in a sealed tube was evacuated and backfilled with $N_2$. A solution of 3,3-dimethylazetidine HCl (32.9 mg, 0.27 mmol) in anhydrous t-BuOH (0.62 mL) was added. The resulting reaction mixture was heated to 100° C. and stirred for 16 h. The reaction mixture was cooled to room temperature, neutralized with 4M HCl and diluted with EtOAc. The aqueous layer was extracted with EtOAc (2×) to remove impurities. The solvents and water were removed under reduced pressure. The crude was purified by preparative LCMS (pH=2 method; Waters SunFire™ preparative C18 5 μm OBD™ column, 30×100 mm, 60 mL/min., eluting with a gradient of MeCN and water with TFA) to give the sub-title compound as a yellow powder (24.7 mg, 64%). LCMS calc. for $C_{15}H_{17}N_2O_2$ $(M+H)^+$: m/z=257.1. Found: 257.3.

Step 2: N-{4-[(3R,4R,5S)-3-Amino-4-hydroxy-5-methylpiperidin-1-yl]pyridin-3-yl}-7-(3,3-dimethyl-azetidin-1-yl)quinoline-2-carboxamide The title compound was prepared according to the procedure Example 27, using the following two starting materials, 7-(3,3-dimethylazetidin-1-yl)quinoline-2-carboxylic acid (8.0 mg, 0.03 mmol) and tert-butyl ((3R,4R,5S)-1-(3-aminopyridin-4-yl)-4-{[tert-butyl(dimethyl)silyl]oxy}-5-methylpiperidin-3-yl)carbamate (16.4 mg, 0.04 mmol), to afford the title product as light yellow powder (2.2 mg, 15%) in two steps. LCMS calc. for $C_{26}H_{33}N_6O_2$ (M+H)$^+$: m/z=461.3. Found: 461.3.

Example 33

N-{4-[(3S,5R)-3-Amino-5-methylpiperidin-1-yl]pyridin-3-yl}-7-(3,3-dimethylazetidin-1-yl)quinoline-2-carboxamide

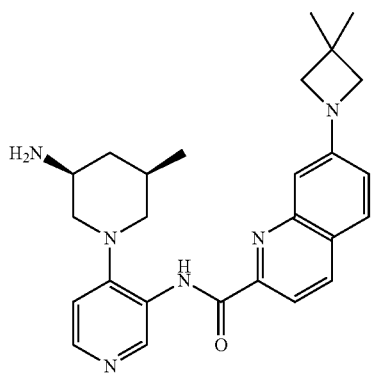 [SMILES: C[C@@H]1C[C@H](N)CN(c2ccncc2NC(=O)c2ccc3ccc(N4CC(C)(C)C4)cc3n2)C1]

The title compound was prepared according to the procedure Example 28, using the following two starting materials, 7-(3,3-dimethylazetidin-1-yl)quinoline-2-carboxylic acid (8.0 mg, 0.03 mmol) and tert-butyl [(3S,5R)-1-(3-aminopyridin-4-yl)-5-methylpiperidin-3-yl]carbamate (11.5 mg, 0.037 mmol), to afford the title product as light yellow powder in 17% yield (3 steps). LCMS calc. for $C_{26}H_{33}N_6O$ (M+H)$^+$: m/z=445.3. Found: 445.3.

Example 34

N-{4-[(3S,5R)-3-Amino-5-methylpiperidin-1-yl]pyridin-3-yl}-7-azetidin-1-ylquinoline-2-carboxamide

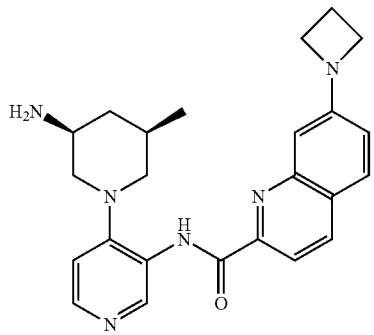 [SMILES: C[C@@H]1C[C@H](N)CN(c2ccncc2NC(=O)c2ccc3ccc(N4CCC4)cc3n2)C1]

Step 1: 7-Azetidin-1-ylquinoline-2-carboxylic acid

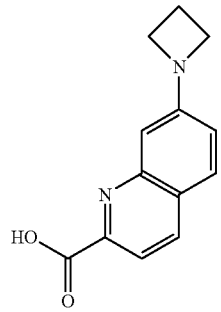 [SMILES: O=C(O)c1ccc2ccc(N3CCC3)cc2n1]

A mixture of methyl 7-bromoquinoline-2-carboxylate (40.0 mg, 0.15 mmol), dicyclohexyl(2',6'-diisopropoxybiphenyl-2-yl)phosphine-(2'-aminobiphenyl-2-yl)(chloro)palladium (1:1) (23.4 mg, 0.030 mmol) and $Cs_2CO_3$ (0.17 g, 0.53 mmol) in a sealed tube was evacuated and backfilled with $N_2$. A solution of azetidine hydrochloride (25.3 mg, 0.27 mmol) in anhydrous t-BuOH (0.62 mL) was added. The resulting reaction mixture was heated to 100° C. and stirred for 16 h. The reaction mixture was cooled to room temperature, neutralized with 4M HCl and diluted with EtOAc. The aqueous layer was extracted with EtOAc (2×) to remove impurities. The solvents and water were removed under reduced pressure. The residue was diluted with THF, dried, filtered and concentrated to give the sub-title compound as a yellow solid (30 mg, 91%). LCMS calc. for $C_{13}H_{13}N_2O_2$ (M+H)$^+$: m/z=229.1. Found: 229.2.

Step 2: N-{4-[(3S,5R)-3-Amino-5-methylpiperidin-1-yl]pyridin-3-yl}-7-azetidin-1-ylquinoline-2-carboxamide The title compound was prepared according to the procedure Example 28, using the following two starting materials, 7-azetidin-1-ylquinoline-2-carboxylic acid (5.0 mg, 0.02 mmol) and tert-butyl [(3S,5R)-1-(3-aminopyridin-4-yl)-5-methylpiperidin-3-yl]carbamate (8.1 mg, 0.026 mmol) to give the title product as a yellow powder (2 mg, 22%). LCMS calc. for $C_{24}H_{29}N_6O$ (M+H)$^+$: m/z=417.2. Found: 417.3.

Example 35

N-{4-[(3R,4R,5S)-3-Amino-5-cyclopropyl-4-hydroxypiperidin-1-yl]pyridin-3-yl}-7-(2,6-difluoro-4-methoxyphenyl)-1,5-naphthyridine-2-carboxamide

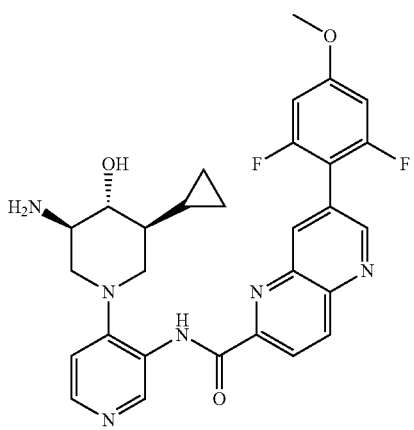 [SMILES: COc1cc(F)c(-c2cnc3ccc(C(=O)Nc4cnccc4N4C[C@@H](N)[C@H](O)[C@@H](C5CC5)C4)nc3c2)c(F)c1]

Step 1: tert-Butyl {(3R,4R,5S)-4-{[tert-butyl(dimethyl)silyl]oxy}-5-cyclopropyl-1-[3-({[7-(2, 6-difluoro-4-methoxyphenyl)-1,5-naphthyridin-2-yl]carbonyl}amino)pyridin-4-yl]piperidin-3-yl}carbamate

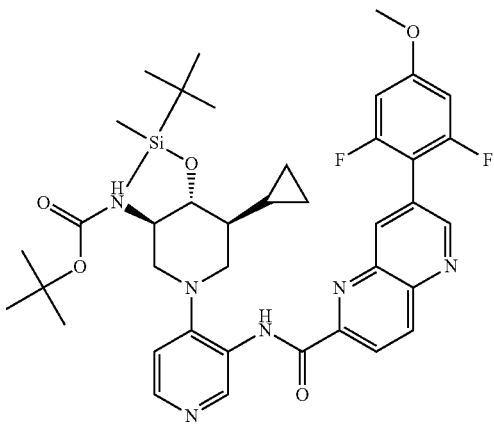

A mixture of 2-(2,6-difluoro-4-methoxyphenyl)-4,4,5,5-tetramethyl-1,3,2-dioxaborolane (0.036 g, 0.13 mmol), tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl)carbamate (0.068 g, 0.10 mmol), DIPEA (23 mg, 0.18 mmol), 1,4-dioxane (0.34 mL) and water (0.007 mL) was flushed with $N_2$ and then bis(tri-t-butylphosphine)palladium (0.01 g, 0.02 mmol) was added. The reaction mixture was sealed and heated at 120° C. for 2 h. After cooling, the reaction mixture was concentrated under reduced pressure and the crude was purified by preparative LC MS (pH=10 method; XBridge™ preparative C18 5 m OBD™ column, 30×10 mm, 60 mL/min., eluting with a gradient of MeCN and water with $NH_4OH$) to give the sub-title product as an off-white powder (62 mg, 84%). LCMS calc. for $C_{40}H_{51}F_2N_6O_5Si$ $(M+H)^+$: m/z=761.4. Found: 761.3.

Step 2: N-{4-[(3R,4R,5S)-3-Amino-5-cyclopropyl-4-hydroxypiperidin-1-yl]pyridin-3-yl}-7-(2,6-difluoro-4-methoxyphenyl)-1,5-naphthyridine-2-carboxamide To a solution of tert-butyl {(3R,4R,5S)-4-{[tert-butyl(dimethyl)silyl]oxy}-5-cyclopropyl-1-[3-({[7-(2,6-difluoro-4-methoxyphenyl)-1,5-naphthyridin-2-yl]carbonyl}amino)pyridin-4-yl]piperidin-3-yl}carbamate (62 mg, 0.08 mmol) in MeOH (2 mL) was added 4.0 M HCl in dioxane (2.0 mL, 8.0 mmol). The reaction mixture was stirred at room temperature for 30 min. After concentration under reduced pressure, the residue was diluted with MeOH and $NH_4OH$, filtered and purified by preparative LCMS (pH=10 method; XBridge™ preparative C18 5 μm OBD™ column, 30×10 mm, 60 mL/min., eluting with a gradient of MeCN and water with $NH_4OH$) to give the title product as a white powder (38 mg, 71%). LCMS calc. for $C_{29}H_{29}F_2N_6O_3$ $(M+H)^+$: m/z=547.2. Found: 547.3. $^1H$ NMR (500 MHz, DMSO-$d_6$): δ 10.34 (s, 1H), 9.34 (s, 1H), 9.18 (d, J=1.5, 1H), 8.75 (m, 1H), 8.58 (m, 2H), 8.28 (d, J=5.3, 1H), 7.14 (d, J=5.4, 1H), 7.01 (d, J=10.1, 2H), 4.60 (d, J=6.0, 1H), 3.89 (s, 3H), 3.27 (m, 2H), 2.96 (m, 2H), 2.59 (t, J=10.8, 1H), 2.55-2.49 (m, 1H), 1.66 (s, 2H), 1.25 (m, 1H), 0.57 (m, 1H), 0.30 (m, 1H), 0.17 (m, 1H), 0.04 (m, 2H) ppm.

Example 36

N-{4-[(3R,4R,5S)-3-Amino-5-cyclopropyl-4-hydroxypiperidin-1-yl]pyridin-3-yl}-7-(6-methoxypyridin-3-yl)-1,5-naphthyridine-2-carboxamide

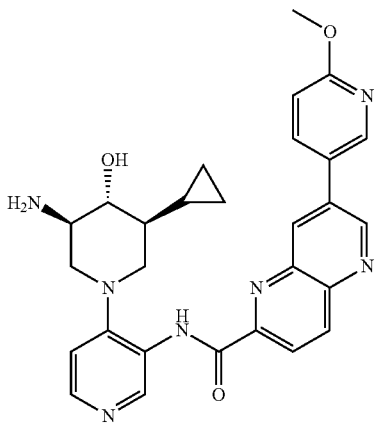 [SMILES: COc1ccc(-c2cnc3ccc(C(=O)Nc4cnccc4N4C[C@@H](N)[C@H](O)[C@@H](C5CC5)C4)nc3c2)cn1]

The title compound was prepared according to the procedure Example 35, using the following two starting materials, (6-methoxypyridin-3-yl)boronic acid (6.0 mg, 0.039 mmol) and tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl)carbamate (0.020 g, 0.029 mmol), to afford the title product as a white powder. LCMS calc. for $C_{28}H_{30}N_7O_3$ $(M+H)^+$: m/z=512.2. Found: 512.2.

Example 37

N-{4-[(3R,4R,5S)-3-Amino-5-cyclopropyl-4-hydroxypiperidin-1-yl]pyridin-3-yl}-7-(6-morpholin-4-ylpyridin-3-yl)-1,5-naphthyridine-2-carboxamide

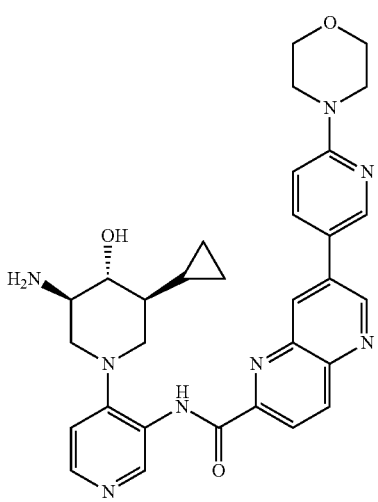 [SMILES: N[C@@H]1CN(c2ccncc2NC(=O)c2ccc3ncc(-c4ccc(N5CCOCC5)nc4)cc3n2)C[C@H](C2CC2)[C@H]1O]

The title compound was prepared according to the procedure Example 35, using the following two starting materials, 4-[5-(4,4,5,5-tetramethyl-1,3,2-dioxaborolan-2-yl)pyridin-2-yl]morpholine (110 mg, 0.039 mmol) and tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl)carbamate (20 mg, 0.029 mmol), to afford the title product as an off-white powder. LCMS calc. for $C_{31}H_{35}N_8O_3$ (M+H)$^+$: m/z=567.3. Found: 567.3.

Example 38

N-{4-[(3R,4R,5S)-3-Amino-5-cyclopropyl-4-hydroxypiperidin-1-yl]pyridin-3-yl}-7-(1-ethyl-1H-pyrazol-4-yl)-1,5-naphthyridine-2-carboxamide

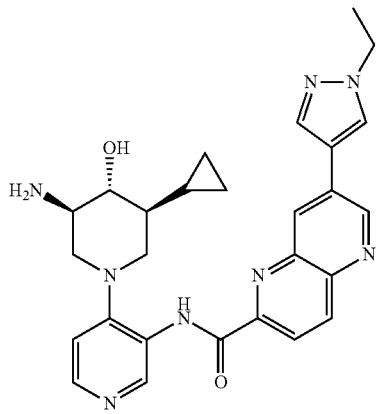 [SMILES: CCn1cc(-c2cnc3ccc(C(=O)Nc4cnccc4N4C[C@@H](N)[C@H](O)[C@@H](C5CC5)C4)nc3c2)cn1]

The title compound was prepared according to the procedure Example 35, using the following two starting materials, 1-ethyl-4-(4,4,5,5-tetramethyl-1,3,2-dioxaborolan-2-yl)-1H-pyrazole (8.7 mg, 0.039 mmol) and tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl)carbamate (20.0 mg, 0.029 mmol), to afford the title product as a white powder. LCMS calc. for $C_{27}H_{31}N_8O_2$ (M+H)$^+$: m/z=499.3. Found: 499.3.

Example 39

N-{4-[(3R,4R,5S)-3-Amino-5-cyclopropyl-4-hydroxypiperidin-1-yl]pyridin-3-yl}-7-(1-methyl-1H-pyrazol-4-yl)-1,5-naphthyridine-2-carboxamide

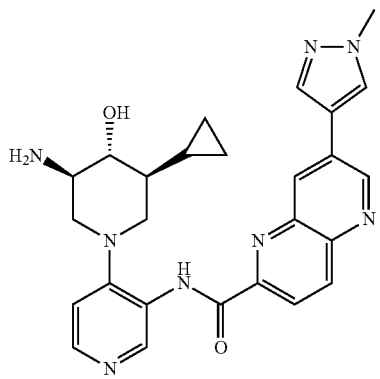 [SMILES: Cn1cc(-c2cnc3ccc(C(=O)Nc4cnccc4N4C[C@@H](N)[C@H](O)[C@@H](C5CC5)C4)nc3c2)cn1]

The title compound was prepared according to the procedure Example 35, using the following two starting materials, 1-methyl-4-(4,4,5,5-tetramethyl-1,3,2-dioxaborolan-2-yl)-1H-pyrazole (8.1 mg, 0.039 mmol), and tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl)carbamate (20.0 mg, 0.029 mmol), to afford the title product as a white powder. LCMS calc. for $C_{26}H_{29}N_8O_2$ (M+H)$^+$: m/z=485.3. Found: 485.3.

Example 40

N-{4-[(3R,4R,5S)-3-Amino-5-cyclopropyl-4-hydroxypiperidin-1-yl]pyridin-3-yl}-7-(3-oxa-9-azaspiro[5.5]undec-9-yl)-1,5-naphthyridine-2-carboxamide

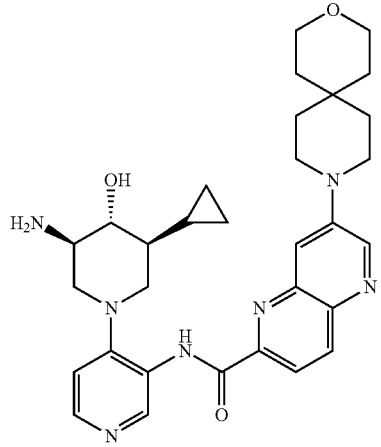 [SMILES: N[C@@H]1CN(c2ccncc2NC(=O)c2ccc3ncc(N4CCC5(CCOCC5)CC4)cc3n2)C[C@H](C2CC2)[C@H]1O]

The title compound was prepared according to the procedure Example 35, using the following two starting materials, tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl) carbamate (12 mg, 0.017 mmol) and 3-oxa-9-azaspiro[5.5] undecane (50 mg, 0.32 mmol), to afford the title product as a yellow powder. LCMS calc. for $C_{31}H_{40}N_7O_3$ (M+H)$^+$: m/z=558.3. Found: 558.4.

Example 41

N-{4-[(3R,4R,5S)-3-Amino-5-cyclopropyl-4-hydroxypiperidin-1-yl]pyridin-3-yl}-7-(4-cyanopiperidin-1-yl)-1,5-naphthyridine-2-carboxamide

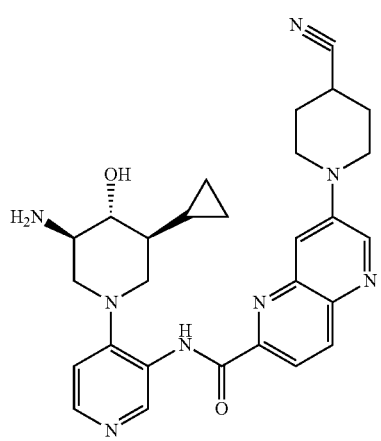 [SMILES: N#CC1CCN(c2cnc3ccc(C(=O)Nc4cnccc4N4C[C@@H](N)[C@H](O)[C@@H](C5CC5)C4)nc3c2)CC1]

The title compound was prepared according to the procedure Example 35, using the following two starting materials, tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl)carbamate (12 mg, 0.017 mmol) and piperidine-4-carbonitrile (12 mg, 0.11 mmol), to afford the title product as a yellow powder. LCMS calc. for $C_{28}H_{33}N_8O_2$ (M+H)$^+$: m/z=513.3. Found: 513.2.

Example 42

N-{4-[(3R,4R,5S)-3-Amino-5-cyclopropyl-4-hydroxypiperidin-1-yl]pyridin-3-yl}-7-(1-oxa-8-azaspiro[4.5]dec-8-yl)-1,5-naphthyridine-2-carboxamide

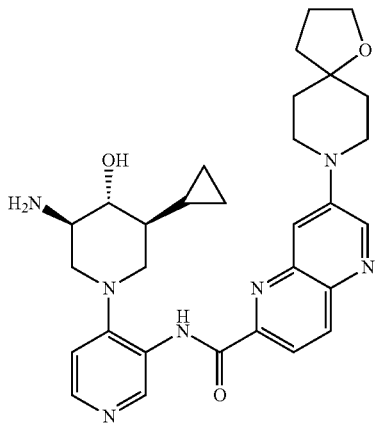 [SMILES: N[C@@H]1CN(c2ccncc2NC(=O)c2ccc3ncc(N4CCC5(CCCO5)CC4)cc3n2)C[C@H](C2CC2)[C@H]1O]

The title compound was prepared according to the procedure Example 35, using the following two starting materials, tert-butyl ((3R,4R,5S)-1-(3-{[(7-bromo-1,5-naphthyridin-2-yl)carbonyl]amino}pyridin-4-yl)-4-{[tert-butyl(dimethyl)silyl]oxy}-5-cyclopropylpiperidin-3-yl)carbamate (12 mg, 0.017 mmol) and 1-oxa-8-azaspiro[4.5]decane (46 mg, 0.32 mmol), to afford the title product as a yellow powder. LCMS calc. for $C_{30}H_{38}N_7O_3$ (M+H)$^+$: m/z=544.3. Found: 544.4.

Example 43

N-{4-[(3R,4R,5S)-3-Amino-4-hydroxy-5-methylpiperidin-1-yl]pyridin-3-yl}-7-(1-methyl-1H-pyrazol-4-yl)quinoline-2-carboxamide

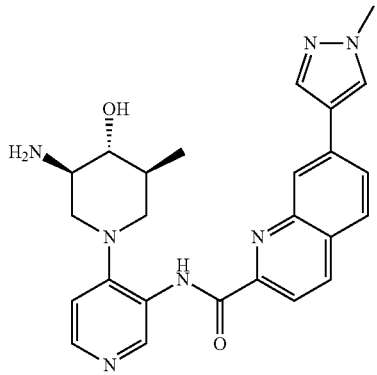 [SMILES: C[C@H]1CN(c2ccncc2NC(=O)c2ccc3ccc(-c4cnn(C)c4)cc3n2)C[C@@H](N)[C@@H]1O]

Step 1. tert-Butyl ((3R,4R,5S)-1-(3-{[(7-bromoquinolin-2-yl)carbonyl]amino}pyridin-4-yl)-4-{[tert-butyl(dimethyl)silyl]oxy}-5-methylpiperidin-3-yl)carbamate

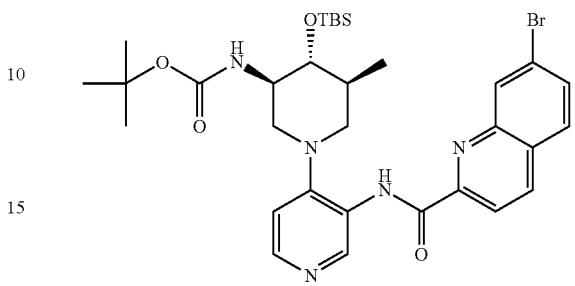

A mixture of tert-butyl ((3R,4R,5S)-1-(3-aminopyridin-4-yl)-4-{[tert-butyl(dimethyl)silyl]oxy}-5-methylpiperidin-3-yl)carbamate (1.7 g, 0.39 mmol), 7-bromoquinoline-2-carboxylic acid (1.0 g, 4.0 mmol) and N,N-diisopropylethylamine (1.4 mL, 8.0 mmol), and molecular sieves in 1,2-dichloroethane (60 mL) was stirred at room temperature for 0.5 h. Then HATU (0.031 g, 0.082 mmol) was added. The mixture was stirred at room temperature overnight, diluted with 50 mL EtOAc, filtered through a diatomaceous earth funnel, washed with saturated NaHCO$_3$, water, and brine. After separation of layers, the organic layers were dried over Na$_2$SO$_4$, and concentrated. The mixture was purified on 40 g silica gel column using CombiFlash® apparatus eluting with EtOAc/hexane (10-100%) to give product as brown solid (2.20 g, 85%), LCMS calc. for $C_{32}H_{45}BrN_5O_4Si$ (M+H)$^+$: m/z=670.2. Found: 670.2.

Step 2. N-{4-[(3R,4R,5S)-3-Amino-4-hydroxy-5-methylpiperidin-1-yl]pyridin-3-yl}-7-(1-methyl-1H-pyrazol-4-yl)quinoline-2-carboxamide In a microwave tube, a mixture of tert-butyl ((3R,4R,5S)-1-(3-{[(7-bromoquinolin-2-yl)carbonyl]amino}pyridin-4-yl)-4-{[tert-butyl(dimethyl)silyl]oxy}-5-methylpiperidin-3-yl)carbamate (100 mg, 15 mmol), (1-methyl-1H-pyrazol-4-yl)boronic acid (24 mg, 0.19 mmol), and DIPEA (0.078 mL, 0.45 mmol) in 1,4-dioxane (4.1 mL) and water (0.40 mL) was purged with N$_2$ bubbles for 5 min. before bis(tri-t-butylphosphine)palladium (20 mg, 0.04 mmol) was added. The reaction mixture was then heated at 110° C. for 1 h. The crude mixture was diluted with EtOAc and washed with saturated NaHCO$_3$ solution and brine. The organic layers were dried over Na$_2$SO$_4$ and concentrated. The residue was purified by silica gel column chromatography (40 g column, 20-100% EtOAc in hexanes) to give the coupling product.

The above coupling product was dissolved in small amount of MeOH and 4 N HCl was added. The mixture was stirred for 1 h at room temperature then concentrated. The residue was purified by preparative LCMS (pH=10 method; XBridge™ preparative C18 5 μm OBD™ column) to give the title product (20 mg, 29%). LCMS calc. for $C_{25}H_{28}N_7O_2$ (M+H)$^+$: m/z=458.2. Found: 458.1. $^1$H NMR (DMSO-d$_6$): δ 10.81 (s, 1H); 9.50 (s, 1H); 8.60 (d, 1H); 8.42 (s, 1H); 8.30 (d, 1H); 8.20 (d, 1H); 8.18 (s, 1H); 8.10 (d, 1H); 8.00 (d, 1H); 7.20 (s, 1H); 5.35 (s, 1H); 3.90 (s, 3H); 3.20-3.30 (m, 3H); 2.85 (t, 1H); 2.65 (t, 1H); 2.55 (t, 1H); 2.30 (m, 1H); 1.65 (br, 2H); 0.95 (s, 3H) ppm.

Example 44

N-{4-[(3R,4R,5S)-3-Amino-4-hydroxy-5-methylpiperidin-1-yl]pyridin-3-yl}-7-(1-ethyl-1H-pyrazol-4-yl)quinoline-2-carboxamide

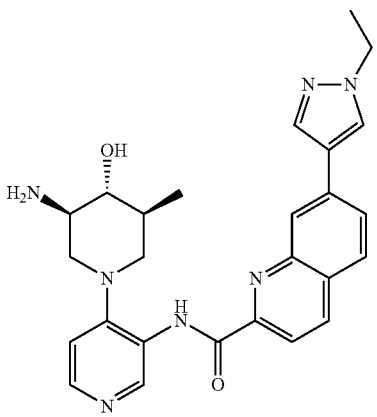 [SMILES: CCn1cc(-c2ccc3ccc(C(=O)Nc4cnccc4N4C[C@@H](N)[C@H](O)[C@@H](C)C4)nc3c2)cn1]

The title compound was prepared using procedures similar to that of Example 43 (yield: 25%). LCMS calc. for C$_{26}$H$_{30}$N$_7$O$_2$ (M+H)$^+$: m/z=472.1. Found: 472.1. $^1$H NMR (DMSO-d$_6$): δ 10.81 (s, 1H); 9.50 (s, 1H); 8.60 (d, 1H); 8.42 (s, 1H); 8.30 (d, 1H); 8.20 (d, 1H); 8.18 (s, 1H); 8.10 (d, 1H); 8.00 (d, 1H); 7.20 (s, 1H); 5.35 (s, 1H); 4.20 (q, 2H); 3.20-3.30 (m, 3H); 2.85 (t, 1H); 2.65 (t, 1H); 2.55 (t, 1H); 2.30 (m, 1H); 1.65 (br, 2H); 1.45 (t, 3H); 0.95 (s, 3H) ppm.

Example 45

N-{4-[(3R,4R,5S)-3-Amino-4-hydroxy-5-methylpiperidin-1-yl]pyridin-3-yl}-7-(6-methoxypyridin-3-yl)quinoline-2-carboxamide

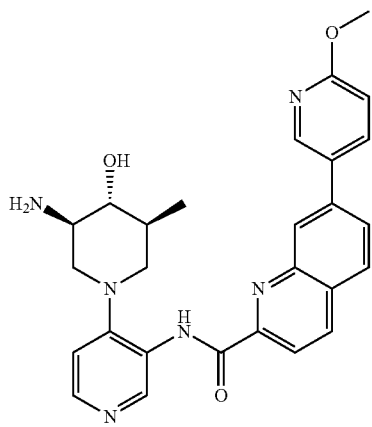 [SMILES: COc1ccc(-c2ccc3ccc(C(=O)Nc4cnccc4N4C[C@@H](N)[C@H](O)[C@@H](C)C4)nc3c2)cn1]

In a microwave tube, a mixture of tert-butyl {(3R,4R,5S)-4-{[tert-butyl(dimethyl)silyl]oxy}-1-[3-({[7-(6-methoxypyridin-3-yl)quinolin-2-yl]carbonyl}amino)pyridin-4-yl]-5-methylpiperidin-3-yl}carbamate (100 mg, 15 mmol), (6-methoxypyridin-3-yl)boronic acid (29 mg, 0.19 mmol), and DIPEA (0.078 mL, 0.45 mmol) in 1,4-dioxane (4.1 mL) and water (0.40 mL) was purged with N$_2$ for 5 min. before bis(tri-t-butylphosphine)palladium (20 mg, 0.04 mmol) was added. The reaction mixture was then heated at 110° C. for 1 h. The crude mixture was diluted with EtOAc and washed with saturated NaHCO$_3$ solution and brine, dried over Na$_2$SO$_4$, and concentrated. The residue was purified by silica gel column chromatography (40 g column, eluting with 0-100% EtOAc in hexanes) to give the coupling product. LCMS (M+H): 699.2.

The above coupling product was dissolved in small amount of MeOH and 4 N HCl was added and the resulting mixture was stirred at room temperature for 1 h. The solvent was removed and a few drops aq. NH$_4$Cl was added. The resulting mixture was purified by preparative LCMS (pH=10 method; XBridge™ preparative C18 5 m OBD™ column) to give the title product. LCMS calc. for C$_{27}$H$_{29}$N$_6$O$_3$ (M+H)$^+$: m/z=485.2. Found: 485.1. $^1$H NMR (DMSO-d$_6$): δ 10.75 (br, 1H); 9.50 (s, 1H); 8.80 (s, 1H); 8.70 (d, 1H); 8.40 (s, 1H); 8.30 (m, 2H); 8.22 (d, 1H); 8.15 (d, 1H); 7.20 (s, 1H); 7.00 (d, 1H); 5.15 (s, 1H); 3.95 (s, 3H); 3.20 (m, 2H); 2.85 (t, 1H); 2.60 (t, 1H); 2.50 (t, 1H); 2.25 (m, 1H); 0.95 (d, 3H) ppm.

Example 46

N-{4-[(3R,4R,5S)-3-Amino-4-hydroxy-5-methylpiperidin-1-yl]pyridin-3-yl}-7-(6-morpholin-4-ylpyridin-3-yl)quinoline-2-carboxamide

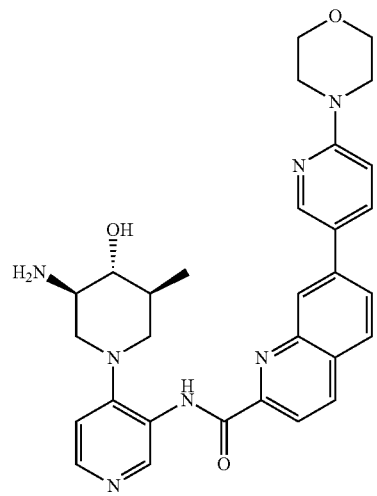 [SMILES: C[C@H]1CN(c2ccncc2NC(=O)c2ccc3ccc(-c4ccc(N5CCOCC5)nc4)cc3n2)C[C@@H](N)[C@@H]1O]

The title compound was prepared using procedures similar to that of Example 45. LCMS calc. for C$_{30}$H$_{34}$N$_7$O$_3$ (M+H)$^+$: m/z=540.3. Found: 540.1. $^1$H NMR (DMSO-d$_6$): δ 10.65 (br, 1H); 9.50 (s, 1H); 8.75 (s, 1H); 8.65 (d, 1H); 8.35 (s, 1H); 8.25 (m, 2H); 8.20 (m, 2H); 8.15 (d, 1H); 7.15 (d, 1H); 6.95 (d, 1H); 5.10 (d, 1H); 3.75 (m, 4H); 3.10-3.30 (m, 3H); 2.85 (t, 1H); 2.65 (m, 2H); 2.25 (m, 1H); 1.70 (br, 2H); 0.95 (d, 3H) ppm.

Example 47

N-(4-((3R,4R,5S)-3-Amino-4-hydroxy-5-methylpiperidin-1-yl)pyridin-3-yl)-7-(pyridin-3-yl)quinoline-2-carboxamide

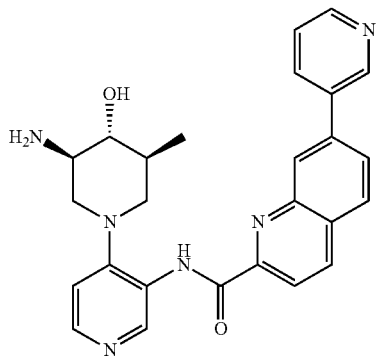 [SMILES: C[C@H]1CN(c2ccncc2NC(=O)c2ccc3ccc(-c4cccnc4)cc3n2)C[C@@H](N)[C@@H]1O]

The title compound was prepared using a method analogous to that of Example 45. LCMS calc. for $C_{26}H_{27}N_6O_2$ $(M+H)^+$: m/z=455.2. Found: 455.2.

Example 48

N-{4-[(3S,5R)-3-amino-5-methylpiperidin-1-yl]pyridin-3-yl}-7-(1-methyl-1H-pyrazol-4-yl)quinoline-2-carboxamide

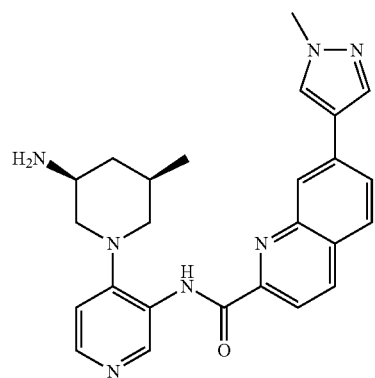 [SMILES: C[C@@H]1C[C@H](N)CN(c2ccncc2NC(=O)c2ccc3ccc(-c4cnn(C)c4)cc3n2)C1]

Step 1. tert-Butyl[(3S,5R)-1-(3-{[(7-bromoquinolin-2-yl)carbonyl]amino}pyridin-4-yl)-5-methylpiperidin-3-yl]carbamate

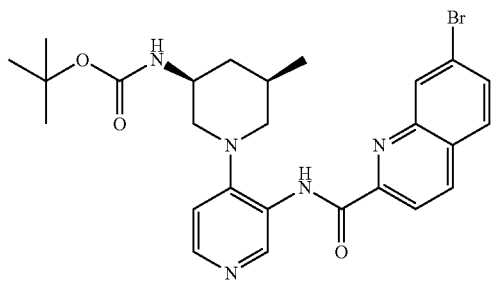 [SMILES: C[C@@H]1C[C@H](NC(=O)OC(C)(C)C)CN(c2ccncc2NC(=O)c2ccc3ccc(Br)cc3n2)C1]

A mixture of tert-butyl [(3S,5R)-1-(3-aminopyridin-4-yl)-5-methylpiperidin-3-yl]carbamate (0.60 g, 2.0 mmol), 7-bromoquinoline-2-carboxylic acid (0.50 g, 2.0 mmol), DIPEA (0.70 mL, 4.0 mmol), and 0.5 g molecular sieves in 1,2-dichloroethane (30 mL) was stirred at room temperature for 0.5 h. HATU (0.031 g, 0.082 mmol) was added. The resulting mixture was stirred at room temperature overnight, diluted with EtOAc (50 mL), filtered through a diatomaceous earth funnel, washed with saturated NaHCO$_3$, water and brine, and then dried over Na$_2$SO$_4$. After concentrating under reduced pressure, the residue was purified with 40 g silica gel column using a CombiFlash® apparatus eluting with EtOAc/hexanes (10-100%) to give the product as brown solid (0.95 g, 90%). LCMS calc. for $C_{26}H_{31}BrN_5O_3$ $(M+H)^+$: m/z=540.2. Found: 540.2.

Step 2. N-{4-[(3S,5R)-3-Amino-5-methylpiperidin-1-yl]pyridin-3-yl}-7-(1-methyl-1H-pyrazol-4-yl)quinoline-2-carboxamide In a microwave tube, a mixture of tert-butyl [(3S,5R)-1-(3-{[(7-bromoquinolin-2-yl)carbonyl]amino}pyridin-4-yl)-5-methylpiperidin-3-yl]carbamate (80 mg, 0.15 mmol), (1-methyl-1H-pyrazol-4-yl)boronic acid (24 mg, 0.19 mmol), and DIPEA (0.078 mL, 0.45 mmol) in 1,4-dioxane (4.1 mL) and water (0.40 mL) was purged with N$_2$ for 5 min. before bis(tri-t-butylphosphine)palladium (20 mg, 0.04 mmol) was added. The reaction mixture was heated at 110° C. for 1 h. The crude mixture was diluted with EtOAc and washed with saturated NaHCO$_3$ solution and brine, dried over Na$_2$SO$_4$ and concentrated. The residue was purified by silica gel column chromatography (40 g column eluting with 0-100% EtOAc in hexanes) to give a Suzuki coupling product. LCMS calc. for $C_{30}H_{36}N_7O_3$ $(M+H)^+$: m/z=542.3. Found: 542.2.

The Suzuki coupling product was dissolved in a small amount of MeOH and 4 N HCl was added. The resulting mixture was stirred at room temperature for 1 h, then concentrated under reduced pressure, and treated with a few drops aq. NH$_4$Cl. The product was purified by preparative LCMS (pH=10 method; XBridge™ preparative C18 5 μm OBD™ column) to give the title product (25%). LCMS calc. for $C_{25}H_{28}N_7O$ $(M+H)^+$: m/z=442.2. Found: 442.1. $^1$H NMR (DMSO-d$_6$): δ 10.55 (br, 1H); 9.45 (s, 1H); 8.60 (d, 1H); 8.35 (s, 1H); 8.30 (d, 1H); 8.20 (m, 2H); 8.15 (d, 1H); 8.10 (s, 1H); 8.00 (d, 1H); 7.20 (d, 1H); 3.95 (s, 3H); 3.20-3.40 (m, 3H); 2.30 (t, 2H); 2.20 (m, 1H); 2.10 (dd, 1H); 1.70 (br, 1H); 0.90 (m, 4H) ppm.

Example 49

N-{4-[(3S,5R)-3-Amino-5-methylpiperidin-1-yl]pyridin-3-yl}-7-(2-cyanophenyl)quinoline-2-carboxamide

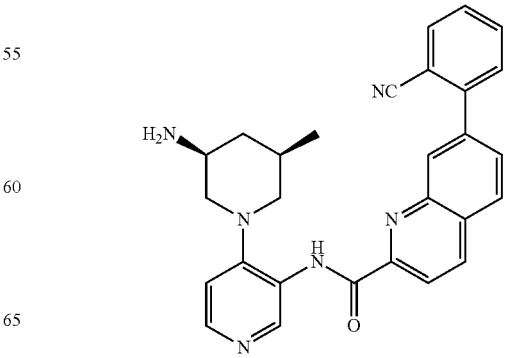

The title compound was prepared using a method analogous to that of Example 48 (30% yield). LCMS calc. for $C_{28}H_{27}N_6O$ (M+H)$^+$: m/z=463.2. Found: 463.1. $^1$H NMR (DMSO-d$_6$): δ 10.55 (br, 1H); 9.45 (s, 1H); 8.80 (d, 1H); 8.40 (d, 1H); 8.35 (d, 1H); 8.30 (d, 1H); 8.10 (d, 1H); 8.00 (d, 1H); 7.90 (t, 1H); 7.85 (d, 1H); 7.70 (t, 1H); 7.15 (d, 1H); 3.20-3.30 (m, 3H); 2.30 (m, 2H); 2.15 (m, 1H); 2.00 (dd, 1H); 1.50 (br, 1H); 0.85 (m, 4H) ppm.

Example 50

N-(4-((3S,5R)-3-Amino-5-methylpiperidin-1-yl)pyridin-3-yl)-7-(4-hydroxypiperidin-1-yl)quinoline-2-carboxamide

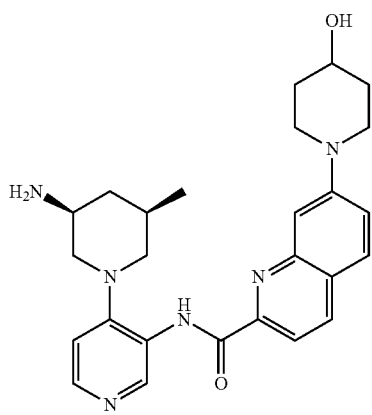 [SMILES: C[C@@H]1C[C@H](N)CN(c2ccncc2NC(=O)c2ccc3ccc(N4CCC(O)CC4)cc3n2)C1]

The title compound was prepared using a method analogous to that of Example 28. LCMS calc. for $C_{26}H_{33}N_6O_2$ (M+H)$^+$: m/z=461.3. Found: 461.2.

Example 51

N-{4-[(3S,5R)-3-Amino-5-(trifluoromethyl)piperidin-1-yl]pyridin-3-yl}-7-(2-cyanophenyl)-1,5-naphthyridine-2-carboxamide

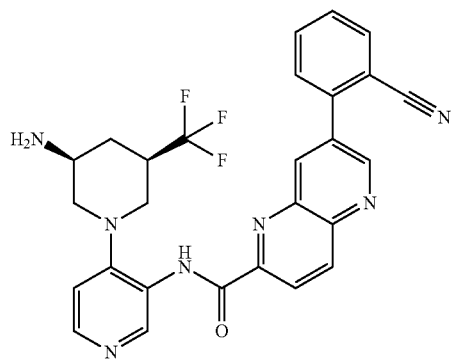 [SMILES: N#Cc1ccccc1-c1cnc2ccc(C(=O)Nc3cnccc3N3C[C@@H](N)C[C@@H](C(F)(F)F)C3)nc2c1]

Step 1. Benzyl (3S,5R)-3-[(tert-butoxycarbonyl)amino]-5-(trifluoromethyl)piperidine-1-carboxylate

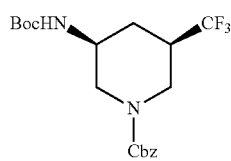 [SMILES: CC(C)(C)OC(=O)N[C@H]1C[C@@H](C(F)(F)F)CN(C(=O)OCc2ccccc2)C1]

To a round bottom flask containing cis-3-(Boc-amino)-5-(trifluoromethyl)piperidine (Molbridge, 10.0 g, 37.3 mmol) and NaHCO$_3$ (18.8 g, 224 mmol) was added THF (200 mL), followed by water (200 mL). To the above mixture, benzyl chloroformate (20.1 g, 112 mmol) was added dropwise over a period of 30 min via syringe pump. The mixture was stirred at room temperature for 2 h. The reaction was diluted with EtOAc and water. The organic layer was washed with brine, dried over Na$_2$SO$_4$, filtered, and concentrated in vacuo. The resulting residue was purified on silica gel (340 g, 15% EtOAc in hexanes) to give as a white foamy solid which was subjected to chiral HPLC separation (Phenomenex Lux Cellulose C-1, 5 μm, 21.2×250 mm column, eluting with 15% EtOH in hexanes, at flow rate of 18 mL/min, with a loading of 100 mg in 1000 μL at 220 nm wavelength) to give the sub-title compound (retention time: 9.1 min) as a white foamy solid (6.51 g, 43%). LCMS calculated for $C_{19}H_{25}F_3N_2NaO_4$ (M+Na)$^+$: m/z=425.2; found 425.2.

Step 2. tert-Butyl [(3S,5R)-5-(trifluoromethyl)piperidin-3-yl]carbamate

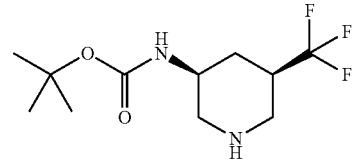 [SMILES: CC(C)(C)OC(=O)N[C@@H]1CNC[C@H](C(F)(F)F)C1]

To a solution of benzyl (3S,5R)-3-[(tert-butoxycarbonyl)amino]-5-(trifluoromethyl)piperidine-1-carboxylate (4.71 g, 11.7 mmol) in MeOH (70.0 mL) was added 10 wt % Pd on carbon (1.886 g). The reaction was purged with H$_2$ and stirred under H$_2$ atmosphere (balloon pressure) for 3 h. The reaction mixture was filtered through a pad of celite (eluted with MeOH). The filtrate was concentrated in vacuo to give the sub-title product as a white solid (3.04 g, 97%) which was used directly in the next step without further purification.

Step 3: tert-Butyl [(3S,5R)-1-(3-nitropyridin-4-yl)-5-(trifluoromethyl)piperidin-3-yl]carbamate

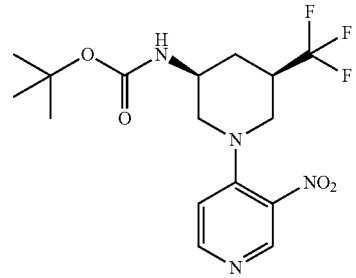 [SMILES: CC(C)(C)OC(=O)N[C@H]1C[C@@H](C(F)(F)F)CN(c2ccncc2[N+](=O)[O-])C1]

A mixture of 4-chloro-3-nitropyridine (580 mg, 3.6 mmol), tert-butyl [(3S,5R)-5-(trifluoromethyl)piperidin-3-yl]carbamate (800 mg, 3 mmol), IPA (5.0 mL) and DIPEA (1.0 mL, 6.0 mmol) was stirred at 80° C. overnight. The reaction mixture was concentrated under reduced pressure and the residue was purified by column chromatography on silica gel using CombiFlash® apparatus eluting with EtOAc/hexane (50-100%). The purification gave 1.0 g (80% yield)

of the sub-title compound as a yellow solid. LCMS calc. for $C_{16}H_{22}F_3N_4O_4$ (M+H)$^+$: m/z=: 391.2; found: 391.1.

Step 4: tert-Butyl [(3S,5R)-1-(3-aminopyridin-4-yl)-5-(trifluoromethyl)piperidin-3-yl]carbamate

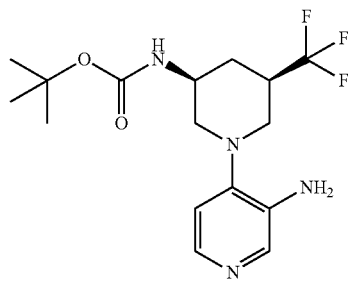

A mixture of tert-butyl [(3S,5R)-1-(3-nitropyridin-4-yl)-5-(trifluoromethyl)piperidin-3-yl]carbamate (1 g, 2 mmol), iron powder (0.57 g, 10 mmol), AcOH (16 mL) and water (2 mL) was stirred at room temperature for 60 min. When the reaction was complete, the mixture was allowed to cool, concentrated under reduced pressure and diluted with EtOAc. The resulting mixture was filtered through a diatomaceous earth pad. The filtrate was concentrated under reduced pressure, and the residue was dissolved in 1 M NaOH aqueous solution and extracted with EtOAc (100 mL, 3×). The combined organic layers were washed with water and brine, dried over $Na_2SO_4$, filtered and concentrated under reduced pressure to give 0.9 g (100% yield) of the sub-title compound as a brown solid. LCMS calc. for $C_{16}H_{24}F_3N_4O_2$ (M+H)$^+$: m/z=: 361.2; found: 361.1.

Step 5. tert-Butyl [(3S,5R)-1-(3-{[(7-Bromo-1,5-naphthyridin-2-yl)carbonyl]amino}pyridin-4-yl)-5-(trifluoromethyl)piperidin-3-yl]carbamate

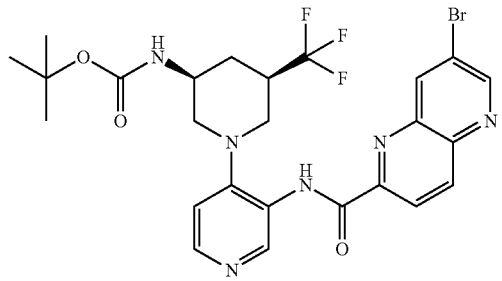 [SMILES: CC(C)(C)OC(=O)N[C@H]1C[C@@H](C(F)(F)F)CN(c2ccncc2NC(=O)c2ccc3ncc(Br)cc3n2)C1]

A mixture of 7-bromo-1,5-naphthyridine-2-carboxylic acid (632 mg, 2.50 mmol), tert-butyl [(3S,5R)-1-(3-aminopyridin-4-yl)-5-(trifluoromethyl)piperidin-3-yl]carbamate (900 mg, 2.50 mmol), HATU (1.71 g, 4.50 mmol) and DIPEA (1.30 mL, 7.49 mmol) in DMF (6 mL) was stirred at RT for 2 h. The reaction was quenched with brine, extracted with EtOAc (2×). The combined organic phases were washed with water, brine and dried over $Na_2SO_4$, and then concentrated. The residue was purified by Combi-Flash eluted with EtOAc/hexanes (0-100%) to give the sub-title product as off-white solid (1.03 g, 69%). LCMS calc. for $C_{25}H_{27}BrF_3N_6O_3$ (M+H)$^+$: m/z=: 595.1; found: 595.0.

Step 6

N-{4-[(3S,5R)-3-Amino-5-(trifluoromethyl)piperidin-1-yl]pyridin-3-yl}-7-(2-cyanophenyl)-1,5-naphthyridine-2-carboxamide In a sealed tube a mixture of (2-cyanophenyl)boronic acid (12 mg, 0.079 mmol), and tert-butyl [(3S,5R)-1-(3-{[(7-bromo-1,5-naphthyridin-2-yl)carbonyl]amino}pyridin-4-yl)-5-(trifluoromethyl)piperidin-3-yl]carbamate (30 mg, 0.61 mmol) in 1,4-dioxane (2 mL) and water (0.2 mL) was purged with $N_2$ for 5 min before bis(tri-t-butylphosphine)palladium (3 mg, 0.1 mmol) was added. The reaction mixture was then heated on the benchtop at 110° C. for 1 h. The mixture was concentrated, and the resulting residue was purified by silica gel column chromatography eluting with EtOAc/hexanes (0-100%) to give tert-butyl [(3S,5R)-1-[3-({[7-(2-cyanophenyl)-1,5-naphthyridin-2-yl]carbonyl}amino)pyridin-4-yl]-5-(trifluoromethyl)piperidin-3-yl]carbamate. The above made Suzuki product was treated with DCM (1 mL) and TFA (1 mL) at RT for 1 h. The mixture was concentrated. The residue was purified by prep. LC/MS (PH=10) to yield the title product as white powder. LCMS calc. for $C_{27}H_{23}F_3N_7O$ (M+H)$^+$: m/z=: 518.2; found: 518.2.

Example 52. N-{4-[(3R,4R,5S)-3-Amino-4-hydroxy-5-methylpiperidin-1-yl]pyridin-3-yl}-7-[6-(tetrahydro-2H-pyran-4-yloxy)pyridin-3-yl]quinoline-2-carboxamide

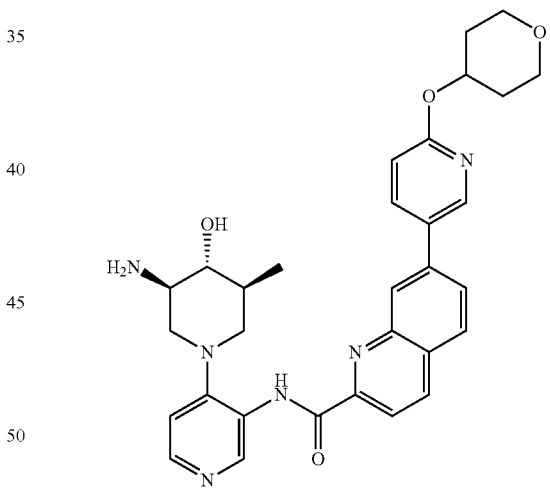

In a sealed tube a mixture of tert-butyl ((3R,4R,5S)-1-(3-{[(7-bromoquinolin-2-yl)carbonyl]amino}pyridin-4-yl)-4-{[tert-butyl(dimethyl)silyl]oxy}-5-methylpiperidin-3-yl)carbamate (50 mg, 0.07 mmol), [6-(tetrahydro-2H-pyran-4-yloxy)pyridin-3-yl]boronic acid (21 mg, 0.095 mmol), and DIPEA (0.039 mL, 0.22 mmol) in 1,4-dioxane (2.0 mL) and water (0.2 mL) was purged with $N_2$ for 5 min before bis(tri-t-butylphosphine)palladium (10 mg, 0.02 mmol) was added. The reaction mixture was then heated on the bench top at 110° C. for 1 h. The crude was purified by silica gel column chromatography eluted with EtOAc/hexanes (40 g column, 0-100% EtOAc in hexanes), to give tert-butyl ((3R,4R,5S)-4-{[tert-butyl(dimethyl)silyl]oxy}-5-methyl-1-{3-[({7-[6-(tetrahydro-2H-pyran-4-yloxy)pyridin-3-yl]quinolin-2-yl}carbonyl)amino]pyridin-4-yl}piperidin-3-yl)carbamate. The above made Suzuki product was dissolved in MeOH, and 4 N HCl was added and the resulting mixture was stirred for 1 h at r.t. The reaction mixture was concentrated and treated with aq. NH$_4$OH and then purified with pH 10 prep-LCMS to give the title product. LCMS calc. for C$_{31}$H$_{35}$N$_6$O$_4$ (M+H)$^+$: m/z: 555.3; found: 555.1.

Example A

Pim Enzyme Assays

Pim-1 and Pim-3 kinase assays-20 μL reactions were run in white 384 well polystyrene plates dotted with 0.8 μL compound/DMSO in the assay buffer (50 mM Tris, pH 7.5, 0.01% Tween-20, 5 mM mgCl$_2$, 0.01% BSA, 5 mM DTT), containing 0.05 μM Biotin-labeled BAD peptide substrate (AnaSpec 62269), 1 mM ATP, and 2.5 pM (Pim-1, Invitrogen PV3503) or 1.25 pM (Pim-3, Millipore 14-738) enzyme for 1 h at 25° C. Reactions were stopped by addition of 10 μL STOP Buffer (150 mM Tris, pH=7.5, 150 mM NaCl, 75 mM EDTA, 0.01% Tween-20, 0.3% BSA), supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 μg/mL each. Supplementation of the STOP buffer with beads and stopping the reactions were done under reduced light. Prior to the stopping reactions STOP buffer with beads was preincubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay-20 μL reactions were run in white 384 well polystyrene plates dotted with 0.8 μL compound/DMSO in the assay buffer (50 mM Tris, pH 7.5, 0.01% Tween-20, 5 mM mgCl$_2$, 0.01% BSA, 5 mM DTT), containing 0.05 μM Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 μL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an IC$_{50}$ of 2 μM or less when tested for PIM kinase activity under the assay conditions disclosed above are considered active.

Although the above in vitro assays are conducted at 1 mM ATP compounds can also be evaluated for potency and in vitro activity against PIM targets utilizing K$_m$ conditions, where the concentration of ATP is set to the K$_m$ value and the assay is more sensitive to PIM inhibition activity.

Example B

Pim Cellular Assays

One or more compounds of the invention were tested for inhibitory activity of PIM according to at least one of the following cellular assays. Compounds of the invention having an IC$_{50}$ of 10 μM or less when tested for PIM kinase activity under the cellular assay conditions disclosed below would be and were considered active.

Pim Cell Proliferation Assay

KG-1A cells are purchased from ATCC (Manassas, Va.) and KMS. 12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the anti-proliferation activity of test compounds, both cell lines are plated with the culture medium (2×10$^3$ cells/well/in 200 μL) into 96-well polystyrene ultralow binding (Costar), in the presence or absence of a concentration range of test compounds. After 4 days, [$^3$H]-thymidine, 1 μCi/10 μL/well (PerkinElmer, Boston, Mass.) in culture medium is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). IC$_{50}$ determination is performed by fitting the curve of percent inhibition versus the log of the inhibitor concentration using the GraphPad Prism 5.0 software.

Pim Cell Proliferation Assay

MOLM-16 cells are purchased from DSMZ (Germany) and maintained in the culture medium recommended, RPMI, 20% FBS. To measure the anti-proliferation activity of test compounds, the cells are plated with the RPMI, 10% FBS (1×10$^4$ cells/well/in 200 μL) into 96-well polystyrene ultralow binding plates (Costar) in the presence or absence of a concentration range of test compounds. After 4 days, [$^3$H]-thymidine, 1 μCi/10 μL/well (PerkinElmer, Boston, Mass.) in RPMI, 10% FBS is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). IC$_{50}$ determination is performed by fitting the curve of percent inhibition versus the log of the inhibitor concentration using the GraphPad Prism 5.0 software.

Pim pBAD Signaling Assays

KG-1A cells are purchased from ATCC (Manassas, Va.) and KMS. 12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium (1×10$^6$/well/100 μL for KG1A and 4×10$^5$ cells/well/in 100 μL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS.12.BM cells and 4 h for KG1-A cells. Plates are centrifuged at 2000 RPM for 10 min. and supernatants aspirated. 100 μL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80° C. To measure the pBAD activity, a Cell Signaling ELISA kit (Cell Signaling Path Scan phosphor pBAD ELISA) is utilized. 50 μL of the lysate is tested per the ELISA protocol and the data analysis is performed by software on a SpectrMax5 plate reader (Molecular Devices, Sunnyvale, Calif.). IC$_{50}$ determination is performed by fitting the curve of percent inhibition versus the log of the inhibitor concentration using the GraphPad Prism 5.0 software.

Data obtained for the Example compounds, obtained using the methods described in Example A, are provided in Table 1.

TABLE 1

| Example | PIM1 IC$_{50}$ (nM)$^a$ | PIM2 IC$_{50}$ (nM)$^b$ | PIM3 IC$_{50}$ (nM)$^a$ | KMS.12.BM pBAD IC$_{50}$ (nM)$^c$ |
|---|---|---|---|---|
| 1 | * | + | * | # |
| 2 | * | + | * | # |
| 3 | * | ++ | * | # |
| 4 | * | + | * | # |
| 5 | * | ++ | * | # |
| 6 | * | + | * | # |
| 7 | * | + | * | # |
| 8 | * | ++ | * | # |
| 9 | * | ++ | * | # |
| 10 | * | + | * | # |
| 11 | * | ++ | * | ## |
| 12 | * | + | * | # |
| 13 | * | + | * | # |
| 14 | * | + | * | ## |
| 15 | * | ++ | * | ## |
| 16 | * | + | * | # |
| 17 | * | ++ | * | ## |
| 18 | * | ++ | * | ## |
| 19 | * | ++ | * | ### |
| 20 | * | + | * | ## |
| 21 | * | ++ | * | ## |
| 22 | * | + | * | # |
| 23 | * | + | * | # |
| 24 | * | + | * | # |
| 25 | * | + | * | # |
| 26 | * | + | * | ## |
| 27 | * | ++ | * | ## |
| 28 | * | ++ | * |  |
| 29 | * | ++ | * |  |
| 30 | * | + | * | ## |
| 31 | * | ++ | * | ## |
| 32 | * | ++ | * |  |
| 33 | * | +++ | * |  |
| 34 | * | + | * | ## |
| 35 | * | + | * | # |
| 36 | * | + | * | # |
| 37 | * | + | * | # |
| 38 | * | + | * | # |
| 39 | * | + | * | ## |
| 40 | * | ++ | * |  |
| 41 | ** | +++ | ** | ## |
| 42 | * | ++ | * | ## |
| 43 | * | + | * | # |
| 44 | * | + | * | # |
| 45 | * | + | * | # |
| 46 | * | + | * | # |
| 47 | * | + | * | # |
| 48 | * | + | * | # |
| 49 | * | + | * | # |
| 50 | * | + | * | # |
| 51 | * | + | * | # |
| 52 | * | + | * | ## |

$^a$IC$_{50}$ ≤ 10 nM: *; 10 nM < IC$_{50}$ ≤ 50 nM: ; 50 nM < IC$_{50}$ ≤ 500 nM: *; 500 nM < IC$_{50}$ ≤ 2000 nM: ****.
$^b$IC$_{50}$ ≤ 100 nM: +; 100 nM < IC$_{50}$ ≤ 1000 nM: ++; 1000 nM < IC$_{50}$ ≤ 10000 nM: +++.
$^c$IC$_{50}$ ≤ 50 nM: #; 50 nM < IC$_{50}$ ≤ 250 nM: ##; 250 nM < IC$_{50}$ ≤ 2000 nM: ###; 2000 nM < IC$_{50}$ ≤ 10000 nM: ####.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of treating a disease or disorder comprising administering to a patient in need of such treatment a therapeutically effective amount of a compound of any one of the following Formulae (III) to (VIII):

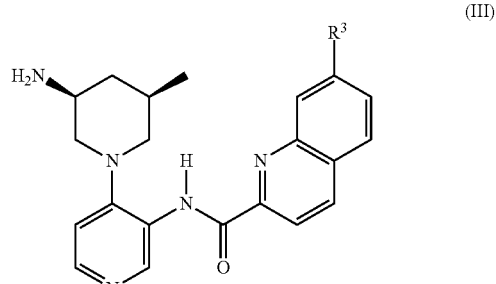

(III)

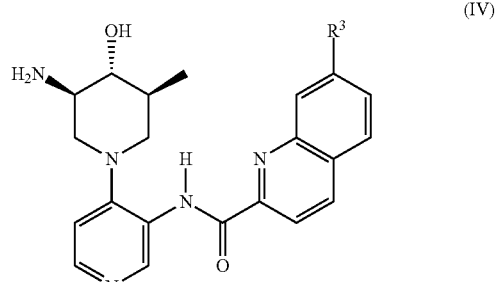

(IV)

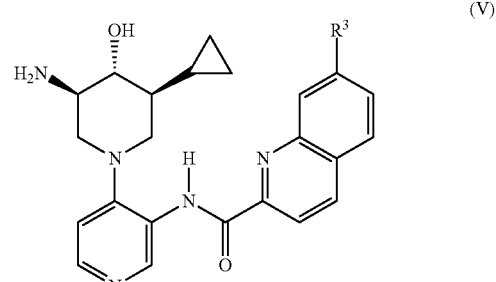

(V)

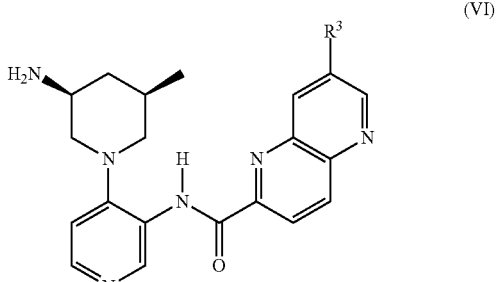

(VI)

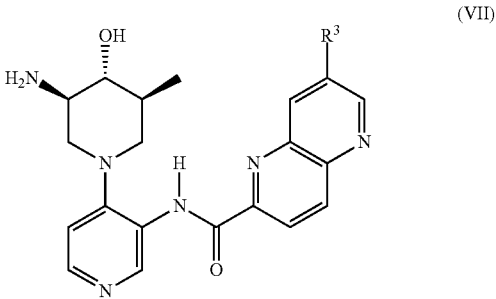

(VII)

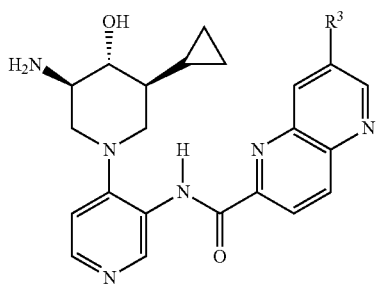

(VIII)

or a pharmaceutically acceptable salt thereof, wherein:
R$^3$ is C$_{1-6}$ alkyl, Cy, or -L-Cy;
L is unsubstituted C$_{1-6}$ alkylene or C$_{1-6}$ alkylene substituted with 1, 2 or 3 substituents independently selected from F, Cl, CN, OH and O (C$_{1-6}$ alkyl);
Cy is unsubstituted or substituted C$_{6-10}$ aryl, unsubstituted or substituted 5-10 membered heteroaryl, unsubstituted or substituted C$_{3-6}$ cycloalkyl or unsubstituted or substituted 4-11 membered heterocycloalkyl,
wherein the substituted C$_{6-10}$ aryl, 5-10 membered heteroaryl, C$_{3-6}$ cycloalkyl or 4-11 membered heterocycloalkyl forming Cy is substituted with 1, 2, or 3 substituents each independently selected from halogen, R$^{Cy1}$, C$_{6-10}$ aryl, C$_{3-7}$ cycloalkyl, 5-10 membered heteroaryl, 4-7 membered heterocycloalkyl, C$_{1-6}$ haloalkyl, CN, OH, and C$_{1-6}$ alkoxy;
wherein each R$^{Cy1}$ is, independently, C$_{1-6}$ alkyl, each of which is independently unsubstituted or substituted with 1, 2 or 3 substituents independently selected from halogen, CN, and OR$^{a1}$; and
wherein R$^{a1}$ is independently, at each occurrence, selected from H, C$_{1-6}$ alkyl, C$_{2-6}$ alkenyl, and C$_{2-6}$ alkynyl,
wherein the disease or disorder is a myeloproliferative disorder, or a cancer selected from a solid tumor and a hematological cancer.

2. The method of claim 1, wherein the cancer is a cancer wherein the expression or activity of at least one of Pim1, Pim2 and Pim3 is upregulated.

3. The method of claim 1, wherein the cancer is a cancer wherein an oncogene is activated.

4. The method of claim 1, wherein the cancer is a cancer wherein Myc or Bcl2 is activated.

5. The method of claim 1 wherein R$^3$ is C$_{1-6}$ alkyl.

6. The method of claim 1 wherein R$^3$ is Cy.

7. The method of claim 1 wherein R$^3$ is -L-Cy.

8. The method of claim 6 wherein Cy is unsubstituted or substituted C$_{6-10}$ aryl.

9. The method of claim 8 wherein Cy is unsubstituted phenyl or substituted phenyl.

10. The method of claim 9 wherein Cy is phenyl substituted with 1, 2, or 3 substituents independently selected from halogen, CN, and OR$^{a1}$.

11. The method of claim 6 wherein Cy is unsubstituted or substituted 5-10 membered heteroaryl.

12. The method of claim 11 wherein Cy is unsubstituted or substituted pyridinyl or pyrazolyl.

13. The method of claim 12 wherein Cy is pyridinyl substituted with 1 substituent selected from C$_{6-10}$ aryl, C$_{3-7}$ cycloalkyl, 5-10 membered heteroaryl, 4-7 membered heterocycloalkyl, OH, and C$_{1-6}$ alkoxy.

14. The method of claim 13 wherein Cy is 6-(morpholin-4-yl)pyridin-3-yl or 6-methoxypyridin-3-yl.

15. The method of claim 12 wherein Cy is pyrazolyl substituted with a C$_{1-6}$ alkyl group.

16. The method of claim 15 wherein Cy is 1-methyl-1H-pyrazol-4-yl or 1-ethyl-1H-pyrazol-4-yl.

17. The method of claim 6 wherein Cy is unsubstituted or substituted C$_{3-6}$ cycloalkyl.

18. The method of claim 6 wherein Cy is unsubstituted or substituted 4-11 membered heterocycloalkyl.

19. The method of claim 18 wherein Cy is unsubstituted or substituted heterocycloalkyl, the ring atoms of which consist of carbon atoms and 1, 2, or 3 heteroatoms independently selected from N and O.

20. The method of claim 18 wherein a nitrogen atom of Cy forms the bond between Cy and the remainder of the molecule.

21. The method of claim 19 wherein Cy is unsubstituted or substituted pyrrolidinyl, piperidinyl, azetidinyl, piperazinyl or oxopiperazinyl.

22. The method of claim 21 wherein Cy is unsubstituted pyrrolidin-1-yl or is pyrrolidin-1-yl substituted with a C$_{1-6}$ haloalkyl group.

23. The method of claim 21 wherein Cy is unsubstituted piperidin-1-yl or piperidin-1-yl substituted at the 4-position.

24. The method of claim 23 wherein Cy is substituted piperidin-1-yl substituted by 1 substituent selected from R$^{Cy2}$, CN, and OR$^a$.

25. The method of claim 24 wherein Cy is 4-hydroxypiperidin-1-yl, 4-cyanopiperidin-1-yl, 4-methoxypiperidin-1-yl, 4-(pyridin-4-yl)piperidin-1-yl, or 4-(morpholin-4-yl)piperidin-1-yl.

26. The method of claim 21 wherein Cy is unsubstituted azetidin-1-yl or azetidin-1-yl substituted with two C$_{1-6}$ alkyl groups.

27. The method of claim 21 wherein Cy is unsubstituted or substituted piperazin-1-yl.

28. The method of claim 27 wherein Cy is 4-methylpiperazin-1-yl or 4-ethylpiperazin-1-yl.

29. The method of claim 21 wherein Cy is unsubstituted or substituted 3-oxopiperazin-1-yl.

30. The method of claim 29 wherein Cy is 4-methyl-3-oxopiperazin-1-yl or 4-ethyl-3-oxopiperazin-1-yl.

31. The method of claim 19 wherein Cy is unsubstituted or substituted 3-oxa-9-azaspiro[5.5]undecanyl, 1-oxa-8-azaspiro[4.5]decanyl, or morpholinyl.

32. The method of claim 9 wherein Cy is unsubstituted or substituted heterocycloalkyl, the ring atoms of which consist of carbon atoms and 1 oxygen atom.

33. The method of claim 1 wherein L is unsubstituted C$_{1-6}$ alkylene.

34. The method of claim 33 wherein L is CH$_2$.

35. The method of claim 1 wherein each R$^{Cy1}$ is methyl or ethyl.

36. The method of claim 1 wherein Cy is substituted with a 4 to 7 membered heterocycloalkyl.

37. The method of claim 1 wherein R$^{a1}$ is selected from H and C$_{1-6}$ alkyl.

38. A method of treating a disease or disorder comprising administering to a patient in need of such treatment a therapeutically effective amount of a compound selected from the following compounds:
N-{4-[3-amino-5-methylpiperidin-1-yl]pyridin-3-yl}-7-(2,6-difluorophenyl)-1,5-naphthyridine-2-carboxamide;
N-{4-[3-amino-5-methylpiperidin-1-yl]pyridin-3-yl}-7-isopropyl-1,5-naphthyridine-2-carboxamide;

N-{4-[3-amino-5-methylpiperidin-1-yl]pyridin-3-yl}-7-(tetrahydro-2H-pyran-4-yl)-1,5-naphthyridine-2-carboxamide;
N-{4-[3-amino-5-methylpiperidin-1-yl]pyridin-3-yl}-7-(2,6-difluoro-4-methoxyphenyl)-1,5-naphthyridine-2-carboxamide;
N-{4-[3-amino-5-methylpiperidin-1-yl]pyridin-3-yl}-7-(1-ethyl-1H-pyrazol-4-yl)-1,5-naphthyridine-2-carboxamide;
N-{4-[3-amino-4-hydroxy-5-methylpiperidin-1-yl]pyridin-3-yl}-7-isopropenyl-1,5-naphthyridine-2-carboxamide;
N-{4-[3-amino-4-hydroxy-5-methylpiperidin-1-yl]pyridin-3-yl}-7-(6-methoxypyridin-3-yl)-1,5-naphthyridine-2-carboxamide;
N-{4-[3-amino-4-hydroxy-5-methylpiperidin-1-yl]pyridin-3-yl}-7-morpholin-4-yl-1,5-naphthyridine-2-carboxamide;
N-{4-[3-amino-4-hydroxy-5-methylpiperidin-1-yl]pyridin-3-yl}-7-ethylquinoline-2-carboxamide;
N-{4-[3-amino-4-hydroxy-5-methylpiperidin-1-yl]pyridin-3-yl}-7-isopropylquinoline-2-carboxamide;
N-{4-[3-amino-4-hydroxy-5-methylpiperidin-1-yl]pyridin-3-yl}-7-(tetrahydro-2H-pyran-4-yl)quinoline-2-carboxamide;
N-{4-[3-amino-4-hydroxy-5-methylpiperidin-1-yl]pyridin-3-yl}-7-morpholin-4-ylquinoline-2-carboxamide;
N-{4-[3-amino-5-methylpiperidin-1-yl]pyridin-3-yl}-7-morpholin-4-ylquinoline-2-carboxamide;
N-{4-[3-amino-4-hydroxy-5-methylpiperidin-1-yl]pyridin-3-yl}-7-(3-oxa-9-azaspiro[5.5]undec-9-yl)quinoline-2-carboxamide;
N-{4-[3-amino-5-methylpiperidin-1-yl]pyridin-3-yl}-7-(3-oxa-9-azaspiro[5.5]undec-9-yl)quinoline-2-carboxamide;
N-{4-[3-amino-4-hydroxy-5-methylpiperidin-1-yl]pyridin-3-yl}-7-(4-cyanopiperidin-1-yl)quinoline-2-carboxamide;
N-{4-[3-amino-5-methylpiperidin-1-yl]pyridin-3-yl}-7-(4-cyanopiperidin-1-yl)quinoline-2-carboxamide;
N-{4-[3-amino-4-hydroxy-5-methylpiperidin-1-yl]pyridin-3-yl}-7-(4-methylpiperazin-1-yl)quinoline-2-carboxamide;
N-{4-[3-amino-5-methylpiperidin-1-yl]pyridin-3-yl}-7-(4-methylpiperazin-1-yl)quinoline-2-carboxamide;
N-{4-[3-amino-4-hydroxy-5-methylpiperidin-1-yl]pyridin-3-yl}-7-(4-pyridin-4-ylpiperidin-1-yl)quinoline-2-carboxamide;
N-{4-[3-amino-5-methylpiperidin-1-yl]pyridin-3-yl}-7-(4-pyridin-4-ylpiperidin-1-yl)quinoline-2-carboxamide;
N-{4-[3-amino-4-hydroxy-5-methylpiperidin-1-yl]pyridin-3-yl}-7-(4-ethyl-3-oxopiperazin-1-yl)quinoline-2-carboxamide;
N-{4-[3-amino-5-methylpiperidin-1-yl]pyridin-3-yl}-7-(4-ethyl-3-oxopiperazin-1-yl)quinoline-2-carboxamide;
N-{4-[3-amino-4-hydroxy-5-methylpiperidin-1-yl]pyridin-3-yl}-7-(4-methoxypiperidin-1-yl)quinoline-2-carboxamide;
N-{4-[3-amino-5-methylpiperidin-1-yl]pyridin-3-yl}-7-(4-methoxypiperidin-1-yl)quinoline-2-carboxamide;
N-{4-[3-amino-4-hydroxy-5-methylpiperidin-1-yl]pyridin-3-yl}-7-(4-morpholin-4-ylpiperidin-1-yl)quinoline-2-carboxamide;
N-{4-[3-amino-5-methylpiperidin-1-yl]pyridin-3-yl}-7-(4-morpholin-4-ylpiperidin-1-yl)quinoline-2-carboxamide;
N-{4-[3-amino-4-hydroxy-5-methylpiperidin-1-yl]pyridin-3-yl}-7-[3-(trifluoromethyl)pyrrolidin-1-yl]quinoline-2-carboxamide;
N-{4-[3-amino-5-methylpiperidin-1-yl]pyridin-3-yl}-7-[3-(trifluoromethly)pyrrolidin-1-yl]quinoline-2-carboxamide;
N-{4-[3-amino-4-hydroxy-5-methylpiperidin-1-yl]pyridin-3-yl}-7-pyrrolidin-1-ylquinoline-2-carboxamide;
N-{4-[3-amino-5-methylpiperidin-1-yl]pyridin-3-yl}-7-pyrrolidin-1-ylquinoline-2-carboxamide;
N-{4-[3-amino-4-hydroxy-5-methylpiperidin-1-yl]pyridin-3-yl}-7-(3,3-dimethylazetidin-1-yl)quinoline-2-carboxamide;
N-{4-[3-amino-5-methylpiperidin-1-yl]pyridin-3-yl}-7-(3,3-dimethylazetidin-1-yl)quinoline-2-carboxamide;
N-{4-[3-amino-5-methylpiperidin-1-yl]pyridin-3-yl}-7-azetidin-1-ylquinoline-2-carboxamide;
N-{4-[3-amino-5-cyclopropyl-4-hydroxypiperidin-1-yl]pyridin-3-yl}-7-(2,6-difluoro-4-methoxyphenyl)-1,5-naphthyridine-2-carboxamide;
N-{4-[3-amino-5-cyclopropyl-4-hydroxypiperidin-1-yl]pyridin-3-yl}-7-(6-methoxypyridin-3-yl)-1,5-naphthyridine-2-carboxamide;
N-{4-[3-amino-5-cyclopropyl-4-hydroxypiperidin-1-yl]pyridin-3-yl}-7-(6-morpholin-4-ylpyridin-3-yl)-1,5-naphthyridine-2-carboxamide;
N-{4-[3-amino-5-cyclopropyl-4-hydroxypiperidin-1-yl]pyridin-3-yl}-7-(1-ethyl-1H-pyrazol-4-yl)-1,5-naphthyridine-2-carboxamide;
N-{4-[3-amino-5-cyclopropyl-4-hydroxypiperidin-1-yl]pyridin-3-yl}-7-(1-methyl-1H-pyrazol-4-yl)-1,5-naphthyridine-2-carboxamide;
N-{4-[3-amino-5-cyclopropyl-4-hydroxypiperidin-1-yl]pyridin-3-yl}-7-(3-oxa-9-azaspiro[5.5]undec-9-yl)-1,5-naphthyridine-2-carboxamide;
N-{4-[3-amino-5-cyclopropyl-4-hydroxypiperidin-1-yl]pyridin-3-yl}-7-(4-cyanopiperidin-1-yl)-1,5-naphthyridine-2-carboxamide;
N-{4-[3-amino-5-cyclopropyl-4-hydroxypiperidin-1-yl]pyridin-3-yl}-7-(1-oxa-8-azaspiro[4.5]dec-8-yl)-1,5-naphthyridine-2-carboxamide;
N-{4-[3-amino-4-hydroxy-5-methylpiperidin-1-yl]pyridin-3-yl}-7-(1-methyl-1H-pyrazol-4-yl)quinoline-2-carboxamide;
N-{4-[3-amino-4-hydroxy-5-methylpiperidin-1-yl]pyridin-3-yl}-7-(1-ethyl-1H-pyrazol-4-yl)quinoline-2-carboxamide;
N-{4-[3-amino-4-hydroxy-5-methylpiperidin-1-yl]pyridin-3-yl}-7-(6-methoxypyridin-3-yl)quinoline-2-carboxamide;
N-{4-[3-amino-4-hydroxy-5-methylpiperidin-1-yl]pyridin-3-yl}-7-(6-morpholin-4-ylpyridin-3-yl)quinoline-2-carboxamide;
N-(4-(3-amino-4-hydroxy-5-methylpiperidin-1-yl)pyridin-3-yl)-7-(pyridin-3-yl)quinoline-2-carboxamide;
N-{4-[3-amino-5-methylpiperidin-1-yl]pyridin-3-yl}-7-(1-methyl-1H-pyrazol-4-yl)quinoline-2-carboxamide;
N-{4-[3-amino-5-methylpiperidin-1-yl]pyridin-3-yl}-7-(2-cyanophenyl)quinoline-2-carboxamide;
N-(4-(3-amino-5-methylpiperidin-1-yl)pyridin-3-yl)-7-(4-hydroxypiperidin-1-yl)quinoline-2-carboxamide;
N-{4-[3-amino-5-(trifluoromethyl)piperidin-1-yl]pyridin-3-yl}-7-(2-cyanophenyl)-1,5-naphthyridine-2-carboxamide; and N-{4-[3-amino-4-hydroxy-5-methylpiperidin-1-yl]pyridin-3-yl}-7-[6-(tetrahydro-2H-pyran-4-yloxy)pyridin-3-yl]quinoline-2-carboxamide, or a pharmaceutically acceptable salt thereof, wherein the disease or disorder is a myeloproliferative disorder, or a cancer selected from a solid tumor and a hematological cancer.

39. A method of treating a disease or disorder comprising administering to a patient in need of such treatment a therapeutically effective amount of a compound selected from the following compounds:

N-{4-[(3S,5R)-3-amino-5-methylpiperidin-1-yl]pyridin-3-yl}-7-(2,6-difluorophenyl)-1,5-naphthyridine-2-carboxamide;

N-{4-[(3S,5R)-3-amino-5-methylpiperidin-1-yl]pyridin-3-yl}-7-isopropyl-1,5-naphthyridine-2-carboxamide;

N-{4-[(3S,5R)-3-amino-5-methylpiperidin-1-yl]pyridin-3-yl}-7-(tetrahydro-2H-pyran-4-yl)-1,5-naphthyridine-2-carboxamide;

N-{4-[(3S,5R)-3-amino-5-methylpiperidin-1-yl]pyridin-3-yl}-7-(2,6-difluoro-4-methoxyphenyl)-1,5-naphthyridine-2-carboxamide;

N-{4-[(3S,5R)-3-amino-5-methylpiperidin-1-yl]pyridin-3-yl}-7-(1-ethyl-1H-pyrazol-4-yl)-1,5-naphthyridine-2-carboxamide;

N-{4-[(3R,4R,5S)-3-amino-4-hydroxy-5-methylpiperidin-1-yl]pyridin-3-yl}-7-isopropenyl-1,5-naphthyridine-2-carboxamide;

N-{4-[(3R,4R,5S)-3-amino-4-hydroxy-5-methylpiperidin-1-yl]pyridin-3-yl}-7-(6-methoxypyridin-3-yl)-1,5-naphthyridine-2-carboxamide;

N-{4-[(3R,4R,5S)-3-amino-4-hydroxy-5-methylpiperidin-1-yl]pyridin-3-yl}-7-morpholin-4-yl-1,5-naphthyridine-2-carboxamide;

N-{4-[(3R,4R,5S)-3-amino-4-hydroxy-5-methylpiperidin-1-yl]pyridin-3-yl}-7-ethylquinoline-2-carboxamide;

N-{4-[(3R,4R,5S)-3-amino-4-hydroxy-5-methylpiperidin-1-yl]pyridin-3-yl}-7-isopropylquinoline-2-carboxamide;

N-{4-[(3R,4R,5S)-3-amino-4-hydroxy-5-methylpiperidin-1-yl]pyridin-3-yl}-7-(tetrahydro-2H-pyran-4-yl)quinoline-2-carboxamide;

N-{4-[(3R,4R,5S)-3-amino-4-hydroxy-5-methylpiperidin-1-yl]pyridin-3-yl}-7-morpholin-4-ylquinoline-2-carboxamide;

N-{4-[(3S,5R)-3-amino-5-methylpiperidin-1-yl]pyridin-3-yl}-7-morpholin-4-ylquinoline-2-carboxamide;

N-{4-[(3R,4R,5S)-3-amino-4-hydroxy-5-methylpiperidin-1-yl]pyridin-3-yl}-7-(3-oxa-9-azaspiro[5.5]undec-9-yl)quinoline-2-carboxamide;

N-{4-[(3S,5R)-3-amino-5-methylpiperidin-1-yl]pyridin-3-yl}-7-(3-oxa-9-azaspiro[5.5]undec-9-yl)quinoline-2-carboxamide;

N-{4-[(3R,4R,5S)-3-amino-4-hydroxy-5-methylpiperidin-1-yl]pyridin-3-yl}-7-(4-cyanopiperidin-1-yl)quinoline-2-carboxamide;

N-{4-[(3S,5R)-3-amino-5-methylpiperidin-1-yl]pyridin-3-yl}-7-(4-cyanopiperidin-1-yl)quinoline-2-carboxamide;

N-{4-[(3R,4R,5S)-3-amino-4-hydroxy-5-methylpiperidin-1-yl]pyridin-3-yl}-7-(4-methylpiperazin-1-yl)quinoline-2-carboxamide;

N-{4-[(3S,5R)-3-amino-5-methylpiperidin-1-yl]pyridin-3-yl}-7-(4-methylpiperazin-1-yl)quinoline-2-carboxamide;

N-{4-[(3R,4R,5S)-3-amino-4-hydroxy-5-methylpiperidin-1-yl]pyridin-3-yl}-7-(4-pyridin-4-ylpiperidin-1-yl)quinoline-2-carboxamide;

N-{4-[(3S,5R)-3-amino-5-methylpiperidin-1-yl]pyridin-3-yl}-7-(4-pyridin-4-ylpiperidin-1-yl)quinoline-2-carboxamide;

N-{4-[(3R,4R,5S)-3-amino-4-hydroxy-5-methylpiperidin-1-yl]pyridin-3-yl}-7-(4-ethyl-3-oxopiperazin-1-yl)quinoline-2-carboxamide;

N-{4-[(3S,5R)-3-amino-5-methylpiperidin-1-yl]pyridin-3-yl}-7-(4-ethyl-3-oxopiperazin-1-yl)quinoline-2-carboxamide;

N-{4-[(3R,4R,5S)-3-amino-4-hydroxy-5-methylpiperidin-1-yl]pyridin-3-yl}-7-(4-methoxypiperidin-1-yl)quinoline-2-carboxamide;

N-{4-[(3S,5R)-3-amino-5-methylpiperidin-1-yl]pyridin-3-yl}-7-(4-methoxypiperidin-1-yl)quinoline-2-carboxamide;

N-{4-[(3R,4R,5S)-3-amino-4-hydroxy-5-methylpiperidin-1-yl]pyridin-3-yl}-7-(4-morpholin-4-ylpiperidin-1-yl)quinoline-2-carboxamide;

N-{4-[(3S,5R)-3-amino-5-methylpiperidin-1-yl]pyridin-3-yl}-7-(4-morpholin-4-ylpiperidin-1-yl)quinoline-2-carboxamide;

N-{4-[(3R,4R,5S)-3-amino-4-hydroxy-5-methylpiperidin-1-yl]pyridin-3-yl}-7-[3-(trifluoromethyl)pyrrolidin-1-yl]quinoline-2-carboxamide;

N-{4-[(3S,5R)-3-amino-5-methylpiperidin-1-yl]pyridin-3-yl}-7-[3-(trifluoromethyl)pyrrolidin-1-yl]quinoline-2-carboxamide;

N-{4-[(3R,4R,5S)-3-amino-4-hydroxy-5-methylpiperidin-1-yl]pyridin-3-yl}-7-pyrrolidin-1-ylquinoline-2-carboxamide;

N-{4-[(3S,5R)-3-amino-5-methylpiperidin-1-yl]pyridin-3-yl}-7-pyrrolidin-1-ylquinoline-2-carboxamide;

N-{4-[(3R,4R,5S)-3-amino-4-hydroxy-5-methylpiperidin-1-yl]pyridin-3-yl}-7-(3,3-dimethylazetidin-1-yl)quinoline-2-carboxamide;

N-{4-[(3S,5R)-3-amino-5-methylpiperidin-1-yl]pyridin-3-yl}-7-(3,3-dimethylazetidin-1-yl)quinoline-2-carboxamide;

N-{4-[(3S,5R)-3-amino-5-methylpiperidin-1-yl]pyridin-3-yl}-7-azetidin-1-ylquinoline-2-carboxamide;

N-{4-[(3R,4R,5S)-3-amino-5-cyclopropyl-4-hydroxypiperidin-1-yl]pyridin-3-yl}-7-(2,6-difluoro-4-methoxyphenyl)-1,5-naphthyridine-2-carboxamide;

N-{4-[(3R,4R,5S)-3-amino-5-cyclopropyl-4-hydroxypiperidin-1-yl]pyridin-3-yl}-7-(6-methoxypyridin-3-yl)-1,5-naphthyridine-2-carboxamide;

N-{4-[(3R,4R,5S)-3-amino-5-cyclopropyl-4-hydroxypiperidin-1-yl]pyridin-3-yl}-7-(6-morpholin-4-ylpyridin-3-yl)-1,5-naphthyridine-2-carboxamide;

N-{4-[(3R,4R,5S)-3-amino-5-cyclopropyl-4-hydroxypiperidin-1-yl]pyridin-3-yl}-7-(1-ethyl-1H-pyrazol-4-yl)-1,5-naphthyridine-2-carboxamide;

N-{4-[(3R,4R,5S)-3-amino-5-cyclopropyl-4-hydroxypiperidin-1-yl]pyridin-3-yl}-7-(1-methyl-1H-pyrazol-4-yl)-1,5-naphthyridine-2-carboxamide;

N-{4-[(3R,4R,5S)-3-amino-5-cyclopropyl-4-hydroxypiperidin-1-yl]pyridin-3-yl}-7-(3-oxa-9-azaspiro[5.5]undec-9-yl)-1,5-naphthyridine-2-carboxamide;

N-{4-[(3R,4R,5S)-3-amino-5-cyclopropyl-4-hydroxypiperidin-1-yl]pyridin-3-yl}-7-(4-cyanopiperidin-1-yl)-1,5-naphthyridine-2-carboxamide;

N-{4-[(3R,4R,5S)-3-amino-5-cyclopropyl-4-hydroxypiperidin-1-yl]pyridin-3-yl}-7-(1-oxa-8-azaspiro[4.5]dec-8-yl)-1,5-naphthyridine-2-carboxamide;

N-{4-[(3R,4R,5S)-3-amino-4-hydroxy-5-methylpiperidin-1-yl]pyridin-3-yl}-7-(1-methyl-1H-pyrazol-4-yl)quinoline-2-carboxamide;

N-{4-[(3R,4R,5S)-3-amino-4-hydroxy-5-methylpiperidin-1-yl]pyridin-3-yl}-7-(1-ethyl-1H-pyrazol-4-yl)quinoline-2-carboxamide;

N-{4-[(3R,4R,5S)-3-amino-4-hydroxy-5-methylpiperidin-1-yl]pyridin-3-yl}-7-(6-methoxypyridin-3-yl)quinoline-2-carboxamide;

N-{4-[(3R,4R,5S)-3-amino-4-hydroxy-5-methylpiperidin-1-yl]pyridin-3-yl}-7-(6-morpholin-4-ylpyridin-3-yl)quinoline-2-carboxamide;

N-(4-((3R,4R,5S)-3-amino-4-hydroxy-5-methylpiperidin-1-yl)pyridin-3-yl)-7-(pyridin-3-yl)quinoline-2-carboxamide;

N-{4-[(3S,5R)-3-amino-5-methylpiperidin-1-yl]pyridin-3-yl}-7-(1-methyl-1H-pyrazol-4-yl)quinoline-2-carboxamide;

N-{4-[(3S,5R)-3-amino-5-methylpiperidin-1-yl]pyridin-3-yl}-7-(2-cyanophenyl)quinoline-2-carboxamide;

N-(4-((3S,5R)-3-amino-5-methylpiperidin-1-yl)pyridin-3-yl)-7-(4-hydroxypiperidin-1-yl)quinoline-2-carboxamide;

N-{4-[(3S,5R)-3-amino-5-(trifluoromethyl)piperidin-1-yl]pyridin-3-yl}-7-(2-cyanophenyl)-1,5-naphthyridine-2-carboxamide; and N-{4-[(3R,4R,5S)-3-amino-4-hydroxy-5-methylpiperidin-1-yl]pyridin-3-yl}-7-[6-(tetrahydro-2H-pyran-4-yloxy)pyridin-3-yl]quinoline-2-carboxamide, or a pharmaceutically acceptable salt thereof, wherein the disease or disorder is a myeloproliferative disorder, or a cancer selected from a solid tumor and a hematological cancer.

40. A method of treating a disease or disorder comprising administering to a patient in need of such treatment a therapeutically effective amount of the compound N-{4-[(3R,4R,5S)-3-Amino-4-hydroxy-5-methylpiperidin-1-yl]pyridin-3-yl}-7-morpholin-4-ylquinoline-2-carboxamide, or a pharmaceutically acceptable salt thereof, wherein the disease or disorder is a myeloproliferative disorder, or a cancer selected from a solid tumor and a hematological cancer.

41. The method of claim 1, wherein the solid tumor is colon cancer.

42. The method of claim 1, wherein the solid tumor is esophageal cancer.

43. The method of claim 1, wherein the solid tumor is renal cancer.

44. The method of claim 1, wherein the solid tumor is hepatic cancer.

45. The method of claim 1, wherein the solid tumor is gastric cancer.

46. The method of claim 1, wherein the solid tumor is breast cancer.

47. The method of claim 1, wherein the solid tumor is lung cancer.

48. The method of claim 1, wherein the solid tumor is a cancer of the head or neck.

49. The method of claim 1, wherein the solid tumor is bladder cancer.

50. The method of claim 1, wherein the solid tumor is pancreatic cancer.

51. The method of claim 1, wherein the solid tumor is prostate cancer.

52. The method of claim 1, wherein the hematological cancer is lymphoma.

53. The method of claim 1, wherein the hematological cancer is leukemia.

54. The method of claim 1, wherein the hematological cancer is multiple myeloma (MM).

55. The method of claim 1, wherein the hematological cancer is acute myeloid leukemia (AML).

56. The method of claim 1, wherein the hematological cancer is diffuse large B-cell lymphoma (DLBCL).

57. The method of claim 1, wherein the hematological cancer is acute lymphoblastic leukemia (ALL).

58. The method of claim 1, wherein the hematological cancer is chronic lymphocytic leukemia (CLL).

59. The method of claim 1, wherein the hematological cancer is mantle cell lymphoma.

60. The method of claim 1, wherein the hematological cancer is non-Hodgkin lymphoma.

61. The method of claim 60, wherein the non-Hodgkin lymphoma is relapsed non-Hodgkin lymphoma, refractory non-Hodgkin lymphoma, or recurrent follicular non-Hodgkin lymphoma.

62. The method of claim 1, wherein the hematological cancer is Hodgkin lymphoma.

63. The method of claim 1, wherein the myeloproliferative disorder is polycythemia vera.

64. The method of claim 1, wherein the myeloproliferative disorder is essential thrombocythemia.

65. The method of claim 1, wherein the myeloproliferative disorder is chronic myelogenous leukemia.

66. The method of claim 1, wherein the myeloproliferative disorder is myelofibrosis.

67. The method of claim 1, wherein the myeloproliferative disorder is primary myelofibrosis.

68. The method of claim 1, wherein the myeloproliferative disorder is myelofibrosis with myeloid metaplasia.

69. The method of claim 1, wherein the myeloproliferative disorder is post-essential thrombocythemia myelofibrosis.

70. The method of claim 1, wherein the myeloproliferative disorder is post polycythemia vera myelofibrosis.

* * * * *

UNITED STATES PATENT AND TRADEMARK OFFICE
CERTIFICATE OF CORRECTION

PATENT NO. : 9,890,162 B2
APPLICATION NO. : 15/405742
DATED : February 13, 2018
INVENTOR(S) : Yaping Sun et al.

Page 1 of 1

It is certified that error appears in the above-identified patent and that said Letters Patent is hereby corrected as shown below:

In the Claims

Column 103, Line 19, Claim 1, delete "O ($C_{1-6}$ alkyl);" and insert -- O($C_{1-6}$ alkyl); --.

Column 103, Line 36, Claim 1, delete "$R^{a1}$is" and insert -- $R^{a1}$ is --.

Column 104, Line 47, Claim 32, delete "claim 9" and insert -- claim 19 --.

Column 104, Line 50, Claim 33, delete "$C_{l-6}$" and insert -- $C_{1-6}$ --.

Signed and Sealed this
Seventeenth Day of April, 2018

Andrei Iancu
*Director of the United States Patent and Trademark Office*